(12) United States Patent
Kalyanaraman et al.

(10) Patent No.: US 11,897,910 B2
(45) Date of Patent: *Feb. 13, 2024

(54) MITO-HONOKIOL COMPOUNDS AND METHODS OF SYNTHESIS AND USE THEREOF

(71) Applicants: The Medical College of Wisconsin, Inc., Milwaukee, WI (US); Aix-Marseille Universite, Marseilles (FR)

(72) Inventors: Balaraman Kalyanaraman, Milwaukee, WI (US); Jacek Michal Zielonka, Wauwatosa, WI (US); Gang Cheng, Milwaukee, WI (US); Micael J. Hardy, Nîmes (FR); Olivier Ouari, Marseilles (FR); Ming You, Elm Grove, WI (US)

(73) Assignees: The Medical College of Wisconsin, Inc., Milwaukee, WI (US); Aix-Marseille Universite, Marseilles (FR)

( * ) Notice: Subject to any disclaimer, the term of this patent is extended or adjusted under 35 U.S.C. 154(b) by 409 days.

This patent is subject to a terminal disclaimer.

(21) Appl. No.: 17/099,268

(22) Filed: Nov. 16, 2020

(65) Prior Publication Data
US 2021/0070787 A1   Mar. 11, 2021

Related U.S. Application Data

(63) Continuation-in-part of application No. 16/714,461, filed on Dec. 13, 2019, now Pat. No. 11,083,739, and a continuation-in-part of application No. 15/735,405, filed as application No. PCT/US2016/036827 on Jun. 10, 2016, now Pat. No. 10,836,782.

(60) Provisional application No. 62/779,795, filed on Dec. 14, 2018, provisional application No. 62/174,185, filed on Jun. 11, 2015.

(51) Int. Cl.
| | |
|---|---|
| C07F 9/54 | (2006.01) |
| A61P 35/04 | (2006.01) |
| A61K 31/19 | (2006.01) |
| A61K 31/7004 | (2006.01) |
| A61K 45/06 | (2006.01) |

(52) U.S. Cl.
CPC ............ *C07F 9/5456* (2013.01); *A61P 35/04* (2018.01); *A61K 31/19* (2013.01); *A61K 31/7004* (2013.01); *A61K 45/06* (2013.01)

(58) Field of Classification Search
CPC ................... C07F 9/5456; C07F 9/54
See application file for complete search history.

(56) References Cited

U.S. PATENT DOCUMENTS

| | | | |
|---|---|---|---|
| 8,586,627 | B2 | 11/2013 | Arbiser |
| 8,822,531 | B2 | 9/2014 | Arbiser |
| 2004/0105906 | A1 | 6/2004 | Arbiser et al. |
| 2008/0300298 | A1 | 12/2008 | Arbiser et al. |

FOREIGN PATENT DOCUMENTS

| | | |
|---|---|---|
| WO | 99/00346 | 1/1999 |
| WO | 00/40532 | 7/2000 |
| WO | 2015/066432 | 5/2015 |

OTHER PUBLICATIONS

Tse et al. (2005). Honokiol inhibits TNF-alpha-stimulated NF-kappas activation and NF-kappaB-regulated gene expression through suppression of IKK activation. Biochem Pharmacol 70, 1443-1457.
Wu et al. (2014). EGFR-STAT3 signaling promotes formation of malignant peripheral nerve sheath tumors. Oncogene 33, 173-180.
Lin et al. (2012) In vitro growth inhibition of human cancer cells by novel honokiol analogs. Bioorg. Med. Chem., 20, 3202-3211.
Ma et al. (2011) Structural modification of honokiol, a biphenyl occurring in Magnolia officinalis: the evaluation of honokiol analogues as inhibitors of angiogenesis and for their cytotoxicity and structure-activity relationship. J. Med. Chem., 54, 6469-6481.
Perche et al. (2013) published on-line 2013:705265.
Hu et al. (2008) Liposomal honokiol, a potent anti-angiogenesis agent, in combination with radiotherapy produces a synergistic antitumor efficacy without increasing toxicity. Exp Mol Med. 40:617-28. Hu J. et al.
Bai et al. (2003) Honokiol, a small molecular weight natural product, inhibits angiogenesis in vitro and tumor growth in vivo. J Biol Chem. 278:35501-7.
International Search Report and Written Opinion for International Patent Application No. PCT/US2016/036827 dated Nov. 3, 2016.
MedicineNet.com (2004) Web: http://www.medterms.com (Year: 2004).
Alas et al. (2003). Inhibition of constitutive STAT3 activity sensitizes resistant non-Hodgkin's lymphoma and multiple myeloma to chemotherapeutic drug-mediated apoptosis. Clin Cancer Res 9, 316-326.
Anders et al. (2015). HTSeq—a Python framework to work with high-throughput sequencing data. Bioinformatics 31, 166-169.
Bewry et al. (2008). Stat3 contributes to resistance toward BCR-ABL inhibitors in a bone marrow microenvironment model of drug resistance. Mol Cancer Ther 7, 3169-3175.
Bradford et al. (2013). RNA-Seq Differentiates Tumour and Host mRNA Expression Changes Induced by Treatment of Human Tumour Xenografts with the VEGFR Tyrosine Kinase Inhibitor Cediranib. PLoS One 8, e66003.
Chen et al. (2004). Honokiol: a potent chemotherapy candidate for human colorectal carcinoma. World J Gastroenterol 10, 3459-3463.
Chen et al. (2010). Honokiol induces cell apoptosis in human chondrosarcoma cells through mitochondrial dysfunction and endoplasmic reticulum stress. Cancer Lett 291, 20-30.

(Continued)

*Primary Examiner* — Shobha Kantamneni
(74) *Attorney, Agent, or Firm* — Quarles & Brady LLP

(57) ABSTRACT

The present invention provides mito-honokiol or mito-magnolol compounds, pharmaceutical compositions thereof, and methods of using the mito-honokiol or mito-magnolol compounds in the treatment of cancer.

19 Claims, 48 Drawing Sheets

(29 of 48 Drawing Sheet(s) Filed in Color)

(56) References Cited

OTHER PUBLICATIONS

Cheng et al. (2012). Mitochondria-targeted drugs synergize with 2-deoxyglucose to trigger breast cancer cell death. Cancer Res 72, 2634-2644.
Cheng et al. (2014). Profiling and targeting of cellular bioenergetics: inhibition of pancreatic cancer cell proliferation. Br J Cancer, 1-9.
Cheng et al. (2013). Mitochondria-targeted vitamin E analogs inhibit breast cancer cell energy metabolism and promote cell death. BMC Cancer 13, 285-285.
Crane et al. (2009). Honokiol-mediated inhibition of PI3K/mTOR pathway: a potential strategy to overcome immunoresistance in glioma, breast, and prostate carcinoma without impacting T cell function. J Immunother 32, 585-592.
De Simone et al. (2015). Th17-type cytokines, IL-6 and TNF-alpha synergistically activate STAT3 and NF-kB to promote colorectal cancer cell growth. Oncogene 34, 3493-3503.
Deng et al. (2008). Involvement of p38 mitogen-activated protein kinase pathway in honokiol-induced apoptosis in a human hepatoma cell line (hepG2). Liver Int 28, 1458-1464.
Gane et al. (2010). The mitochondria-targeted anti-oxidant mitoquinone decreases liver damage in a phase II study of hepatitis C patients. Liver Int 30, 1019-1026.
Garcia et al. (2008). Honokiol suppresses survival signals mediated by Ras-dependent phospholipase D activity in human cancer cells. Clin Cancer Res 14, 4267-4274.
Goldberg et al. (2015). Lung Cancer Brain Metastases. Cancer J 21, 398-403.
Hahm et al. (2007). Honokiol causes G0-G1 phase cell cycle arrest in human prostate cancer cells in association with suppression of retinoblastoma protein level/phosphorylation and inhibition of E2F1 transcriptional activity. Mol Cancer Ther 6, 2686-2695.
Jemal et al. (2010). Cancer statistics, 2010. CA: a cancer journal for clinicians 60, 277-300.
Koizumi et al. (2005). Establishment of a human non-small cell lung cancer cell line resistant to gefitinib. Int J Cancer 116, 36-44.
Lang Mead et al. (2009). Ultrafast and memory-efficient alignment of short DNA sequences to the human genome. Genome Biol 10, R25.
Lee et al. (2014). Drug resistance via feedback activation of Stat3 in oncogene-addicted cancer cells. Cancer Cell 26, 207-221.
Lee et al. (2016). Inhibition of IGF1 R signaling abrogates resistance to afatinib (BIBW2992) in EGFR T790M mutant lung cancer cells. Mol Carcinog 55, 991-1001.
Li et al. (2016). Redox homeostasis protects mitochondria through accelerating ROS conversion to enhance hypoxia resistance in cancer cells. Sci Rep 6, 22831.
Lin et al. (2012). Honokiol traverses the blood-brain barrier and induces apoptosis of neuroblastoma cells via an intrinsic bax-mitochondrion-cytochrome c-caspase protease pathway. Neuro Oncol 14, 302-314.
Lin et al. (2011). STAT3 is necessary for proliferation and survival in colon cancer-initiating cells. Cancer Res 71, 7226-7237.
Martin et al. (2013). Inducing apoptosis of cancer cells using small-molecule plant compounds that bind to GRP78. Br J Cancer 109, 433-443.
McManus et al. (2011). The mitochondria-targeted antioxidant MitoQ prevents loss of spatial memory retention and early neuropathology in a transgenic mouse model of Alzheimer's disease. J Neurosci 31, 15703-15715.
Nair et al. (2012). Role of STAT3 in Transformation and Drug Resistance in CML. Front Oncol 2, 30.
Nguyen et al. (2009). WNT/TCF signaling through LEF1 and HOXB9 mediates lung adenocarcinoma metastasis. Cell 138, 51-62.
Pan et al. (2014). Honokiol inhibits lung tumorigenesis through inhibition of mitochondrial function. Cancer Prev Res (Phila) 7, 1149-1159.
Park et al. (2009). Down-regulation of c-Src/EGFR-mediated signaling activation is involved in the honokiol-induced cell cycle arrest and apoptosis in MDA-MB-231 human breast cancer cells. Cancer Lett 277, 133-140.
Phelps et al. (1996). NCI-Navy Medical Oncology Branch cell line data base. J Cell Biochem Suppl 24, 32-91.
Pillai et al. (2015). Honokiol blocks and reverses cardiac hypertrophy in mice by activating mitochondrial Sirt3. Nat Commun 6, 6656.
Robinson et al. (2010). edgeR: a Bioconductor package for differential expression analysis of digital gene expression data. Bioinformatics 26, 139-140.
Rossello et al. (2013). Next-generation sequence analysis of cancer xenograft models. PLoS One 8, e74432.
Trap Nell et al. (2009). TopHat: discovering splice junctions with RNA-Seq. Bioinformatics 25, 1105-1111.
Tsai et al. (1994). Pharmacokinetics of honokiol after intravenous administration in rats assessed using high-performance liquid chromatography. J Chromatogr B Biomed Appl 655, 41-45.
Vazquez-Martin et al. (2013). IGF-1 R/epithelial-to-mesenchymal transition (EMT) crosstalk suppresses the erlotinib-sensitizing effect of EGFR exon 19 deletion mutations. Sci Rep 3, 2560.
Wang et al. (2011). Honokiol crosses BBB and BCSFB, and inhibits brain tumor growth in rat 9L intracerebral gliosarcoma model and human U251 xenograft glioma model. PLoS One 6, e18490.
Yang et al. (2015). STAT3 Inhibition Enhances the Therapeutic Efficacy of Immunogenic Chemotherapy by Stimulating Type 1 Interferon Production by Cancer Cells. Cancer Res 75, 3812-3822.
Yau et al. (2005). Inhibition of integrin-linked kinase by a selective small molecule inhibitor, QL T0254, inhibits the PI3K/PKB/mTOR, Stat3, and FKHR pathways and tumor growth, and enhances gemcitabine-induced apoptosis in human orthotopic primary pancreatic cancer xenografts. Cancer Res 65, 1497-1504.
Yu et al. (2015). Reversal of doxorubicin resistance in breast cancer by mitochondria-targeted pH-responsive micelles. Acta Biomater 14, 115-124.
Zhang et al. (2013). Mitochondrial localized Stat3 promotes breast cancer growth via phosphorylation of serine 727. J Biol Chem 288, 31280-31288.
Zhou et al. (2007). Activation of the PTEN/mTOR/STAT3 pathway in breast cancer stem-like cells is required for viability and maintenance. Proc Natl Acad Sci U SA 104, 16158-16163.
Lee et al. (2011) Therapeutic applications of compounds in the Magnolia family. Pharmacol. Ther., 130, 157-176.
Shigemura et al. (2007) Honokiol, a natural plant product, inhibits the bone metastatic growth of human prostate cancer cells. Cancer, 109, 1279-1289.
Woodbury et al. (2013) Neuro-modulating effects of honokiol: a review. Front. Neurol., 4, 130.
Fried et al. (2009) Honokiol, a multifunctional antiangiogenic and antitumor agent. Antioxid. Redox Signal., 11, 1139-1148.
Arora et al. (2012) Honokiol: a novel natural agent for cancer prevention and therapy. Curr. Mol. Med., 12, 1244-1252.
Ramsay et al. (2011) Pharm. Res., 28, 2731-2744.
Murphy et al. (2007) Targeting antioxidants to mitochondria by conjugation to lipophilic cations. Annu. Rev. Pharmacol. Toxicol., 47, 629-656.

Role of STAT3/Complex I in Mediating Mito-Honokiol's Inhibitory Effects

FIG. 9C
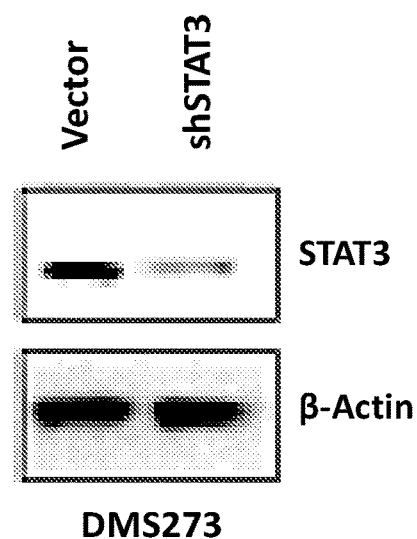
DMS273
FIG. 9D
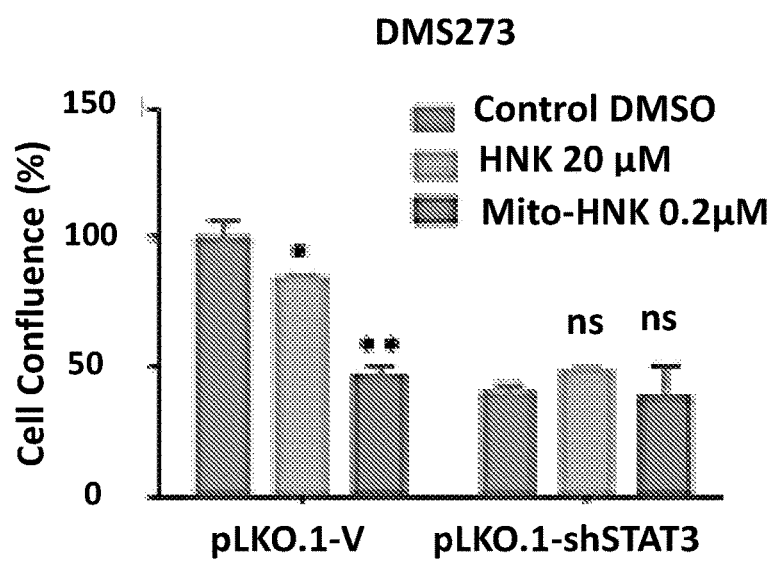
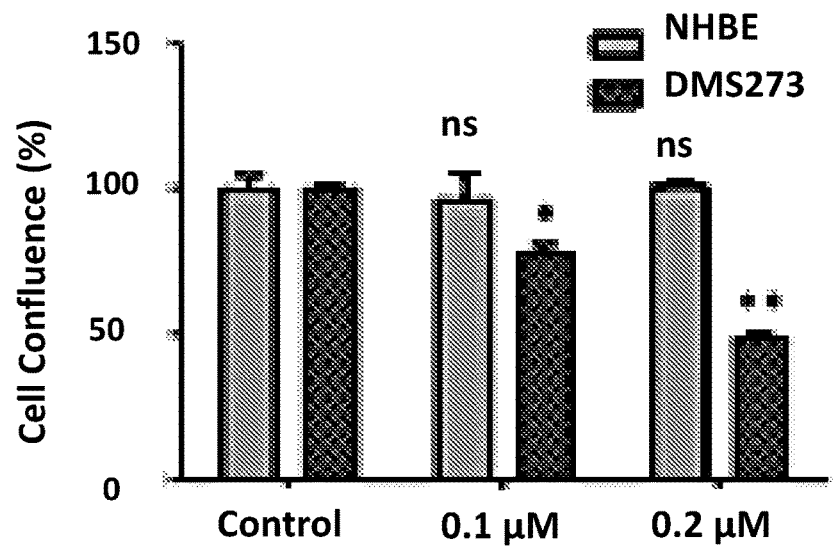
FIG. 9E

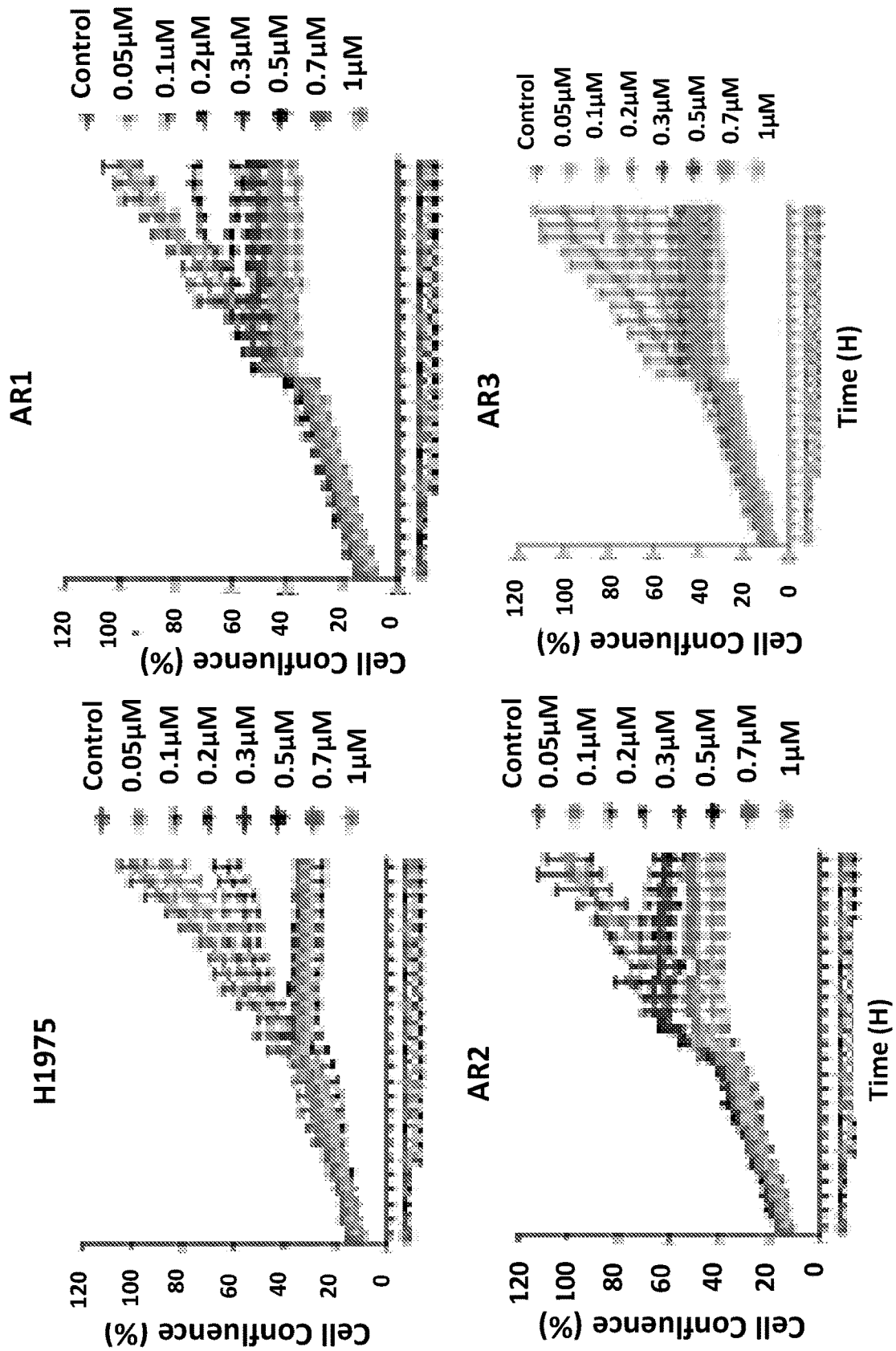
FIG. 10A. Effects of MitoHNK in EGFR TKI Drug Resistant Lung Cancer Cells FIG. 11A
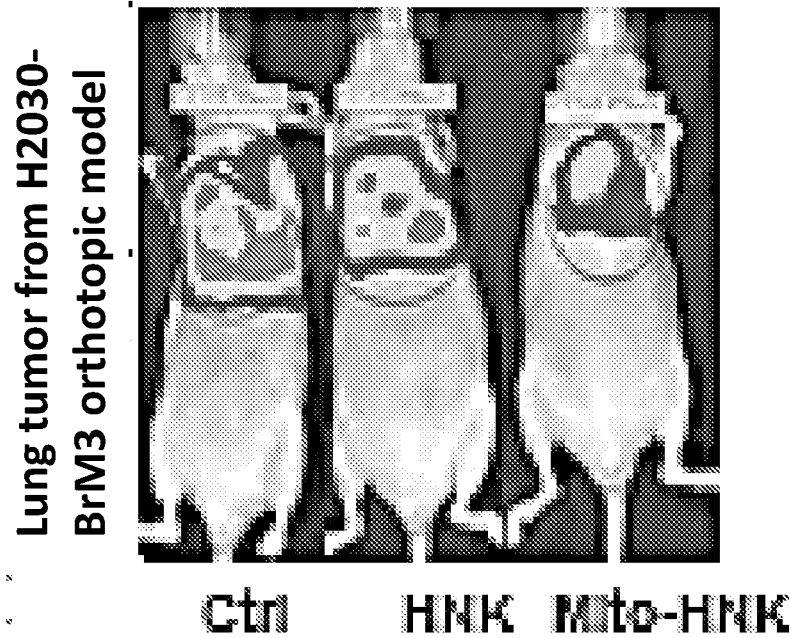
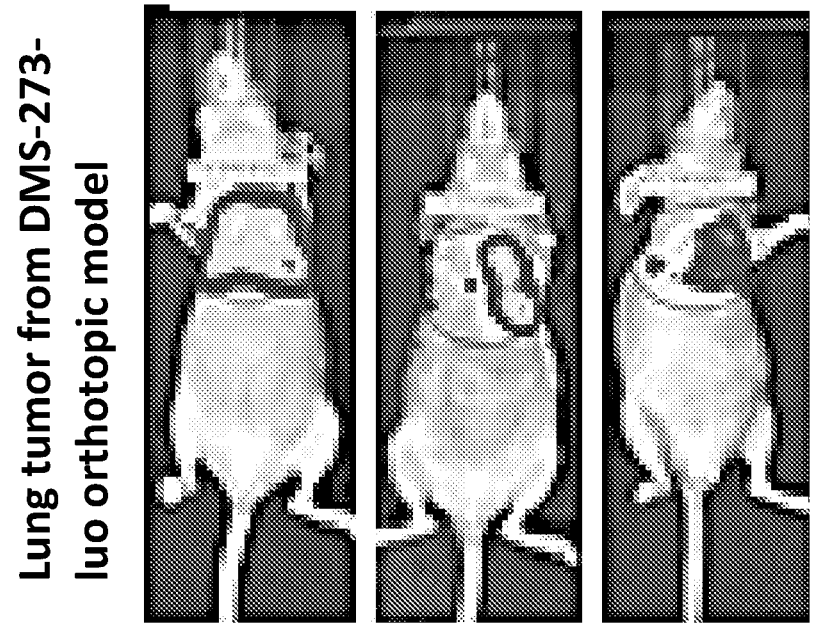
FIG. 11C FIG. 11B
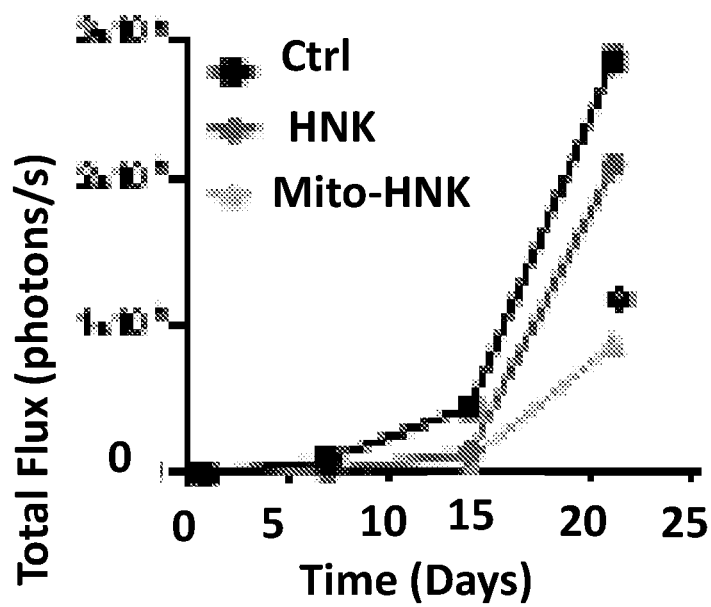
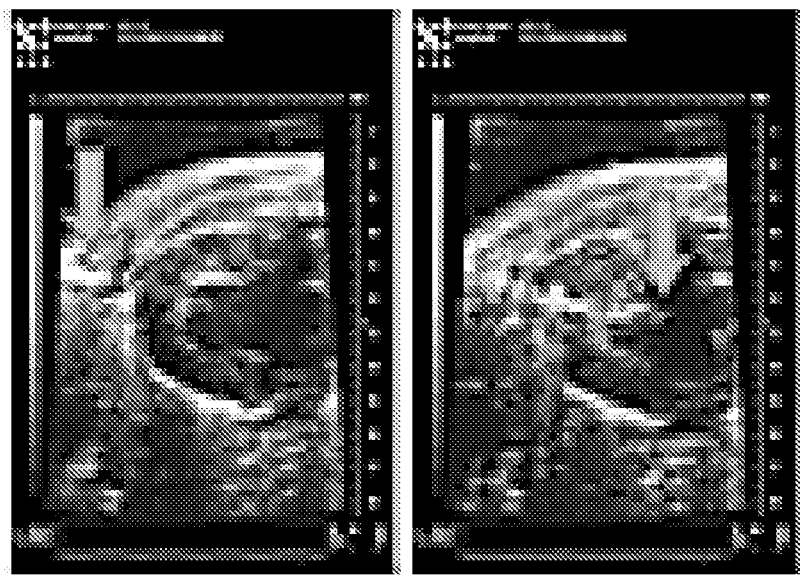
FIG. 12A FIG. 12B
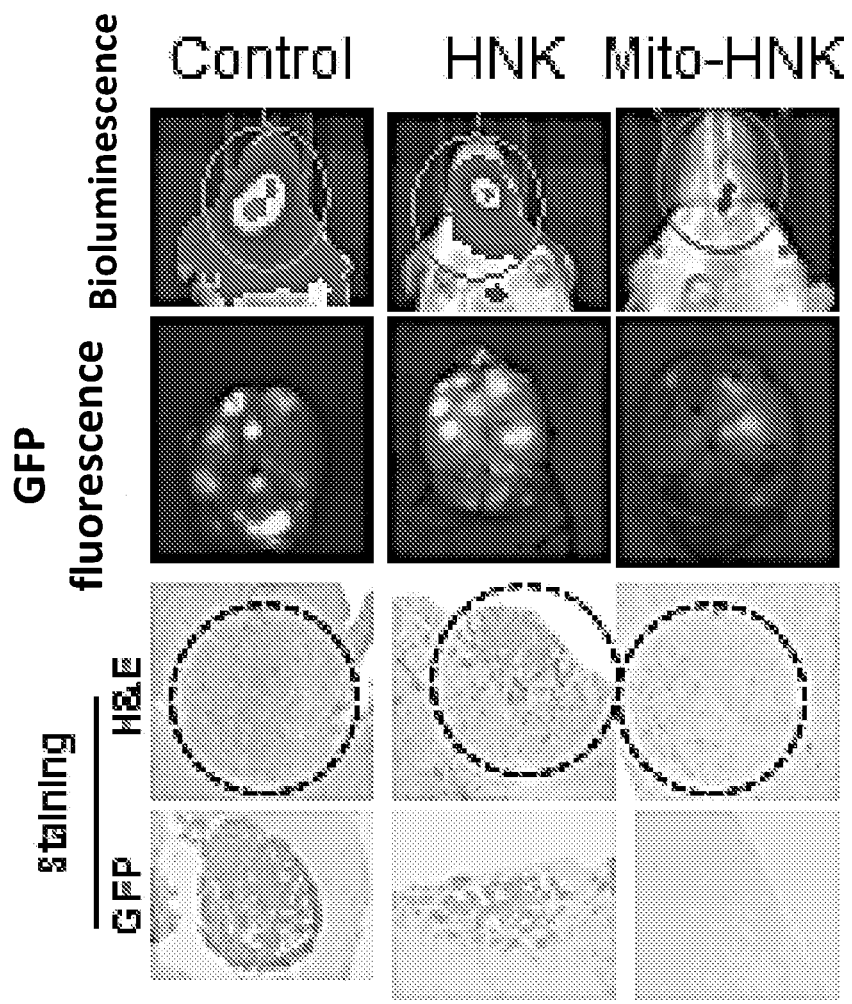
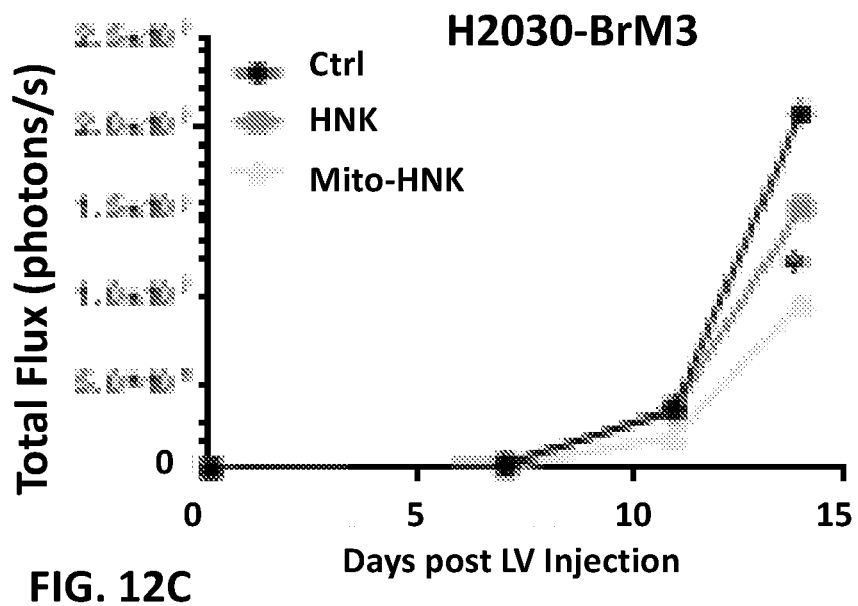
FIG. 12C FIG. 12D
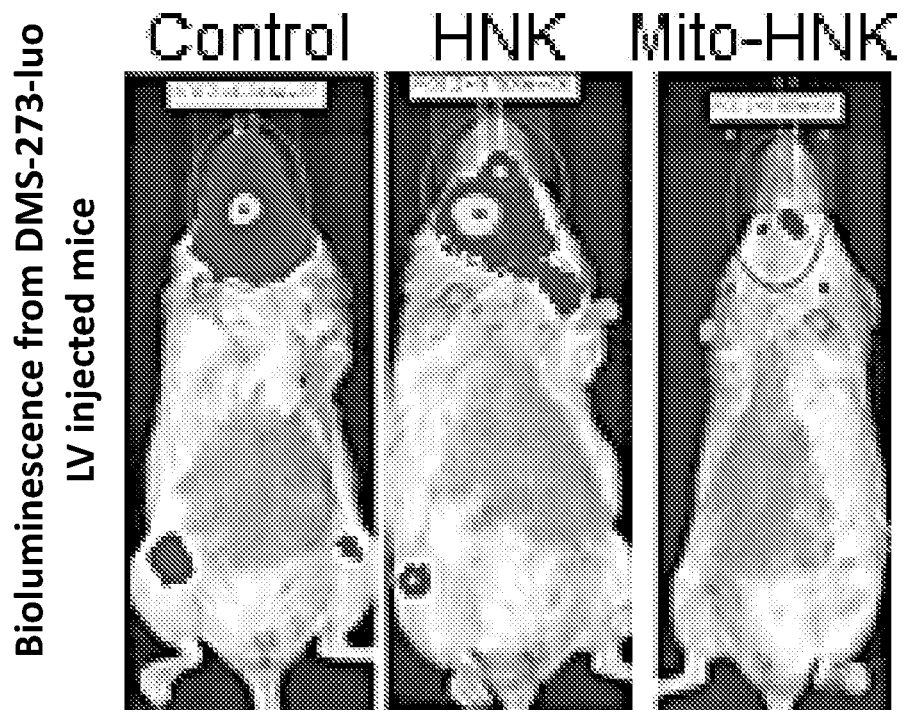
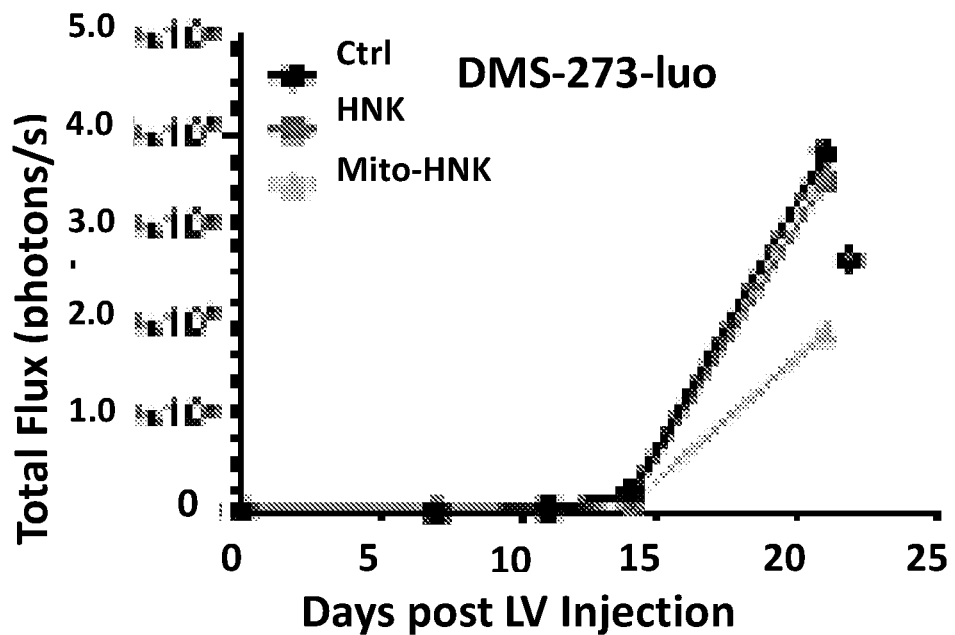
FIG. 12E U87 Cells
A.
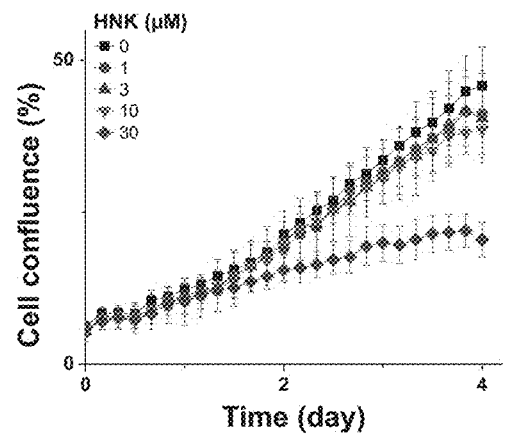
B.
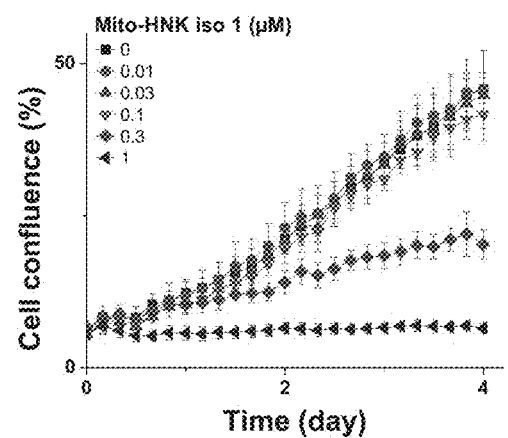
C.
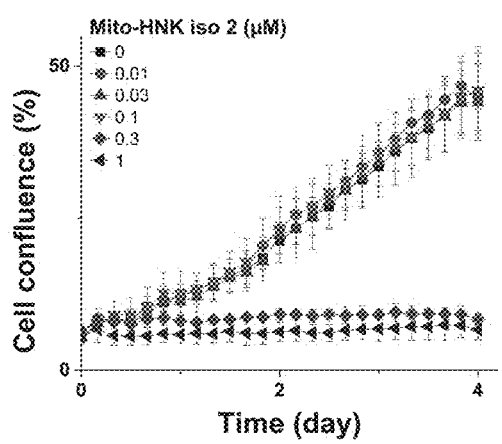
FIG. 14A-14D MiaPaCa-2 cells
A
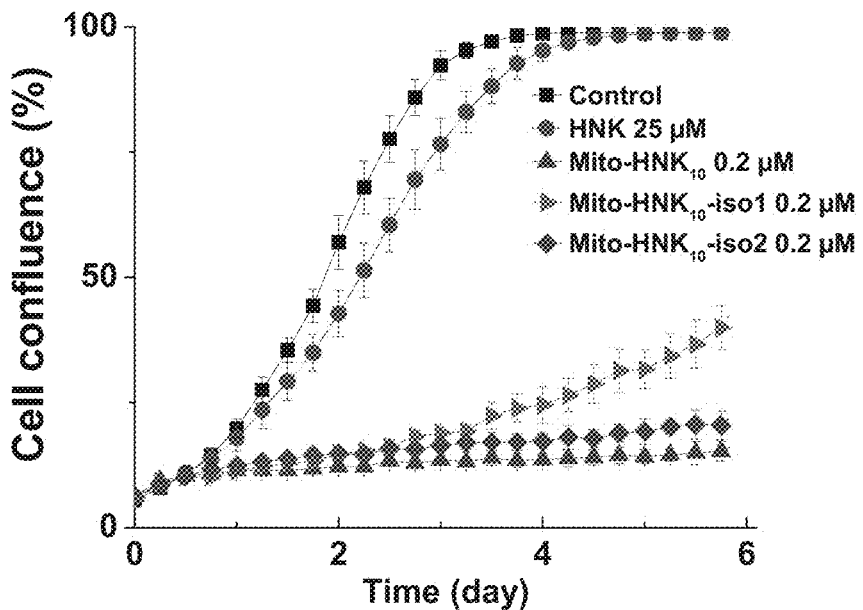
B
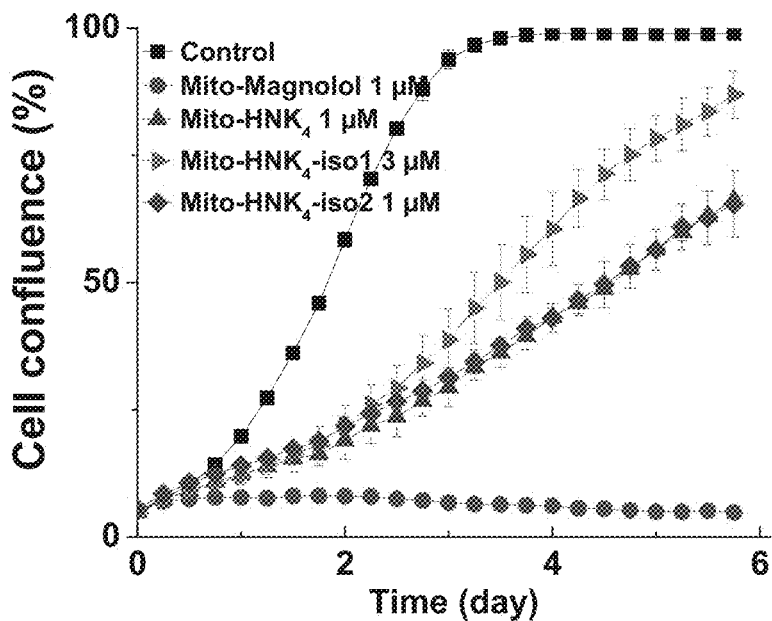
FIG. 15A-15F C
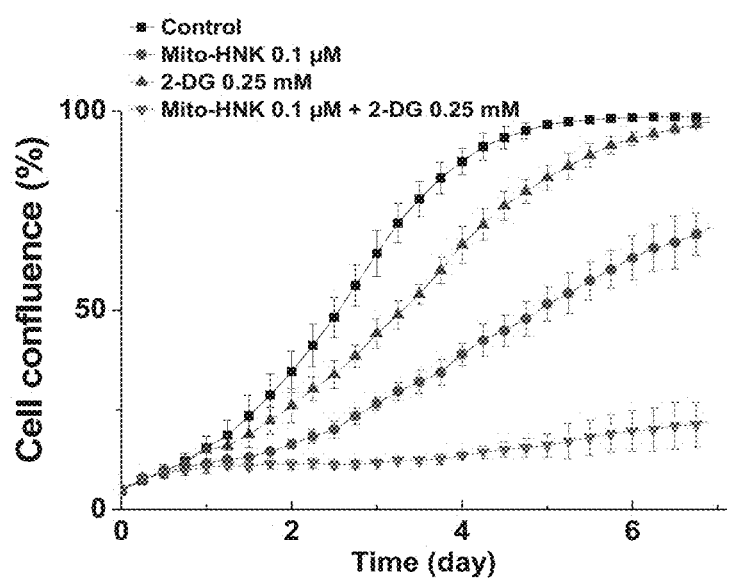
D
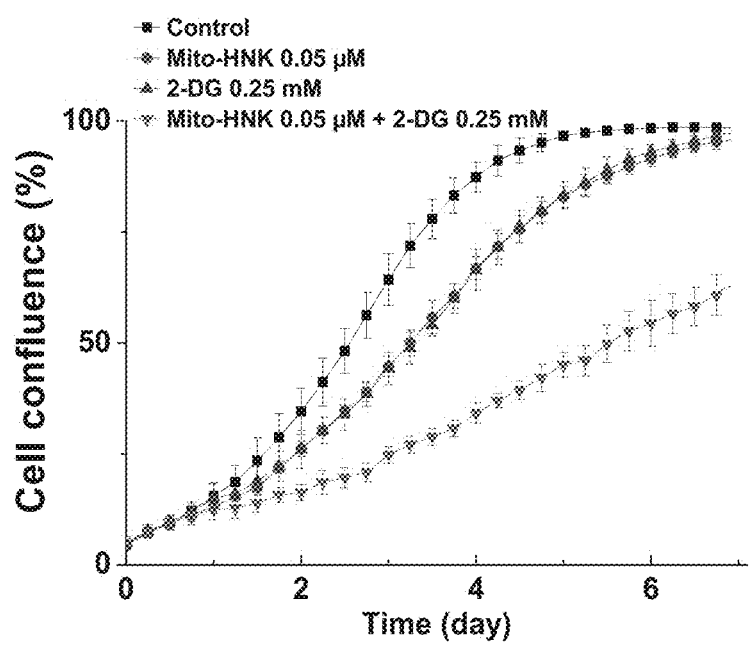
FIG. 15A-15F (Continued)

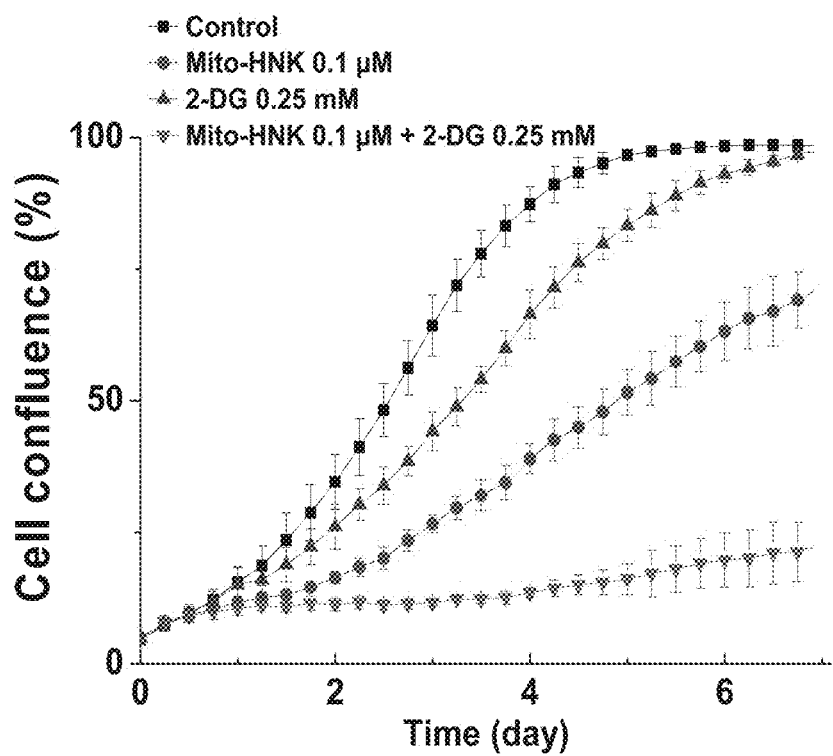
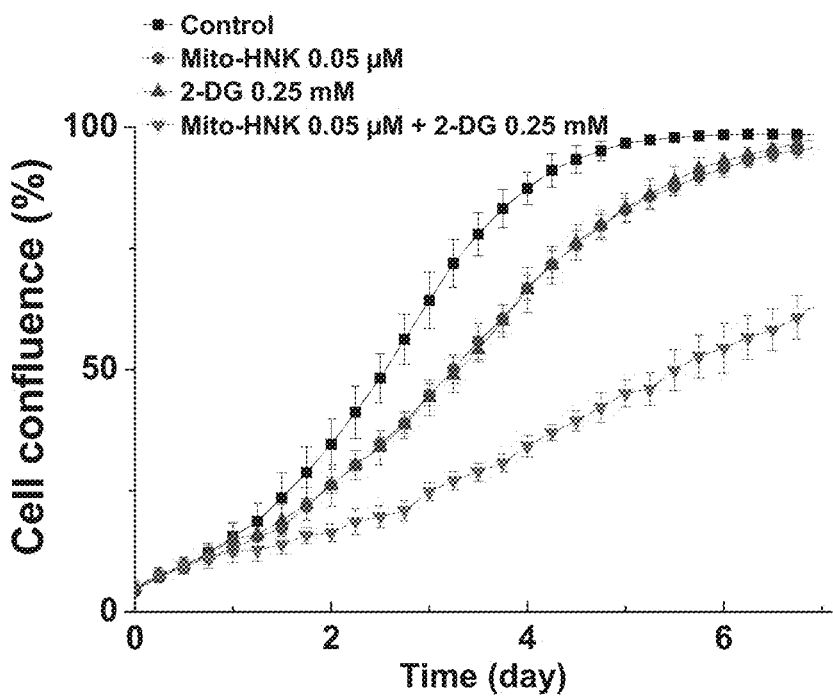
FIG. 15A-15F (continued)

D
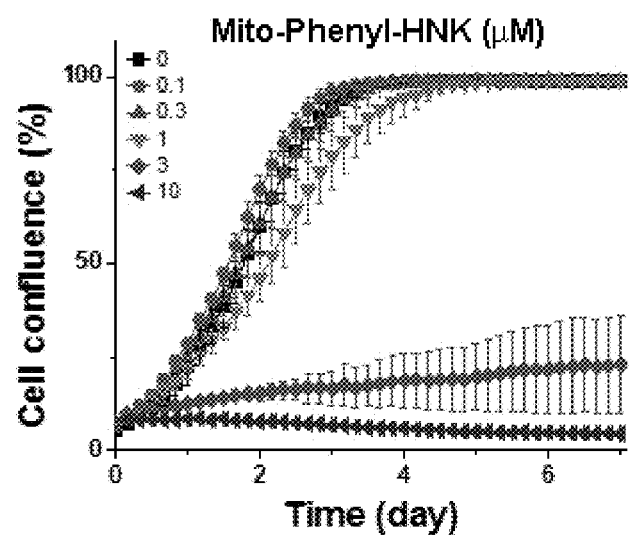
FIG. 16A-D (continued)

A
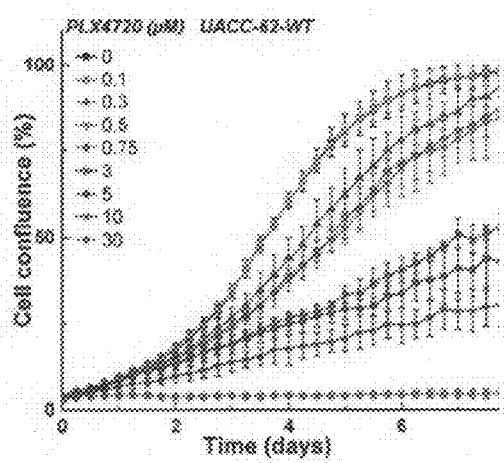
B
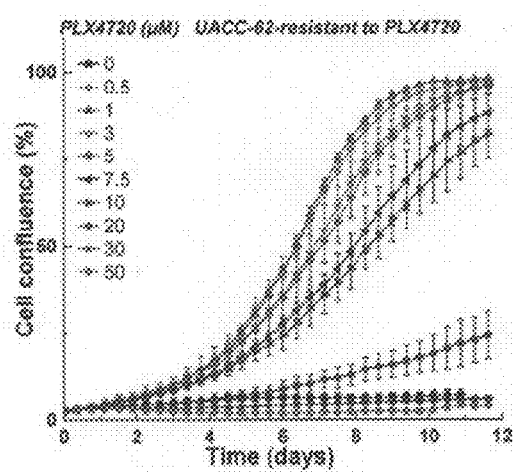
C
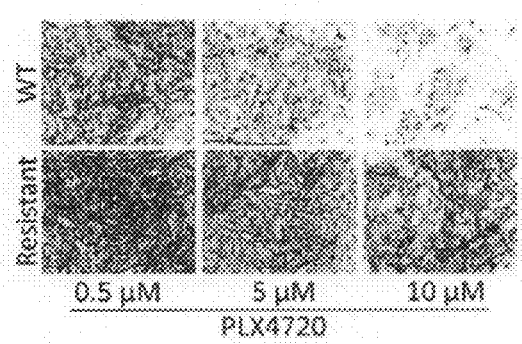
D
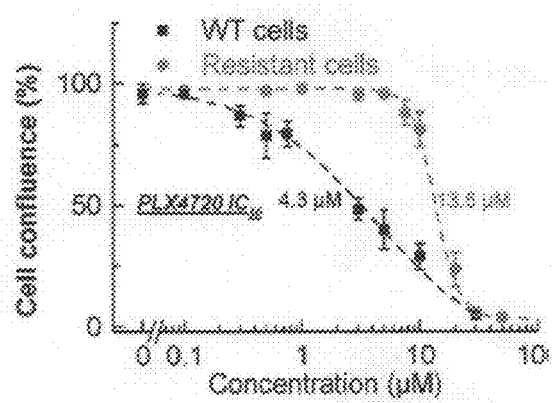
Fig. 21A-21F

E
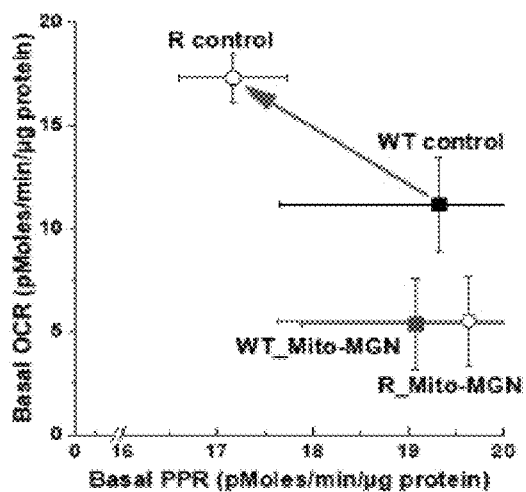
F
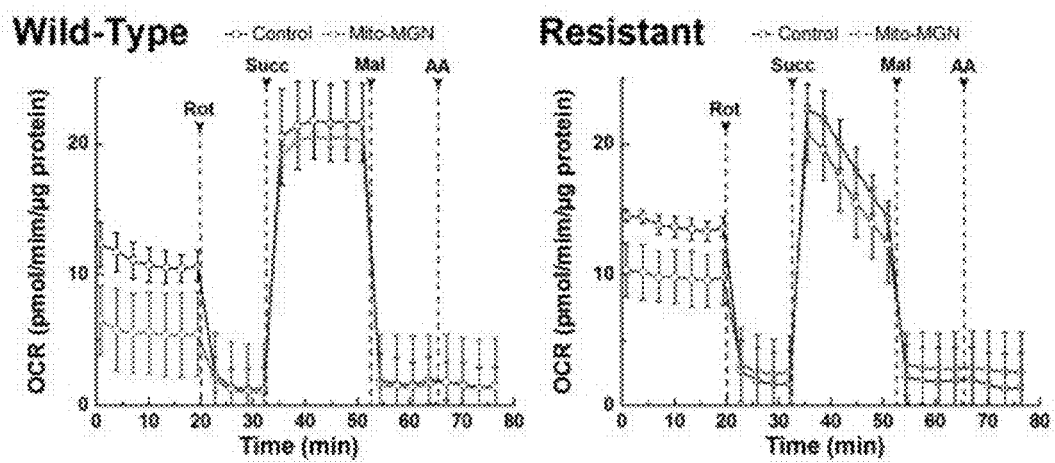
FIG. 21A-21F (continued)

A

B

A

B

C

A

B

A

B

C

A
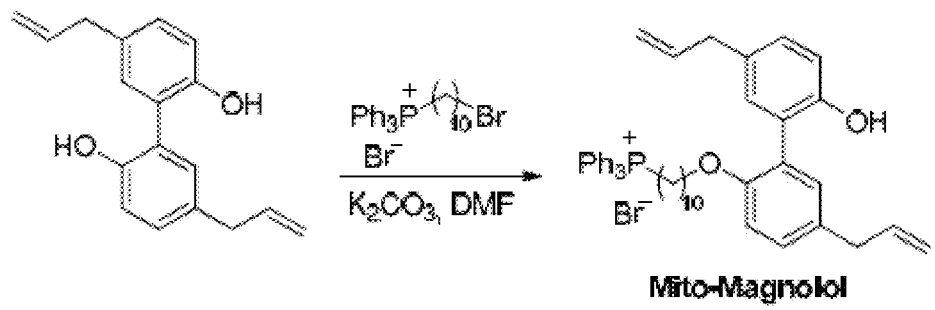
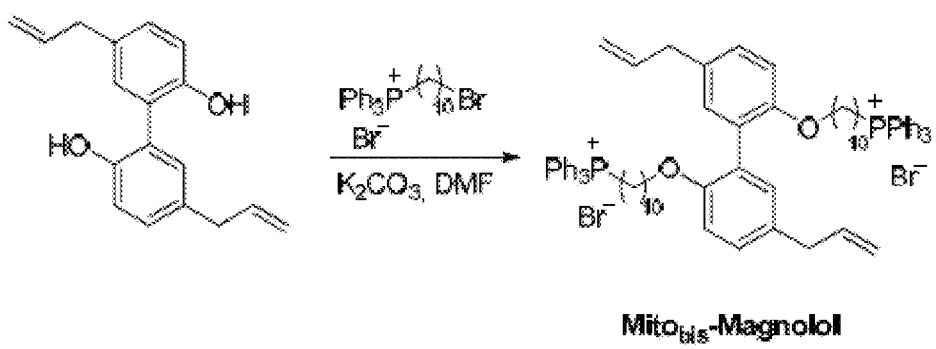
B
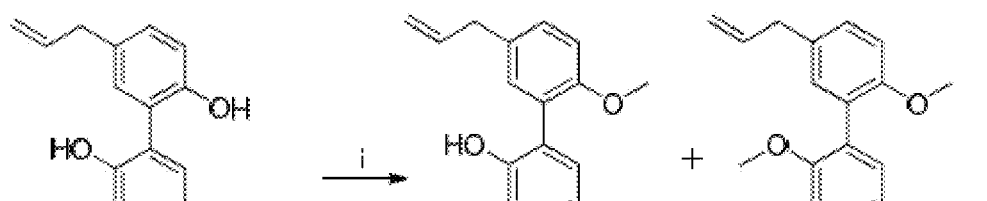
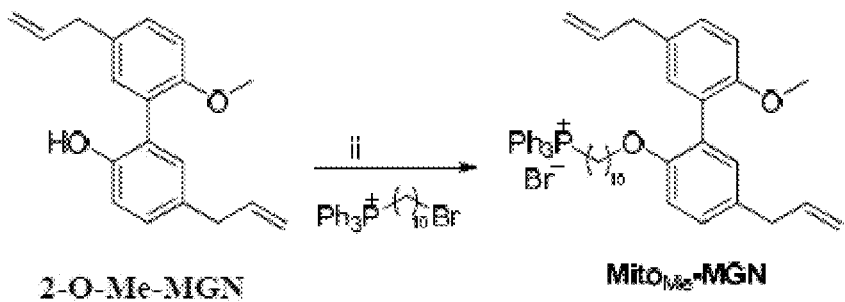
FIG. 29A-29B

R= H, Me; X= Alkyl chain, phenyl, PEG...; Y= H, $CF_3$, Me, Cl, OMe, $C(O)CH_3$, $NO_2$, $N(Me)_2$, ...

A

B

A

B

C

MITO-HONOKIOL COMPOUNDS AND METHODS OF SYNTHESIS AND USE THEREOF

CROSS-REFERENCE TO RELATED APPLICATIONS

This application is a continuation-in-part of U.S. application Ser. No. 15/735,405 filed on Dec. 11, 2017, granted as U.S. Pat. No. 10,836,782, which is a 371 national stage application of PCT/US16/36827 filed on Jun. 10, 2016 which claims priority to Provisional Application No. 62/174,185 filed on Jun. 11, 2015, and is a continuation-in-part of U.S. application Ser. No. 16/714,461 filed on Dec. 12, 2019 which claims priority to U.S. Provisional Application No. 62/779,795 filed on Dec. 14, 2018, the contents of all of which are incorporated by reference in their entireties.

STATEMENT REGARDING FEDERALLY SPONSORED RESEARCH OR DEVELOPMENT

Not Applicable.

FIELD OF THE INVENTION

This invention relates generally to mitochondria-targeting cationic drugs, specifically to mito-honokiol compounds and mito-magnolol compounds, and methods of using the compounds to treat cancer.

BACKGROUND

Honokiol is a natural biphenolic compound present in *Magnolia* bark extracts that has been reported to exert antitumor effects in several in vitro and in vivo models of cancer (e.g. melanoma, myeloma, lung, prostate). While the mechanism of this activity is currently under investigation, emerging evidence points to mitochondrial effects of honokiol, leading to decreased cellular respiration and decreased cellular energy status (decreased ATP and increased AMP levels).

Previous attempts to improve and enhance the efficacy of honokiol have involved modified honokiol to inhibit angiogenesis. However, these previous efforts have resulted in significant negative side effects, and have not been successful.

Linking therapeutics to triphenylphosphonium (TPP) has been shown to increase the accumulation of a wide variety of compounds into mitochondria. TPP cations possess lipophilic character and therefore cross cellular membranes and accumulate into mitochondria due to the enhanced negative membrane potential of tumor mitochondria. The long alkyl chain linking honokiol to TPP moieties has two advantages: (a) it increases the lipophilic character of the compound, leading to an enhanced cellular uptake; and (b) it separates in space the bulky TPP moiety from the aromatic group of honokiol, minimizing the effect of substituents on the pharmacophore activity.

Therefore, a need exists for compounds that are effective in inhibiting tumor formation (i.e., reducing the severity or slowing the progression of symptoms of cancer) which have increased efficacy at lower doses while also mitigating resistance to chemo and radiotherapies.

Chemotherapy, drug resistance, and metabolic reprogramming. Most forms of chemotherapy (conventional antitumor agents such as doxorubicin, cis-platin, targeted therapies involving kinase inhibitors such as BRAF inhibitors) and immunotherapy using the check point inhibitors invariably induce drug resistance that renders them eventually ineffective (1). Numerous mechanisms (e.g., activation of drug efflux pumps) for drug resistance have been proposed (2). Recent reports suggest that metabolic reprogramming between a glycolytic phenotype and oxidative phosphorylation (OXPHOS) occurs during tumorigenesis or during oncogenic kinase inhibition in cancer cells (3,4). The critical dependence of cancer cells on OXPHOS or mitochondrial respiration for energy and survival suggests that cancer cell-selective and potent inhibitors of OXPHOS may be therapeutically exploited for inhibiting tumor growth, preventing or delaying resistance to kinase inhibitors (5).

Melanoma cancer. Melanoma is a very aggressive form of skin cancer accounting for the majority of skin cancer deaths. Currently, there exist no drugs for prolonged treatment of melanoma. Mutations BRAFV600E are oncogenic driver mutations in cancers. Nearly 50% of melanoma patients exhibit a BRAFV600E mutation. The existing drugs (BRAF inhibitors) provide only a short-term benefit, followed by the rapid onset of drug resistance. Metastatic melanoma is characterized as a metabolic disease. Recent research classified melanomas into two categories: a Warburg-like glycolytic type and a high OXPHOS type characterized by high peroxisome proliferator-activated receptor gamma coactivator 1-alpha (PGC-1α), the master regulator of mitochondrial biogenesis and respiration (6,7). The high OXPHOS melanoma cells are sensitive to inhibitors of OXPHOS. The glycolytic melanoma cells are sensitive to inhibitors of kinases such as vemurafenib (as are most glycolytic phenotypes to kinase inhibitors) that decreases glycolytic flux (7). However, BRAF inhibitors cause metabolic reprogramming in a subset of melanomas and induced an increase in OXPHOS.

Colon cancer. Alterations in tumor metabolism is proposed as one of the reasons for acquired drug resistance following chemotherapy of colon cancer (8). Chemotherapy induced a shift in metabolism from glycolysis to OXPHOS in human colorectal tumors. Transcriptomics analyses revealed an increased expression of SIRT1 and PGC-1α in colon cancer cells following chemotherapy (9). In addition to inducing DNA repair processes, SIRT1 deacetylates PGC-1a, leading to PGC-1α activation that is essential for enhancing mitochondrial biogenesis and function (10). Facilitation of the SIRT1/PGC-1α signaling pathway activates the OXPHOS program and oxidative energy metabolism in colon cancer cells (10). Knockdown of SIRT1 or PGC-1α expression restored the chemotherapeutic efficacy (10). The chemoresistance was attributed to the increase in OXPHOS in colon cancer cells. From a therapeutic point of view, knockdown of these transcription factors in patients is not a viable option.

Prostate cancer. Drug-induced metabolic reprogramming—shifting from glycolysis to OXPHOS—was also shown in castration-resistant prostate cancer (11). Docetaxel (Taxotere) is being used as a "standard of care" chemotherapy for patients with castration-resistant metastatic prostate cancer (12). However, prolonged treatment with docetaxel induced acquired resistance in prostate cancer patients. Docetaxel-resistant PC3 cells (PC3-DR) displayed metabolic reprogramming and consequently increased OXPHOS (11).

Leukemia. Chronic myelogenous leukemia (CML) is one of the most fatal forms of cancer in adults. Tyrosine kinases play a critical role during tumor development by promoting phosphorylation of ras-GTPase-activating protein in BCR-ABL oncogene protein (13). Imatinib (or Gleevec) inhibits phosphorylation of tyrosine kinase BCR-ABL (13). A major concern, however, with Gleevec is development of drug resistance in CML patients.

A need exists for compounds that are effective in inhibiting tumor formation (i.e., reducing the severity or slowing the progression of symptoms of cancer) which have increased efficacy at lower doses while also mitigating resistance to chemo and radiotherapies. There is an urgent need to develop a new class of OXPHOS-targeting drugs which can be used for cancer treatment, including treating drug-resistant cancers.

SUMMARY OF THE INVENTION

In one embodiment, the invention comprises a mito-honokiol compound according to the following structure:

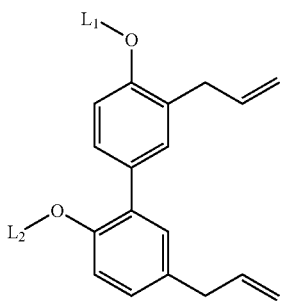

Where $L_1$ and/or $L_2$ is:

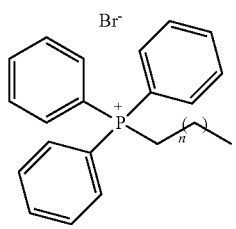

n = 1-12 where $L_1$ and $L_2$ cannot be H at the same time.

In alternate embodiments, the invention comprises a mito-honokiol compound according to the following structure:

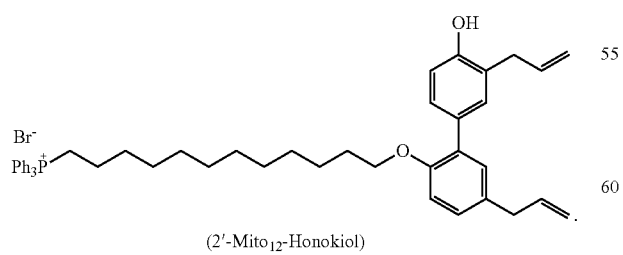

(2'-Mito$_{12}$-Honokiol)

In alternate embodiments, the invention comprises a mito-honokiol compound according to the following structure:

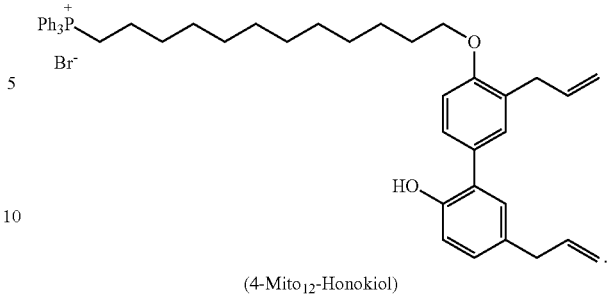

(4-Mito$_{12}$-Honokiol)

In alternate embodiments, the invention comprises a mito-honokiol compound according to the following structure:

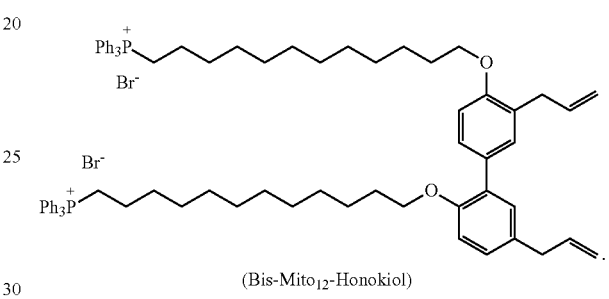

(Bis-Mito$_{12}$-Honokiol)

In alternate embodiments, the invention comprises a mito-honokiol compound according to the following structure:

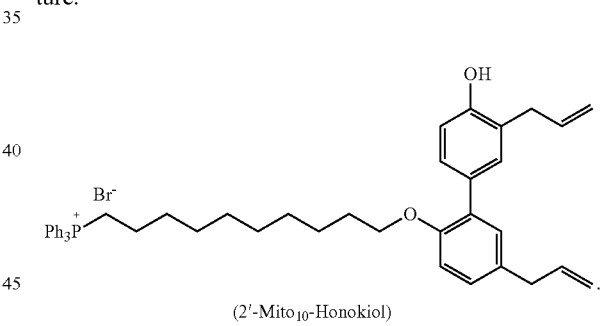

(2'-Mito$_{10}$-Honokiol)

In alternate embodiments, the invention comprises a mito-honokiol compound according to the following structure:

(4-Mito$_{10}$-Honokiol)

In alternate embodiments, the invention comprises a mito-honokiol compound according to the following structure:

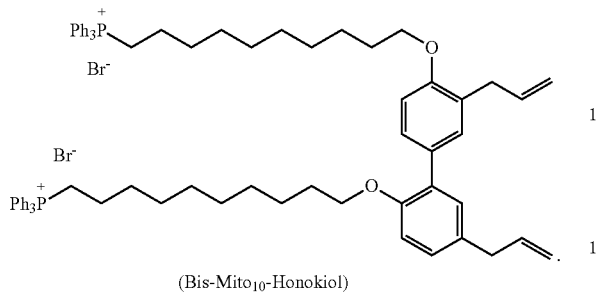

(Bis-Mito$_{10}$-Honokiol)

In alternate embodiments, the invention comprises a mito-honokiol compound according to the following structure:

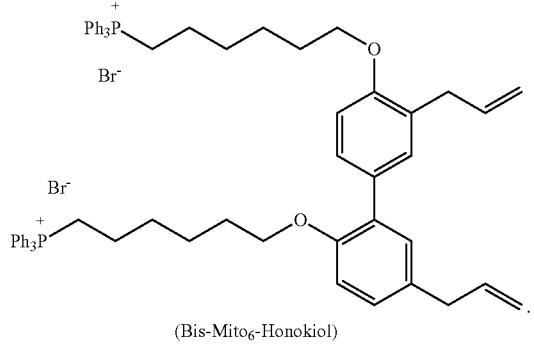

(Bis-Mito$_6$-Honokiol)

In alternate embodiments, the invention comprises a mito-honokiol compound according to the following structure:

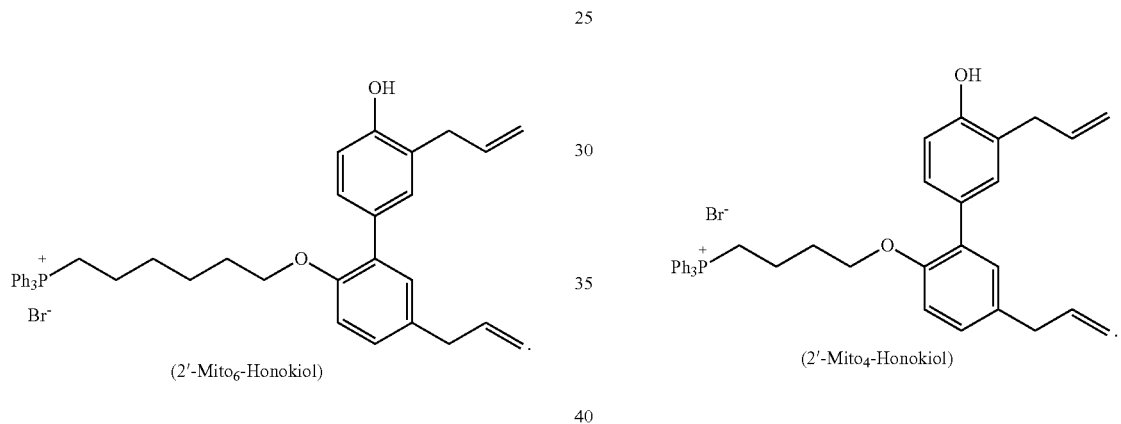

(2'-Mito$_6$-Honokiol)

(2'-Mito$_4$-Honokiol)

In alternate embodiments, the invention comprises a mito-honokiol compound according to the following structure:

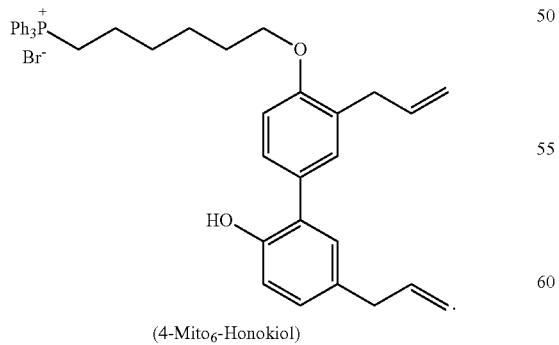

(4-Mito$_6$-Honokiol)

In alternate embodiments, the invention comprises a mito-honokiol compound according to the following structure:

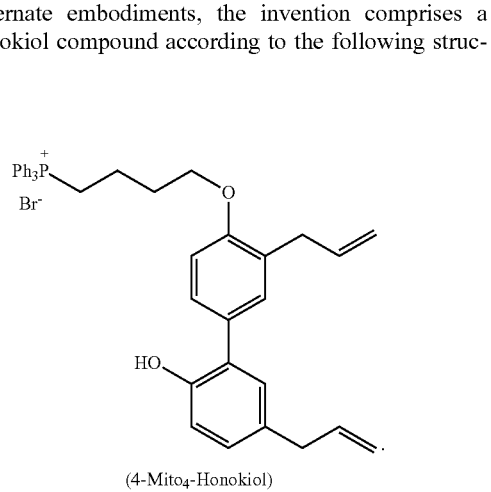

(4-Mito$_4$-Honokiol)

In alternate embodiments, the invention comprises a mito-honokiol compound according to the following structure:

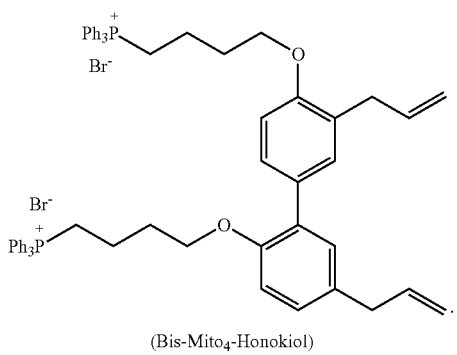

(Bis-Mito₄-Honokiol)

In alternate embodiments, the invention comprises a mito-honokiol compound according to the following structure:

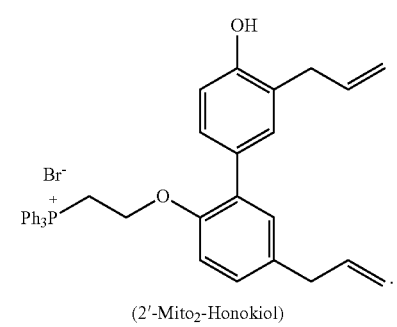

(2′-Mito₂-Honokiol)

In alternate embodiments, the invention comprises a mito-honokiol compound according to the following structure:

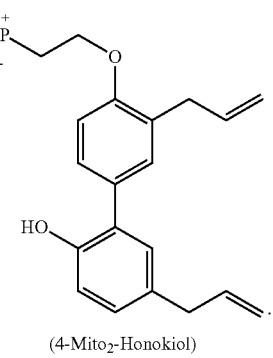

(4-Mito₂-Honokiol)

In alternate embodiments, the invention comprises a mito-honokiol compound according to the following structure:

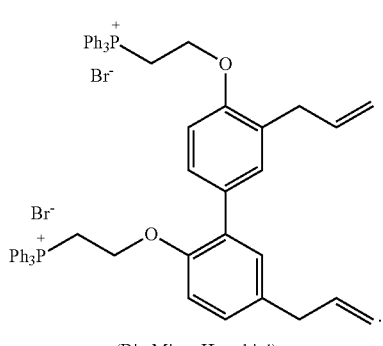

(Bis-Mito₂-Honokiol)

In alternate embodiments, the invention comprises a mito-honokiol compound according to the following structure:

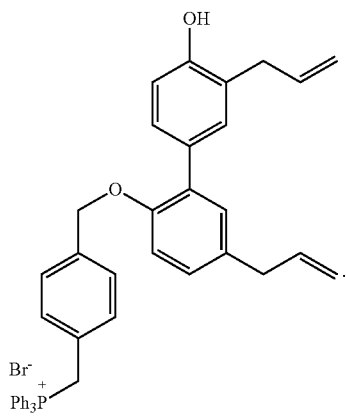

(2′-Mito$_{phen}$-Honokiol)

In alternate embodiments, the invention comprises a mito-honokiol compound according to the following structure:

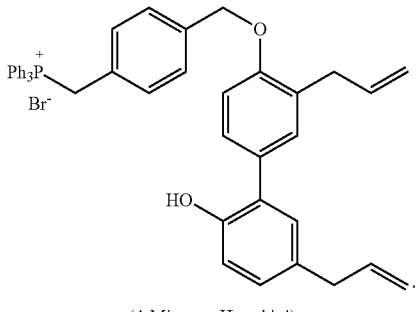

(4-Mito$_{phen}$-Honokiol)

In alternate embodiments, the invention comprises a mito-honokiol compound according to the following structure:

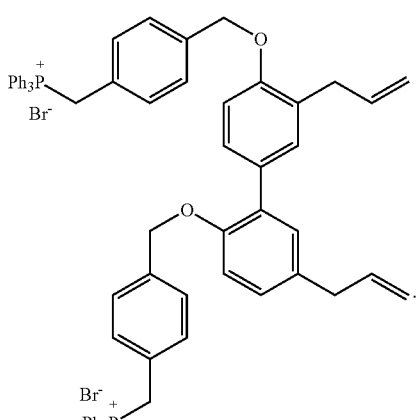

(Bis-Mito*phen*-Honokiol)

In an alternate embodiments, the invention comprises mitochondria-targeted honokiol derivatives

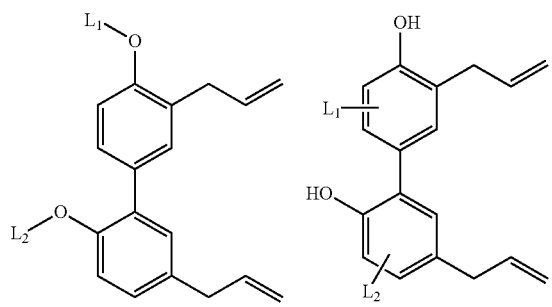

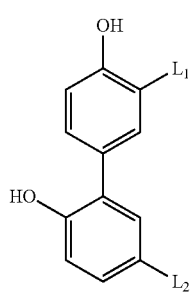

where $L_1$ and/or $L_2$ are comprised of organic linker attached to triphenylphosphonium moiety In some embodiments, $L_1$ and/or $L_2$ comprise an organic linker comprising about 1-15 carbons, preferably about 1-12 carbons, attached to the triphenylphosphonium moiety.

In an alternate embodiments, the invention comprises mitochondria-targeted magnolol derivatives

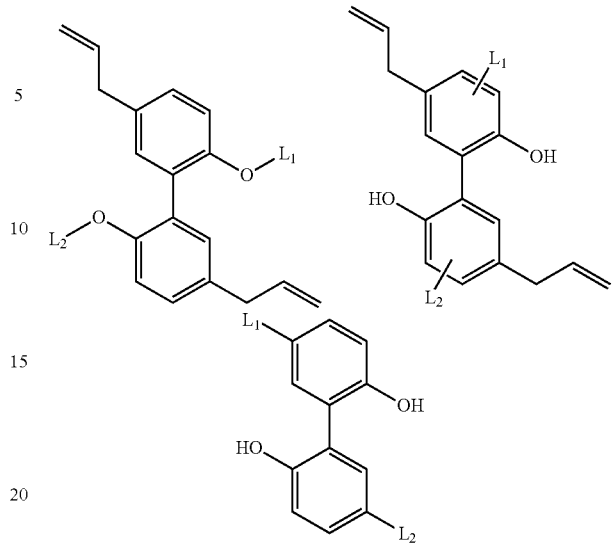

where $L_1$ and/or $L_2$ are comprised of organic linker attached to triphenylphosphonium moiety In some embodiments, $L_1$ and/or $L_2$ comprise an organic linker comprising about 1-15 carbons, preferably about 1-12 carbons, attached to the triphenylphosphonium moiety.

In alternate embodiments, the invention also comprises a method of inhibiting tumor formation in a subject comprising administering to the subject a therapeutically effective amount of a composition comprising at least one mito-honokiol compound as described above.

In an alternate embodiment, the invention comprises a method of protecting healthy cells in a subject having cancer. The method comprises administering to the subject a therapeutically effective amount of a composition comprising at least one mito-honokiol compound as described above. This neuroprotective effect of the mito-honokiol compounds of the presently claimed invention can be used in combination with other cancer treatments.

In alternate embodiments, the invention comprises a kit comprising at least one mito-honokiol compound as described above, a pharmaceutically acceptable carrier or diluent, and instructional material.

In a further embodiment, the disclosure provides a composition comprising the mito-magnolol compound described herein and a pharmaceutically acceptable carrier.

In yet another embodiment, the disclosure provides a method of treating cancer in a subject having cancer comprising administering the mito-magnolol compound or composition described herein in a therapeutically effective amount to treat the cancer.

In yet another embodiment, the disclosure provides a method of reducing or inhibiting cancer cell growth in a subject having cancer, the method comprising administering the mito-magnolol compound or composition described herein in a therapeutically effective amount to reduce or inhibit cancer cell growth.

In yet another aspect, the present disclosure provides a method of preventing or delaying resistance of a cancer to an anti-cancer therapy in a subject, the method comprising administering the mito-magnolol compound or composition described herein in a therapeutically effective amount to prevent or delay resistance of the cancer to the anti-cancer therapy.

In yet a further aspect, the disclosure provides a method of increasing a T cell response to an anti-cancer therapy in a cancer patient, the method comprising administering the mito-magnolol compound described herein in a therapeutically effective amount to increase the T cell response to the anti-cancer therapy.

In yet another aspect, the disclosure provides a kit comprising at least one mito-magnolol compound described herein, a pharmaceutically acceptable carrier or diluent, and instructional material.

Other features of the present invention will become apparent after review of the specification, claims and drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 9A-9E. Role of STAT3 in mediating mito-honokiol's anti-cancer effects. (A) The PathScan receptor tyrosine kinase assay indicated that Mito-HNK inhibits STAT3 phosphorylation levels without affecting EGFR phosphorylation in DMS-273 cell line. (B) Effects of Mito-HNK in STAT3 phosphorylation were further validated via a Western blot assay. Both cytoplasmic and mitochondrial STAT3 phosphorylation were downregulated by Mito-HNK in both DMS-273 and H446 cell lines. (C) Knock down of endogenous STAT3 gene via the shRNA approach was confirmed by a Western blot analysis. (D) The STAT3 knockdown in DMS-273 cells significantly inhibits the proliferation of DMS-273 cells and abrogated the antiproliferative effects of both HNK and Mito-HNK. (E) Mito-HNK does not show significant inhibitory effects on the proliferation of NHBE (normal lung epithelial cells) compared to DMS-273 SCLC cells.

FIG. 10A-10C. Effects of mito-honokiol in EGFR TKI drug-resistant lung cancer cells. (A) Effects of Mito-HNK in EGFR TKI drug-resistant lung cancer cells, AR1, AR2, and AR3, and EGFR TKI drug-sensitive lung cancer cells H1975 were examined. Mito-HNK significantly inhibits the proliferation of both EGFR TKI drug-sensitive and EGFR TKI drug-resistant lung cancer cells compared to cells treated with control DMSO. (B) Both EGFR TKI drug-sensitive and EGFR TKI drug-resistant lung cancer cells were sensitive to HNK and Mito-HNK, but Mito-HNK showed about 100-fold potency in the inhibition of both EGFR TKI drug-sensitive and EGFR TKI drug-resistant lung cancer cell lines.

FIG. 11A-11C. Mito-honokiol exhibits potent anti-cancer effects in NSLC or SCLC orthotopic lung cancer models. DM273 cells ($1\times10^6$ cells/50 μg of growth factor reduced Matrigel in 50 μL of RPMI-1640 medium) were injected into the left lung. One week after injection, mice were treated with the same dose of HNK or Mito-HNK (7.5 μmol/kg) or vehicle (corn oil) by oral gavage five times per week for three weeks). Representative images of bioluminescence are shown for H2030 injected mice (11A) and DMS273 injected mice (11C). While HNK did not significantly reduce tumor growth, Mito-HNK at the same dose reduced tumor size by 70% as compared to control mice (FIG. 11B).

FIG. 12A-12E. Mito-honokiol inhibits both NSCLC and SCLC brain metastasis in Nod/Scid mice. (A) Representative images of an ultrasound guided left ventricle injection for lung cancer brain metastasis models. (B) Representative luciferase, GFP, and H&E IHC images from the gavage control group and HNK- or Mito-HNK-treated group mice. (C) Quantification of bioluminescence imaging signal intensity in the control group and HNK-treated group at different time points after injection of H2030-BrM3 cells. Quantified values are shown in total flux. (D) Corresponding grayscale photographs and color luciferase images of DMS273-injected mice. Images are superimposed and analyzed with Living Image software (Xenogen Corporation). Data are expressed as normalized photon flux (photons/s/cm$^2$). (E) Graph depicting the quantification of bioluminescence imaging signal intensity for the control group and HNK- and Mito-HNK-treated groups at different time points after injection of DMS273 cells.

FIG. 15A-15F. Effects of mito-honokiol alone or in combination with 2-deoxyglucose on pancreatic cells. At submicromolar concentration (0.2 µM) both isomers of Mito-HNK-C$_{10}$ inhibit proliferation of MiaPaCa-2 cells (pancreatic cancer cell line) (FIG. 15A). Mito-magnolol (1 µM) and isomers of mito-honokiol-C$_4$ also exhibit antiproliferative effects (FIG. 15B). Further, the combining the mito-honokiols of the present invention with antiglycolytic agents (e.g. 2-deoxyglucose) reduced the rate of proliferation of pancreatic cancer cells than either treatment alone, as shown for a number of different concentrations in FIG. 15C-F.

FIGS. 17A and 17B show the effects of the combination of mito-honokiols with 2-deoxyglucose on viability (total ATP) in Capan-2 cells (pancreatic adenocarcinoma cell line).

FIG. 21A-21F demonstrates the effects of PLX4720 on proliferation of wild type UACC-62-WT cells and UACC-62 resistant to PLX4720 (UACC-62-R) cells. UACC-62-WT cells (A) or UACC-62-R cells (B) were treated with PLX4720 as indicated. Cell proliferation was monitored in real time with the continuous presence of indicated treatments until the end of each experiment. (C) Representative images shown are the segmentation of phase contrast images (segmentation mask illustrated in black). (D) The cell confluence (as control groups reach 95% confluency) is plotted against concentration of PLX4720 inhibitor. Dashed lines represent the fitting curves used to determine the IC$_{50}$ values. (E) A two-dimensional map shows the bioenergetics in WT (■) and kinase inhibitor resistant (○) cells treated with vehicle (black) or Mito-MGN (blue). (F) The effect of Mito-MGN (0.2 µM) on mitochondrial complex I and II activities (oxygen consumption rate, OCR) is shown for wild-type (red) and resistant UACC-62 (blue) melanoma cells.

FIG. 29A-29B shows schemes for synthesis of Mito-magnolol and Mito$_{Me}$-magnolol. (A) Synthesis of Mito-magnolol. Reagents and conditions: i, K$_2$CO$_3$, DMF, 40° C., 35%. (B) Synthesis of Mito$_{Me}$-magnolol. Reagents and conditions: i, CH$_3$I, DMF, 6 h, K$_2$CO$_3$, 35° C., 64%. ii, K$_2$CO$_3$, DMF, 40° C., 60%. 2-O-Me-MGN is 2-O-methyl-magnolol.

DETAILED DESCRIPTION OF THE INVENTION

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

Figure 1:
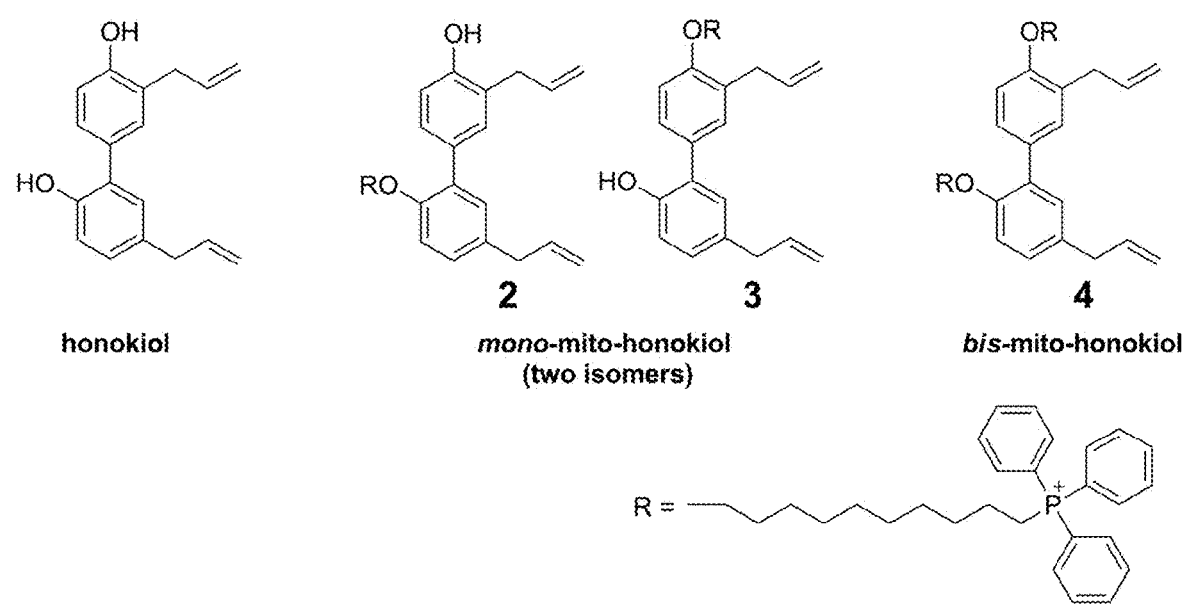
FIG. 1. Chemical structures of honokiol, and its mitochondria-targeted analogs. R=triphenylphosphonium (TPP) with an 10 carbon alkyl linker.
Figure 2:
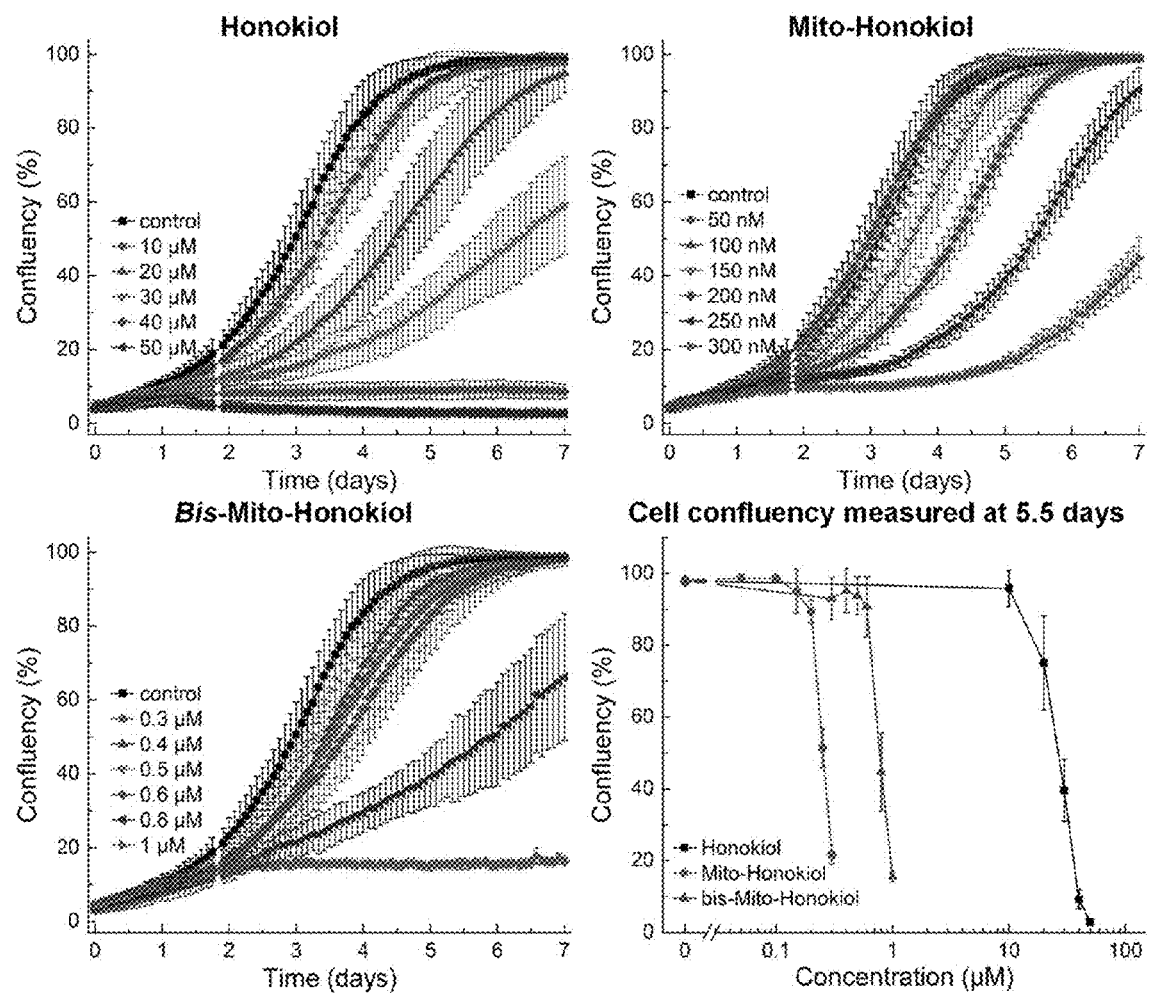
FIG. 2. Antiproliferative effects of honokiol and mito-honokiol. H2030 lung cancer cells were treated with micromolar levels of honokiol and nanomolar concentrations of mito-honokiol. Cell growth was continuously monitored. Changes in confluency were used as a surrogate marker of cell proliferation. After 5 days of incubation of H2030 cells with varying concentrations of honokiol and mito-honokiol, the confluency was plotted as a function of concentration.

The Invention. In one embodiment, the present invention provides novel mito-honokiol compounds modified to selectively and synergistically inhibit cancer proliferation and progression. Specifically, the inventors have shown that linking triphenylphosphonium (TPP) to honokiol (and it's structural isomers, including magnolol) via long alkyl chains yields a novel mito-honokiol compound which is 100-1000 fold more potent than honokiol, while also exhibiting substantial inhibitory activity at nanomolar concentrations in vitro. The compound comprises mono- and bis-substituted mito-honokiol molecules (FIG. 1).

The mito-honokiol compounds of the present invention are prepared by chemically linking triphenylphosphonium (TPP) to honokiol, via long alkyl chains.

Compounds, Compositions and Synthesis

Tri-phenyl-phosphonium (TPP$^+$)-conjugated mitochondria-targeted agents, including mito-magnolol described herein are potent and selective inhibitors of OXPHOS in tumor cells (14-17). Compared to their untargeted analogs, the TPP$^+$-conjugated analogs are typically more potent, for example about 100 to 1,000 times more potent in inhibiting tumor cell proliferation. In addition, TPP$^+$-containing analogs lack the toxicity associated with usual mitochondrial OXPHOS inhibitors (e.g., rotenone, cyanide), exhibiting a high therapeutic index and limited off-target effects. Conventional inhibitors of mitochondrial electron transport chain complexes such as cyanide, oligomycin, 2,4-dinitrophenol, are not specific for cancer cell mitochondria, and these all have a low therapeutic index. Biguanides (e.g., metformin) exhibit antitumor effects, and a proposed mechanism involves targeting mitochondrial OXPHOS, albeit weakly. Metformin efficacy is further limited by transport requiring the presence of organic cation transporters (OCT).

In contrast, the newly developed mitochondria targeted agents (MTAs) described herein consist of the TPP$^+$ moiety conjugated to an organic molecule (magnolol) via an aliphatic side chain. MTAs are targeted to mitochondria, driven by the presence of an increased negative mitochondrial membrane potential in cancer cells (18,19). MTAs are lipophilic and cationic, and diffuse across the cell membrane. The presence of OCT is not required for efficient intracellular accumulation of MTAs.

The present disclosure provides mito-magnolol compounds (e.g., Mito-MGN), a mitochondria-targeted derivative of the naturally occurring bioactive polyphenolic molecule, magnolol. Magnolol is the most abundant bioactive component of *magnolia* extract, a traditional herbal formula used effectively for centuries in East Asia for treating multiple diseases (32). One advantage of magnolol is its ability to be modified into a single monosubstituted isomer that is easily separated and purified, enabling synthesis of large quantities of Mito-magnolol.

In one embodiment, the present disclosure provides novel mito-magnolol compounds modified to selectively and synergistically inhibit cancer proliferation and progression. Specifically, the inventors have shown that linking triphenylphosphonium (TPP) to magnolol via long alkyl chains yields a novel mito-magnolol compound which can treat cancer, including chemotherapeutic resistant cancers. The compound comprises mono- and bis-substituted mito-magnolol molecules.

In one embodiment, the disclosure provides a mito-magnolol compound of formula (I)

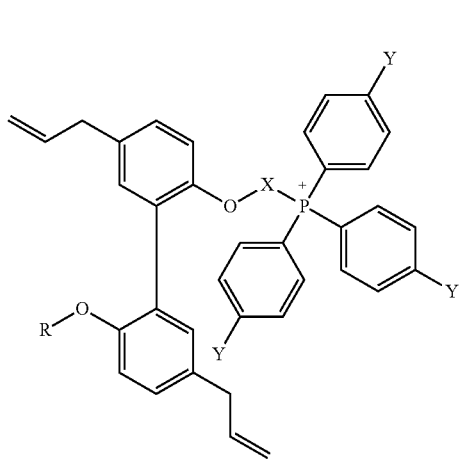

wherein
- X is selected from a $C_1$-$C_{18}$ alkyl, phenyl and polyethylene glycol (PEG) or using other linkers (e.g., benzyl, ramification of the alkyl side chain, double bound, etc.);
- each Y is independently selected from —H, —$CF_3$, methyl (Me), Cl, and OMe, $C(O)CH_3$, $NO_2$, $N(Me)_2$; and R is selected from H, alkyl chain ($C_nH_{2n+1}$, n=1-18), phenyl, benzyl, and polyethylene glycol (PEG).

For Example, the mito-magnolol compound can be

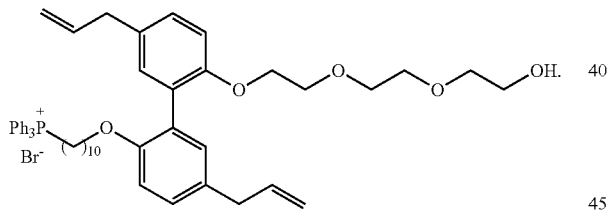

In another example, the mito-magnolol compound can be

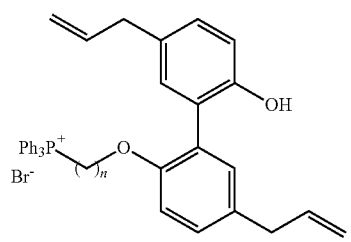

wherein n is an integer selected from 1-18. In another embodiment, n is an integer selected from 6-12.

In a preferred example, the mito-magnolol of formula (I) comprises X is $C_1$-$C_{18}$ alkyl, each Y is H and R is H.

In one embodiment, the mito-magnolol is:

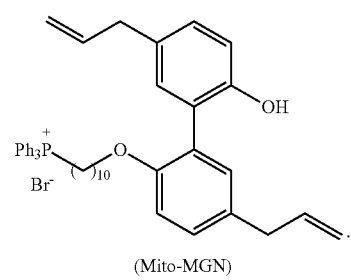

(Mito-MGN)

Another embodiment provides a mito-magnolol compound of:

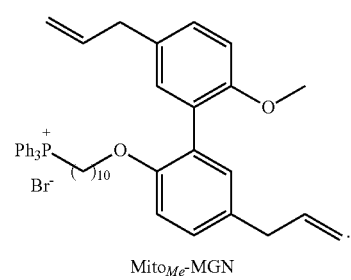

Mito$_{Me}$-MGN

Other structures are as follows:

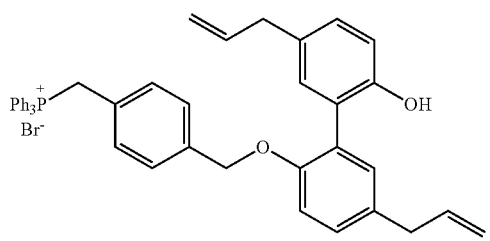

MitoPhen-MGN

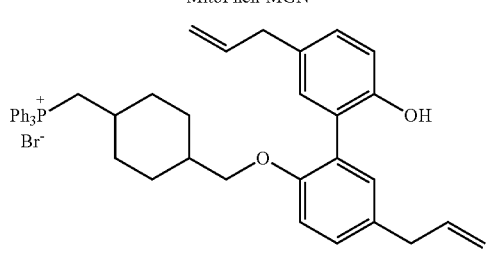

MitoCy-MGN

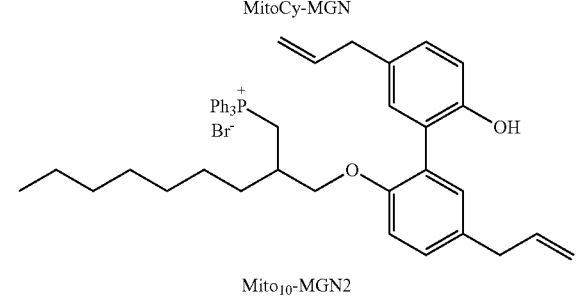

Mito$_{10}$-MGN2

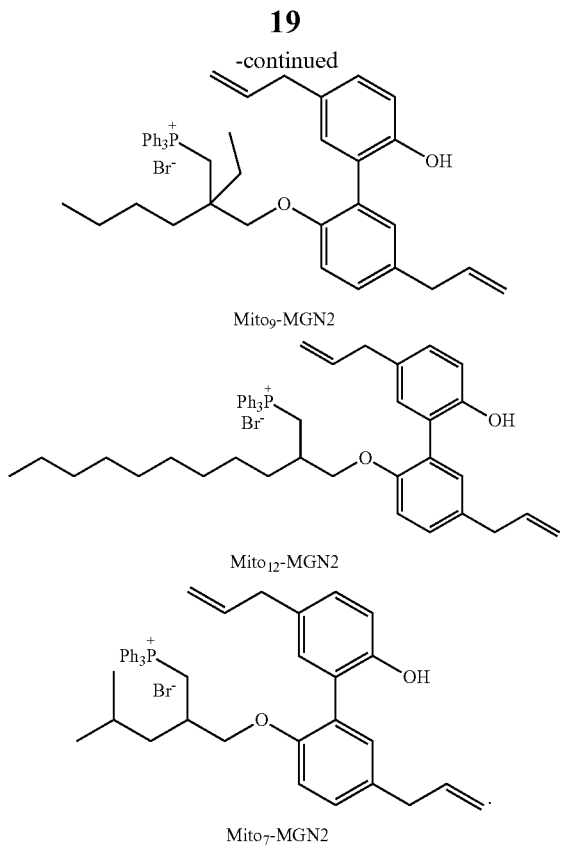

Mito₉-MGN2

Mito₁₂-MGN2

Mito₇-MGN2

In another embodiment, the mito-magnolol compound is formula (II)

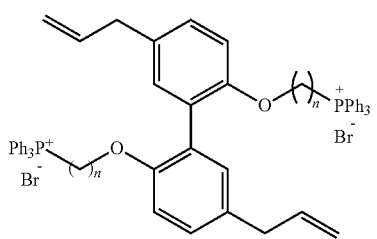

(II)

wherein each n is selected independently from an integer from 1-18.

In one embodiment, the mito-magnolol of formula (II) is

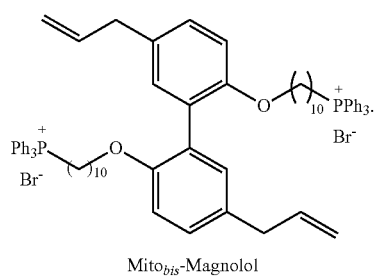

Mito$_{bis}$-Magnolol

The present disclosure also provides composition comprising the mito-magnolol compound described herein and a pharmaceutically acceptable carrier. A "pharmaceutically acceptable carrier" means any conventional pharmaceutically acceptable carrier, vehicle, or excipient that is used in the art for production and administration of compositions to a subject. Pharmaceutically acceptable carriers are typically non-toxic, inert, solid or liquid carriers which are physiologically balanced. Typically, phosphate buffered saline or other saline solutions are physiologically acceptable carriers. A pharmaceutically acceptable carrier can be selected on the basis of the selected route of administration and standard pharmaceutical practice. The compounds may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa., which is incorporated by reference in its entirety. Suitable dosage forms may comprise, but are not limited to, for example, solutions, parenteral solutions, injectable solutions, troches, suppositories, or suspensions.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents, absorbents or lubricating agents. Additional oral administration forms are contemplated, including, but not limited to, elixirs, liquids, solutions, suspensions, emulsions, multi-layer tablets, soft gelatin capsules, hard gelatin capsules, troches, lozenges, beads, granules, particles, microparticles, dispensible granules, cachets, among others. Formulations of the present technology suitable for oral administration can be presented as discrete units, such as capsules, caplets or tablets. These oral formulations also can comprise a solution or a suspension in an aqueous liquid or a non-aqueous liquid. The formulation can be an emulsion, such as an oil-in-water liquid emulsion or a water-in-oil liquid emulsion. The oils can be administered by adding the purified and sterilized liquids to a prepared enteral formula, which can then be placed in the feeding tube of a patient who is unable to swallow. Another oral administration may be the formation of a liquid or gel suitable for oral dosage. In one embodiment, the compounds may be formulated in water, juice, or other beverage for oral consumption.

For parenteral administration, the active agent may be mixed with a suitable carrier or diluent such as water, an oil (e.g., a vegetable oil), ethanol, saline solution (e.g., phosphate buffer saline or saline), aqueous dextrose (glucose) and related sugar solutions, glycerol, or a glycol such as propylene glycol or polyethylene glycol. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propylparaben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component. The unit dosage form can be a packaged preparation, the package containing discrete quantities of preparation, such as packeted tablets, capsules, and powders in vials, or ampoules. Also, the unit dosage form can be a capsule, tablet, cachet, or lozenge itself, or it can be the appropriate number of any of these in packaged form.

Figure 13:
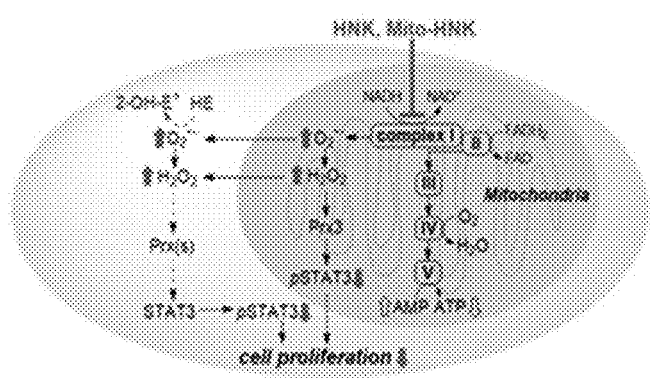
FIG. 13. Proposed mito-honokiol action mechanisms. Mito-HNK inhibits complex I, stimulates ROS, oxidizes peroxiredoxins, and blocks STAT3 phosphorylation, leading to inhibition of cell proliferation. Changes due to the treatment are shown by red block arrows. HE conversion to 2-OH-E$^+$ is used for specific detection of superoxide.

Methods of synthesizing the mito-magnolols of the present disclosure are shown in FIGS. 13A and 13B, and described in the Examples below. Briefly, mito-magnolol was prepared by reacting 10-bromodecyltriphenylphosphonium bromide with magnolol in the presence of potassium carbonate in DMF (FIG. 30A). To a mixture of magnolol (0.2 g, 0.75 mmol) and anhydrous potassium carbonate (0.22 g, 1.5 mmol) in DMF (20 mL) was added 10-bromodecyltriphenylphosphonium bromide (0.42 g, 0.75 mmol) at 0° C. The mixture was stirred at 35° C. for 24 hours. The residue was taken up into water and extracted with $CH_2Cl_2$. The organic layer was dried over $Na_2SO_4$, and the solvent was removed under reduced pressure. Ether was added to precipitate the crude product. Purification by flash chromatography using the following gradient from $CH_2Cl_2$ (100%) to $CH_2Cl_2$/EtOH (80/20) as eluent delivered the corresponding Mito-magnolol (200 mg, 35% yield) and the Mito-bis-magnolol (80 mg, 14% yield) as white solids.

Me-magnolol and DiMe-magnolol were prepared by reacting methyl iodide with magnolol in the presence of potassium carbonate in DMF. Williamson reaction of 2-O-methylmagnolol and 10-bromodecyltriphenylphosphonium bromide in the presence of potassium carbonate led to $Mito_{Me}$-magnolol (FIG. 30B). One skilled in the art is able to modify these methods to produce other mito-magnolols contemplated herein.

Methods of Use.

In one embodiment, the invention provides a method of treating cancer in a subject comprising administering to the subject a therapeutically effective amount of a composition comprising at least one mito-honokiol or mito-magnolol compound of the present invention. In one embodiment, the composition comprises one mito-honokiol compound or mito-magnolol of the present invention, but in alternate embodiments, multiple mito-honokiol or mito-magnolol compounds of the invention may be administered.

In use, the mito-honokiol compounds of the present invention are more cytotoxic to cancer cells than to non-cancerous cells. The inventors have demonstrated that the mito-honokiol compounds of the present invention potently inhibit tumor cell proliferation and induce cytotoxicity by selectively inhibiting tumor, but not normal, cells.

The antiproliferative activity of the newly-synthesized honokiol analogs were tested using H2030 lung cancer cells and compared with the activity of the parent compound, honokiol (FIG. 1). The results indicate that substitution of honokiol with TPP increases the antiproliferative activity of the compound in vitro in the cellular model of lung cancer. Mitochondrial targeting of mito-honokiol led to improved antiproliferative activity at significantly lower doses (at least 100-fold) than required for the parent compound, honokiol.

Figure 3:
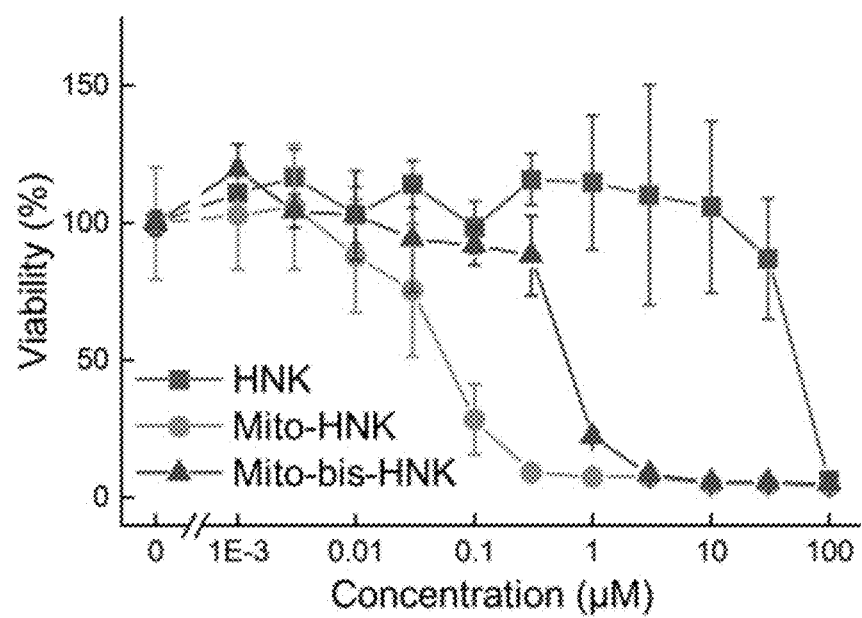
FIG. 3. Comparison of anti-proliferative effects of honokiol (HNK), mito-honokiol (Mito-HNK) and bis-mito-honokiol (Mito-bis-HNK) on human MiaPaCa-2 pancreatic cancer cells. The results indicate that substitution of honokiol with TPP significantly increases the antiproliferative activity of the compounds in an in vitro cellular model of pancreatic cancer. Mitochondrial targeting of honokiol leads to improved antiproliferative activity of honokiol at significantly lower doses (~1000-fold) than required for honokiol.

The inventors also compared the antiproliferative activity of mito-honokiol analogs to honokiol using human MiaPaCa-2 pancreatic cancer cells (FIG. 3). Their results indicate that substitution of honokiol with TPP significantly increases the antiproliferative activity of the compounds in a cellular model of pancreatic cancer. Results indicate that substitution of honokiol with triphenylphosphonium moiety(ies) significantly increases the antiproliferative activity of the compounds in cellular model of pancreatic cancer. Additionally, bis-mito-honokiol, a double substituted compound is also more potent than honokiol. Mitochondrial targeting of honokiol led to improved antiproliferative activity of honokiol at significantly lower doses (ca. 1000-fold) than required for the parent compound, honokiol. Ongoing studies indicated that aerosolized mito-honokiol inhibits lung cancer metastasis to the brain in an orthotopic model of lung cancer in mice.

The antiproliferative and antitumor mechanism of action of honokiols has been attributed by some to an effect on mitochondria that involves reactive oxygen species (inhibition or generation), or the antioxidant properties of honokiols. Interestingly, the inventors have found that, although the antioxidant properties of honokiols are removed by attachment of TPP (i.e., their mito-honokiols), the resulting compounds are still very potent inhibitors of proliferation. Thus, the mito-honokiols appear to target mitochondria selectively in tumor cells, and induce antiproliferative signaling events via a mechanism unrelated to conventional antioxidant mechanisms.

The invention also provides therapeutic compositions comprising at least one of the mito-honokiol compounds of the present invention and a pharmacologically acceptable excipient or carrier. The therapeutic composition may advantageously be soluble in an aqueous solution at a physiologically acceptable pH.

In one embodiment, the mito-honokiol compounds of the present invention provide effective methods of treating cancer. In one embodiment, the mito-honokiol compounds of the present invention potently inhibit tumor formation. In some embodiments, the cancer is a primary tumor. In some embodiments, the cancer is a metastatic cancer. In one embodiment, the mito-honokiol compounds of the present invention inhibit, reduce or prevent metastasis.

The term "metastasis," "metastatic tumor" or "secondary tumor" refers to cancer cells that have spread to a secondary site, e.g., outside of the primary tumor tissue. Secondary sites include, but are not limited to, the lymphatic system, skin, distant organs (e.g., liver, stomach, pancreas, brain, etc.) and the like. In some embodiments, the mito-honokiol compounds of the present invention provide methods of treating a primary or secondary tumor.

The compounds of the present invention also provide a neuroprotective effect to non-cancerous cells. Specifically, the mito-honokiol compounds of the present invention can be combined with existing treatments to protect non-cancerous cells in a subject.

Figure 4:
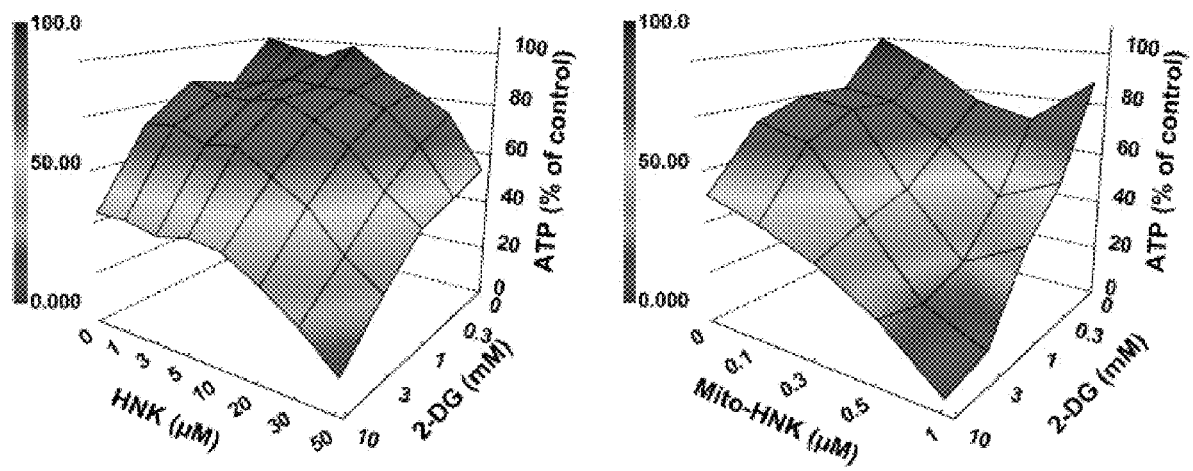
FIG. 4. Synergistic depletion of intracellular ATP in MiaPaCa-2 cells by combination of 2-deoxyglucose (2-DG) and honokiol (HNK) and mito-honokiol (Mito-HNK). The data were obtained on the human pancreatic cancer MiaPaCa-2 cell line. Honokiol and mito-honokiol synergize with the anti-glycolytic agent 2-deoxyglucose (2-DG) to cause a decrease in cellular ATP levels, however, mito-honokiol was needed at significantly lower concentrations than honokiol to deplete cellular ATP when combined 2-DG.
Figures 17A, 17B:
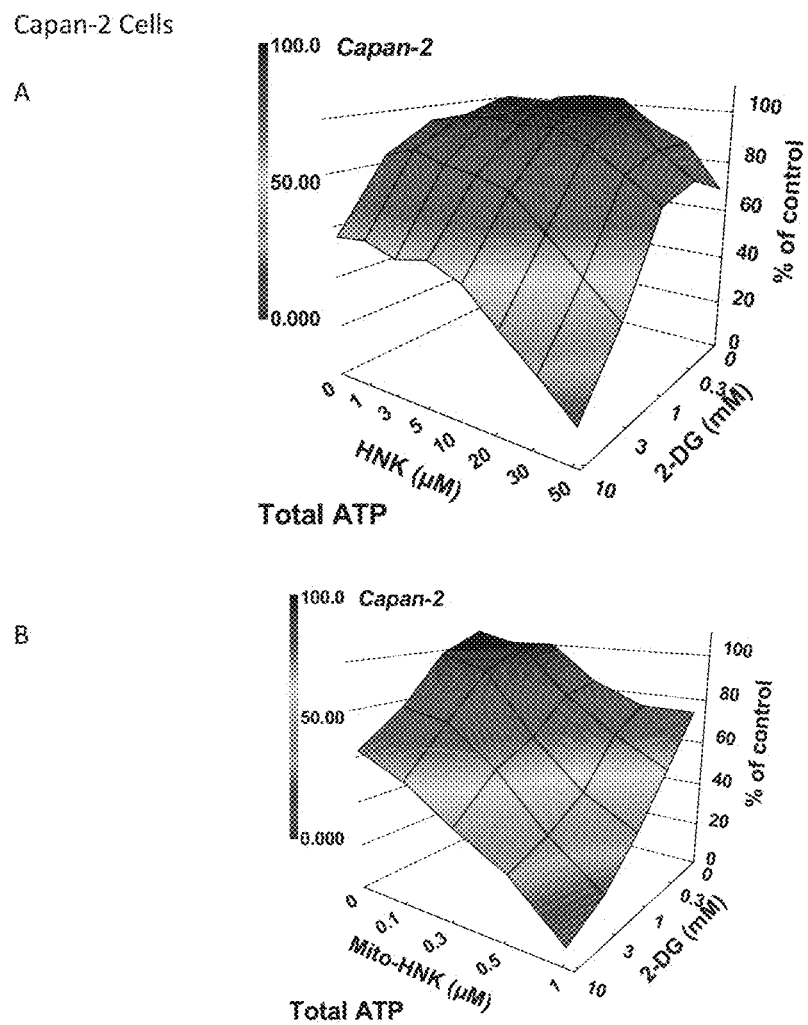
FIG. 17A-17B. Effects of the combination of mito-honokiols with 2-deoxyglucose.

In one embodiment, the mito-honokiols of the present invention may be also used in combination with standard-of-care chemotherapeutics or with ionizing radiation to treat resistant cancer cells. Combining the mito-honokiols of the present invention with antiglycolytic agents (e.g. 2-deoxyglucose, 3-bromopyruvate) and other standard-of-care drugs (e.g. gemcitabine) on the rate of proliferation of pancreatic cancer cells, showed impressive results. Specifically, when tested on MiaPaCa-2 cell line (FIG. 4) both honokiol and mito-honokiol synergize with 2-deoxyglucose (2-DG) in decreasing cellular ATP levels. Notably, mito-honokiol was needed at significantly lower concentrations than honokiol to deplete cellular ATP, when combined with the antiglycolytic agent used. Similarly, treatment with mito-honokiol sensitized the low-glycolytic, 2-DG-resistant pancreatic cancer cell line, Capan-2, to 2-DG, resulting in a significant loss of cellular ATP (FIG. 17A-B).

The compounds and compositions of the present disclosure may be used for methods of treating cancer, including methods of overcoming resistance to chemotherapies, for example, overcoming resistance to oncogene-targeted therapies or checkpoint inhibitors. The compounds and compositions comprising mito-magnolols act as potent OXPHOS inhibitors, which can be used alone or in combination with other anti-cancer therapies, including chemotherapeutic agents, to treat cancer, including drug-resistant cancer (e.g., drug resistant-melanoma), in a subject in need thereof.

In one embodiment, the disclosure provides methods of treating cancer, including treatment of cancers associated with increases levels of OXPHOS. In one embodiment, the TPP$^+$-conjugated mitochondria-targeted mito-magnolols selectively localize within the more negative mitochondria of cancer cells and are potent and selective inhibitors of OXPHOS in cancer cells, including, but not limited to melanoma, breast, colon, lung, and pancreas cancer cells. As demonstrated in the examples, mito-magnolol potently inhibits OXPHOS and tumor cell proliferation in drug resistant melanoma.

In one embodiment, the mito-magnolol compounds of the present invention provide effective methods of treating cancer. In one embodiment, the mito-magnolol compounds potently inhibit tumor formation. In some embodiments, the cancer is a primary tumor. In some embodiments, the cancer is a metastatic cancer. In one embodiment, the mito-magnolol compounds or compositions described herein reduce or prevent metastasis. In another embodiment, the mito-magnolol compounds are able to treat or inhibit anti-cancer (e.g., chemotherapeutic) or drug resistant cancer, for example, drug resistant melanoma.

By "cancer" or "tumor" we mean any abnormal proliferation of tissues, including solid and non-solid tumors. For instance, the composition and methods of the present invention can be utilized to treat cancers that manifest solid tumors such as skin cancer including melanoma, pancreatic cancer, breast cancer, colon cancer, lung cancer, prostate cancer, thyroid cancer, ovarian cancer, skin cancer, and the like. The composition and methods of the present invention can also be utilized to treat non-solid tumor cancers such as non-Hodgkin's lymphoma, leukemia and the like.

The term "metastasis," "metastatic tumor" or "secondary tumor" refers to cancer cells that have spread to a secondary site, e.g., outside of the primary tumor tissue. Secondary sites include, but are not limited to, the lymphatic system, skin, distant organs (e.g., liver, stomach, pancreas, brain, etc.) and the like. In some embodiments, the mito-magnolol compounds provide methods of treating a primary or secondary tumor.

By "subject" we mean mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, fish and the like. The term "subject" does not denote a particular age or sex. In a preferred embodiment, the subject is a human.

By "treating" we mean the management and care of a subject for the purpose of combating the disease, condition, or disorder. The terms embrace preventative, i.e., prophylactic, and palliative treatments. Treating includes the administration of a compound of the present invention to prevent, ameliorate and/or improve the onset of the symptoms or complications, alleviating the symptoms or complications, or eliminating the disease, condition, or disorder. For example, treating cancer in a subject includes the reducing, repressing, delaying or preventing tumor growth, reduction of tumor volume, and/or preventing, repressing, delaying or reducing metastasis of the tumor. Treating cancer in a subject also includes the reduction of the number of tumor cells within the subject. The term "treatment" can be characterized by at least one of the following: (a) the reducing, slowing or inhibiting the growth of cancer and cancer cells, including slowing or inhibiting the growth of metastatic cancer cells; (b) preventing the further growth of tumors; (c) reducing or preventing the metastasis of cancer cells within a subject; and (d) reducing or ameliorating at least one symptom of cancer. In some embodiments, the optimum effective amount can be readily determined by one skilled in the art using routine experimentation.

By "ameliorate", "amelioration", "improvement" or the like we mean a detectable improvement or a detectable change consistent with improvement occurs in a subject or in at least a minority of subjects, e.g., in at least about 2%, 5%, 10%, 15%, 20%, 25%, 30%, 40%, 50%, 60%, 70%, 75%, 80%, 85%, 90%, 95%, 98%, 100% or in a range about between any two of these values. Such improvement or change may be observed in treated subjects as compared to subjects not treated with the mito-honokiol or mito-magnolol compounds of the present invention, where the untreated subjects have, or are subject to developing, the same or similar disease, condition, symptom or the like. Amelioration of a disease, condition, symptom or assay parameter may be determined subjectively or objectively, e.g., self assessment by a subject(s), by a clinician's assessment or by conducting an appropriate assay or measurement, including, e.g., a quality of life assessment, a slowed progression of a disease(s) or condition(s), a reduced severity of a disease(s) or condition(s), or a suitable assay(s) for the level or activity(ies) of a biomolecule(s), cell(s) or by detection of cell migration within a subject. Amelioration may be transient, prolonged or permanent or it may be variable at relevant times during or after the mito-honokiol compounds of the present invention is administered to a subject or is used in an assay or other method described herein or a cited reference, e.g., within about 1 hour of the administration or use of the mito-honokiol compounds of the present invention to about 3, 6, 9 months or more after a subject(s) has received the mito-honokiol or mito-magnolol compounds of the present invention.

By "modulation" of, e.g., a symptom, level or biological activity of a molecule, replication of a pathogen, cellular response, cellular activity or the like means that the cell level or activity is detectably increased or decreased. Such increase or decrease may be observed in treated subjects as compared to subjects not treated with the mito-honokiol or mito-magnolol compounds of the present invention, where the untreated subjects have, or are subject to developing, the same or similar disease, condition, symptom or the like. Such increases or decreases may be at least about 2%, 5%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or about within any range about between any two of these values. Modulation may be determined subjectively or objectively, e.g., by the subject's self assessment, by a clinician's assessment or by conducting an appropriate assay or measurement, including, e.g., quality of life assessments or suitable assays for the level or activity of molecules, cells or cell migration within a subject. Modulation may be transient, prolonged or permanent or it may be variable at relevant times during or after the mito-honokiol or mito-magnolol compounds of the present invention is administered to a subject or is used in an assay or other method described herein or a cited reference, e.g., within about 1 hour of the administration or use of the mito-honokiol or mito-magnolol compounds of the present invention to about 3, 6, 9 months or more after a subject(s) has received the mito-honokiol or mito-magnolol compounds of the present invention.

By "administering" we mean any means for introducing the mito-honokiol or mito-magnolol compounds of the present invention into the body, preferably into the systemic circulation. Examples include but are not limited to oral, buccal, sublingual, pulmonary, transdermal, transmucosal, as well as subcutaneous, intraperitoneal, intravenous, and intramuscular injection. Another method of administration comprises oral gavage. A preferred method of administering the mito-magnolol compounds or pharmaceutical compositions of the present invention for treatment of cancer, particularly melanoma, is by oral or topical administration. Administering also includes introducing the mito-magnolol compounds or compositions locally to the cancer, for example, but not limited to, by topical treatment or injection into the tumor site.

A preferred method of administering the mito-honokiol compounds or pharmaceutical compositions of the present invention for treatment of cancer, particularly lung cancer, is by aerosol. Another suitable method of administration is oral.

The term "effective amount" or "therapeutically effective amount" refers to an amount sufficient to effect beneficial or desirable biological and/or clinical results. That result can be reducing, inhibiting or preventing the growth of cancer cells, including drug-resistant or therapy resistant cancer cells, reducing, inhibiting or preventing metastasis of the cancer cells or invasiveness of the cancer cells or metastasis, or reducing, alleviating, inhibiting or preventing at least one symptoms of the cancer or metastasis thereof, or any other desired alteration of a biological system. An "effective treatment" refers to treatment producing a beneficial effect, e.g., amelioration of at least one symptom of a cancer. A beneficial effect can take the form of an improvement over baseline, i.e., an improvement over a measurement or observation made prior to initiation of therapy according to the method. A beneficial effect can also take the form of reducing, inhibiting or preventing further growth of cancer cells, reducing, inhibiting or preventing metastasis of the cancer cells or invasiveness of the cancer cells or metastasis or reducing, alleviating, inhibiting or preventing at least one symptoms of the cancer or metastasis thereof. Such effective treatment may, e.g., reduce patient pain, reduce the size or number of cancer cells, may reduce or prevent metastasis of a cancer cell, or may slow cancer or metastatic cell growth.

In one embodiment, the therapeutically effective amount ranges from between about 5-50 mg/kg. A therapeutically effective amount of the mito-honokiol compounds of the invention may vary according to factors such as the disease state, age, sex, and weight of the subject, and the ability of the mito-honokiol compounds to elicit a desired response in the subject. Dosage regimens may be adjusted to provide the optimum therapeutic response. A therapeutically effective amount is also one in which any toxic or detrimental effects of the mito-honokiol compounds of the present invention are outweighed by the therapeutically beneficial effects. In one embodiment, the therapeutically effective amount of mito-magnolol ranges from between about 0.1-50 mg/kg. A therapeutically effective amount of the mito-magnolol compounds vary according to factors such as the disease state, age, sex, and weight of the subject, and the ability of the mito-magnolol compounds to elicit a desired response in the subject. Dosage regimens may be adjusted to provide the optimum therapeutic response. A therapeutically effective amount is also one in which any toxic or detrimental effects of the mito-magnolol compounds of the present invention are outweighed by the therapeutically beneficial effects.

A "prophylactically effective amount" refers to an amount effective, at dosages and for periods of time necessary, to achieve the desired prophylactic result, such as preventing or inhibiting the rate of metastasis of a tumor. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In one embodiment, the disclosure provides a method of treating cancer in a subject having cancer comprising: administering the mito-magnolol compound described herein in a therapeutically effective amount to treat the cancer.

In a preferred embodiment, the cancer is a melanoma, and in some embodiments, is a melanoma resistant to cancer therapy, for example, chemotherapy or immunotherapy. In some embodiments, the melanoma is resistant to BRAF inhibitor. In other embodiments, the melanoma is resistant to MEK inhibitor.

In some embodiment, the cancer therapy is a BRAF inhibitor. Suitable BRAF inhibitors are known in the art and include, but are not limited to, vemurafenib, dabrafenib, encorafenib, among others. In one example, the BRAF inhibitor is vemurafenib.

In another embodiment, the cancer therapy is a MEK inhibitor. Suitable MEK inhibitors include, but are not limited to, for example, trametinib (Mekinist), cobimetinib (Cotellic), and binimetinib (Mektovi), among others.

In a further embodiment, the cancer therapy is a checkpoint inhibitor. Suitable checkpoint inhibitors are known in the art and include, but are not limited to, for example, a PD-1 inhibitors, PD-L1 inhibitors, CTLA-4 inhibitors, and the like. Suitable PD-1 inhibitors include, but are not limited to, for example, anti-PD-1 antibodies, e.g. pembrolizumab (Keytruda), Nivolumab (Opdivo), and Cemiplimab (Libtayo), among others. Suitable anti-PD-L1 inhibitors, include, but are not limited to, for example, anti-PD-L1 antibodies, including, but not limited to, Atezolizumab (Tecentriq), Avelumab (Bavencio), and Durvalumab (Imfinzi), among others.

The present disclosure also provides methods of reducing or inhibiting cancer cell growth in a subject having cancer, the method comprising administering the mito-magnolol compound described herein in a therapeutically effective amount to reduce or inhibit cancer cell growth. In some embodiments, the cancer cell is resistant to an anti-cancer therapy or drug, for example, a BRAF inhibitor.

In another embodiment, the disclosure provides a method of inhibiting, preventing or delaying resistance of a cancer to an anti-cancer drug in a subject, the method comprising: administering the mito-magnolol compound or compositions described herein in a therapeutically effective amount to inhibit, prevent or delay resistance of the cancer to the anti-cancer drug.

In some embodiments, any of the methods described herein include administering the mito-magnolol compound in combination with one or more cancer therapies as further described herein. Suitable cancer therapies (i.e., anti-cancer therapies) are known in the art, and may include cancer therapies in which the tumor is resistant to when administered alone.

In some embodiments, the mito-magnolol compound is administered co-currently with the anti-cancer drug. In other embodiments, the mito-magnolol compound or composition is administered after beginning treatment with the anti-cancer drug. In other embodiments, the mito-magnolol compound or composition is administered before, during, or both before and during treatment with an anti-cancer drug.

The disclosure further provides methods of increasing a T cell response to an anti-cancer therapy in a cancer patient, the method comprising administering the mito-magnolol compound or composition in a therapeutically effective amount to increase the T cell response to the therapy. In some embodiments, the anti-cancer therapy is a BRAF inhibitor or an inhibitor of oncogenic kinase. In another embodiment, the anti-cancer therapy is a checkpoint inhibitor.

The term "anti-cancer therapy," "cancer therapy," and "anti-cancer drug" are used interchangeably to refer to therapeutics that are used for the treatment of cancer, including chemotherapy, immunotherapy, among others. Suitable anti-cancer therapies are known in the art and depend on the type of cancer being treated. Suitable anti-cancer therapies are described herein and include, for example kinase inhibitors, including BRAF inhibitors or MEK inhibitors, checkpoint inhibitors, and chemotherapeutics.

Figure 18:
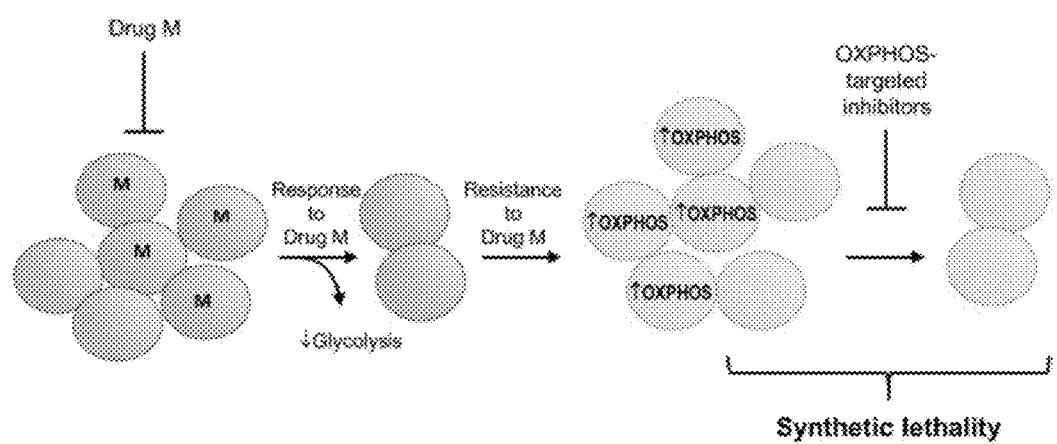
FIG. 18 shows a schematic representation of an OXPHOS inhibitor inducing synthetic lethality to tumor cells which are resistant to kinase inhibitor, Drug M.

In another embodiment, the mito-magnolol compounds and compositions described herein are able to provide synthetic lethality as OXPHOS inhibitors. In one embodiment, the mito-magnolol compounds and compositions are able to overcome resistance to oncogene-targeted therapies. The concept of synthetic lethality that has been frequently used in targeted chemotherapy is schematically shown in FIG. 18. There are several types of synthetic lethality (20,21) as follows: 1) Genotype-specific synthetic lethality between two genes (gene products) occurs when the cell is functional with mutation of one gene but loss of both genes trigger cancer cell death; 2) Drug-specific synthetic lethality occurs when cells treated with an inhibitor or drug M for a mutated oncogene adapt another signaling pathway and the use of another drug (targeted inhibitor of OXPHOS) for the new adapted signaling pathway induces toxicity to mutated cancer cells (FIG. 18).

The therapeutic combinations of an anti-cancer therapy, preferably in one embodiment a kinase inhibitor (e.g., BRAF inhibitor) with mito-magnolols described herein can be used for inhibiting OXPHOS is an example of drug-specific synthetic lethality. This disclosure demonstrates synthetic lethality through pharmacological mechanism targeting the adaptive potential of transformed cells to upregulate OXPHOS in cancer cells subjected to oncogenic kinase inhibition. Through synthetic lethality mechanism, the MTAs described herein through inhibiting OXPHOS can mitigate and delay onset of drug resistance to anti-cancer therapies, including chemotherapies and immunotherapies, for example, the combination therapy of metformin and vemurafenib, inhibitor of oncogenic BRAFV600E, in metastatic melanoma patients. The Examples demonstrate the use Mito-magnolol in wild type and BRAFV600E-resistant melanoma cells.

In one embodiment, the compounds and compositions described herein are used in methods of reducing, suppressing, or killing BRAF inhibitor resistant cells.

In some embodiments, the mito-magnolol compounds and compositions described herein can be used synergistically in combination with a checkpoint inhibitor to treat cancer. In some embodiments, the checkpoint inhibitor is a PD-1 or a PD-L1 checkpoint inhibitor.

Kits. In another embodiment, the present invention provides a kit comprising a pharmaceutical composition comprising the mito-honokiol compounds or mito-magnolol compounds of the present invention and instructional material. By "instructional material" we mean a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

In some embodiments, the kit may further comprise one or more anti-cancer therapies to use in combination with the mito-magnolol compounds.

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1. Synthesis of Mito-Honokiol Compounds

The mito-honokiol compounds of the present invention are synthesized according to the following reaction:

Scheme 1. Synthesis of mito-honokiols

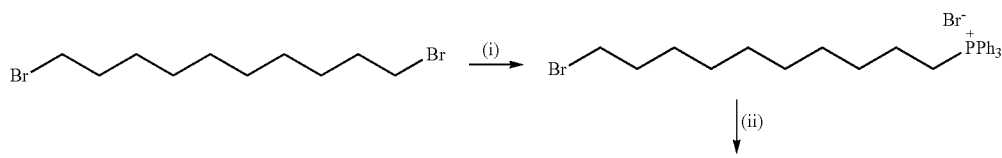

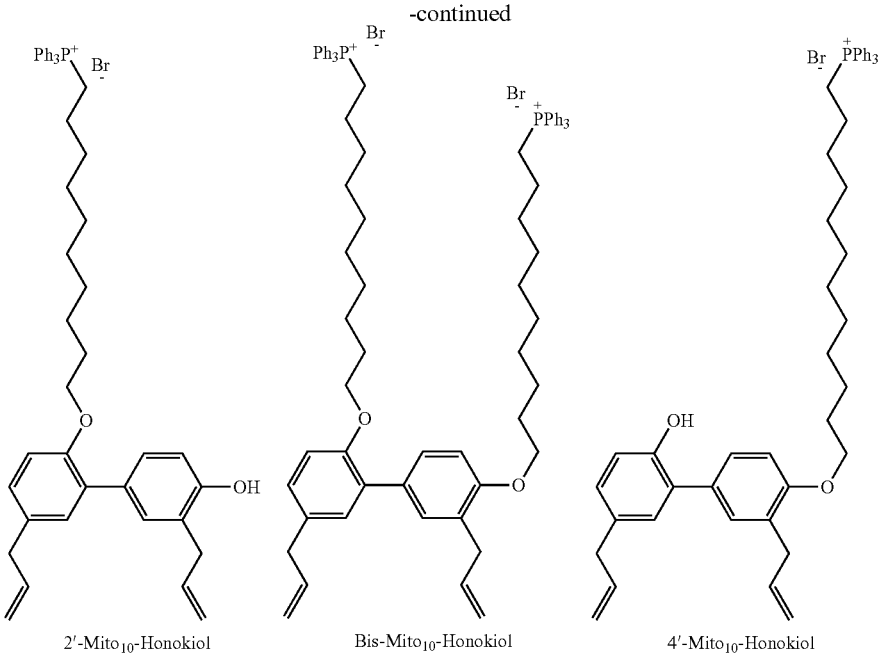

Reagents and conditions: (i) PPh₃, neat, 6 h, 90° C., 47%; (ii) Honokiol, K₂CO₃, DMF, 80%.

10-Bromodecyltriphenylphosphonium Bromide 1.

A mixture of triphenylphosphonium (1 g, 3.8 mmol) and dibromide (5.7 g, 19 mmol) was heated at 90° C. for 6 h. After cooling, the crude product was purified by flash chromatography (pentane, Et₂O and CH₂Cl₂/EtOH 9:1) to afford the corresponding phosphonium salt 1 as a white solid (1 g, 47% yield). $^{31}$P (400.13 MHz, CDCl₃) δ 24.32. $^1$H NMR (400.13 MHz, CDCl₃) δ 7.85-7.65 (15H, m), 3.73-3.66 (2H, m), 3.40-3.34 (2H, m), 1.80-1.75 (4H, m), 1.31-1.20 (12H, m).

Mito-Honokiol and Bis-Mito-Honokiol.

To a mixture of honokiol (0.27 g, 2.6 mmol), anhydrous potassium carbonate (0.28, 2 mmol) in DMF (4 mL) was added compound 1 (0.57, 1.0 mmol). The mixture was stirred at 30° C. for 6 h. The solvent was removed under vacuum and the residue was taken up into water and extracted with CH₂Cl₂. The organic layer was dried over Na₂SO₄, and the solvent was removed under reduced pressure. Purification by flash chromatography (Et₂O, CH₂Cl₂ and CH₂Cl₂/EtOH) delivered the corresponding Mito-Honokiols isomers (2, 3) and the Bis-Mito-Honokiol (4) as white solids (2, 3, 200 mg, % yield and 4, 50 mg, % yield). HRMS calculated for 2, 3 C₄₆H₅₂O₂P [MH]⁺ 667.3699, found, 667.3699. HRMS calculated for 4 C₇₄H₈₆O₂P₂ [MH]²⁺ 534.3046, found, 534.3044.

Mito-Honokiols 2, 3.

$^{31}$P (400.13 MHz, CDCl₃) δ 24.38, 24.28. $^1$H NMR (400.13 MHz, CDCl₃) δ 7.86-7.65 (15H, m), 7.35-6.95 (5H, m), 6.87 (1h, 2d), J=8.3, 8.5), 6.06-5.86 (2H, m), 5.10-4.93 (4H, m), 3.98 (1H, t, J=3.9), 3.89 (1H, t, J=3.8), 3.80-3.70 (2H, m), 3.4-3.33 (4H, m), 1.77-1.30 (10H, m), 1.1-1.07 (6H, m).

Bis-Mito-Honokiol 4.

$^{31}$P (400.13 MHz, CDCl₃) δ 24.37. $^1$H NMR (400.13 MHz, CDCl₃) δ 7.88-7.70 (30H, m), 7.35-7.32 (2H, m), 7.12 (1H, d, J=1.7), 7.07 (1H, dd, J=8.3, 2.0), 6.88 (1H, d, J=8.3), 6.85 (1H, d, J=8.3), 6.05-5.85 (2H, m), 5.13-4.93 (4H, m), 3.97 (2H, t, J=6.3), 3.90 (2H, t, J=6.3), 3.85-3.73 (4H, m), 3.39 (2H, d, J=6.8), 3.36 (2H, d, J=6.5), 1.71-1.50 (10H, m), 1.20-1.33 (22H, m).

Example 2. Synthesis of

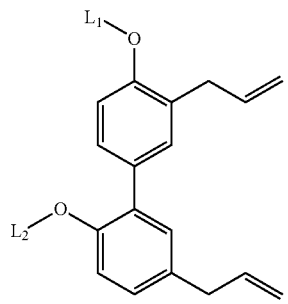

where L1 and/or L2 are comprised of organic linker attached to triphenylphosphonium moiety Synthetic Example
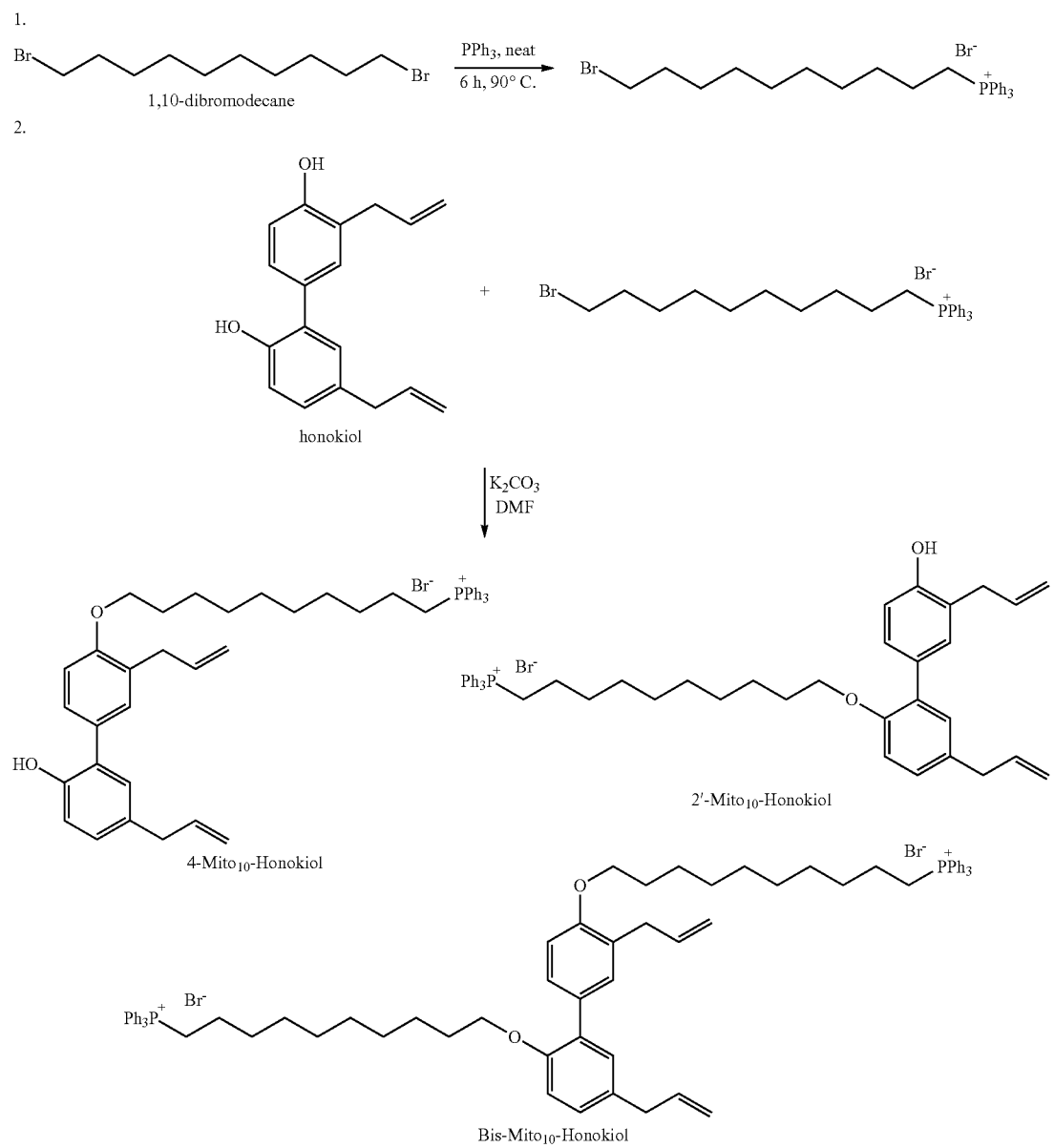
Example 3. Synthesis of
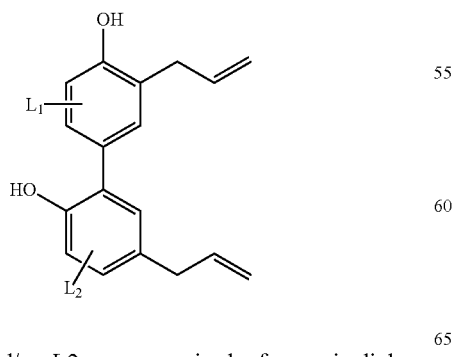
where L1 and/or L2 are comprised of organic linker attached to triphenylphosphonium moiety Synthetic Example
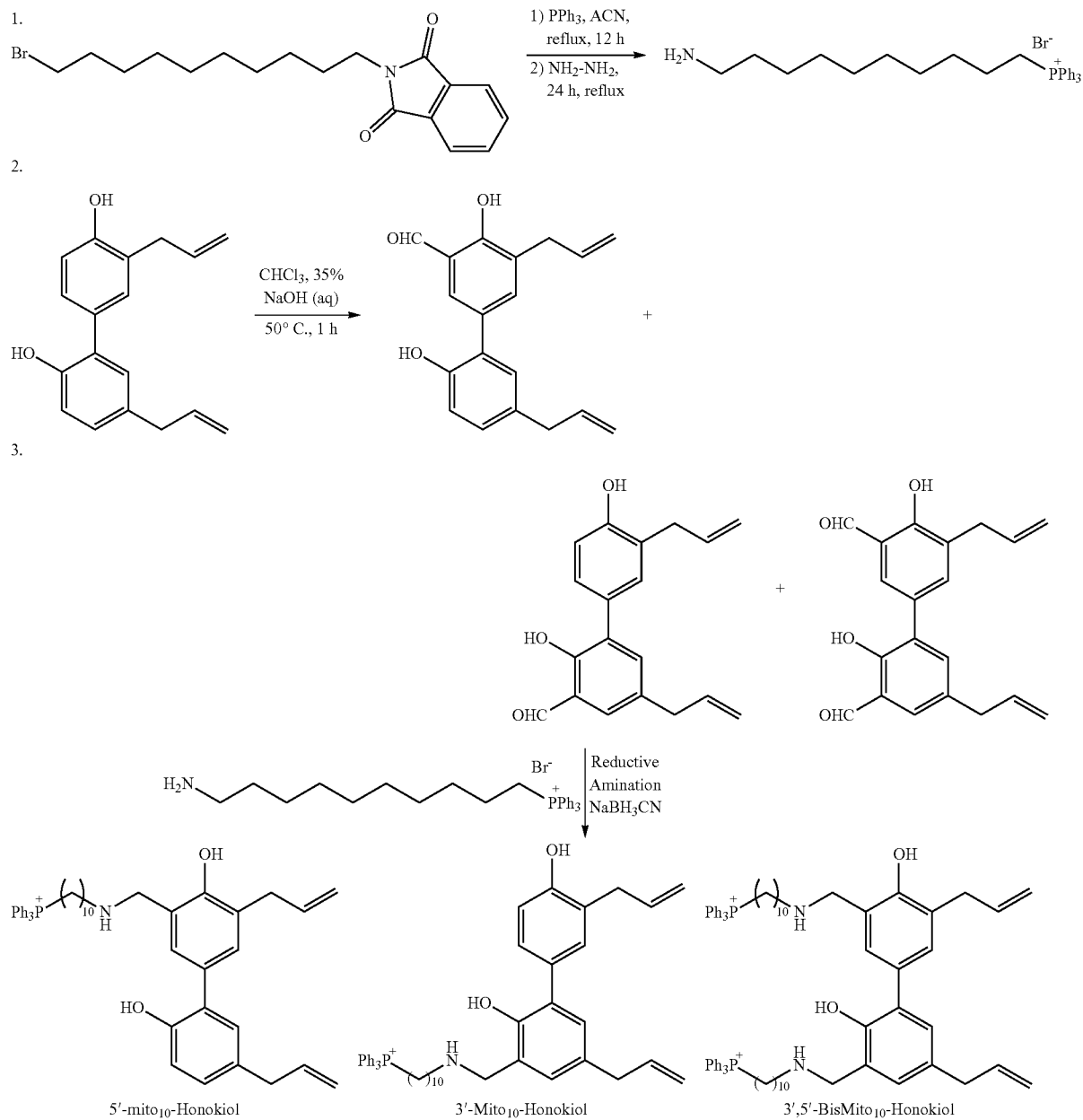
Example 4. Synthesis of
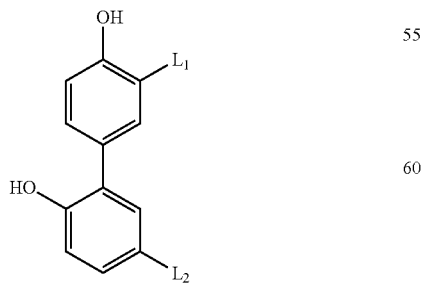
where L1 and/or L2 are comprised of organic linker attached to triphenylphosphonium moiety Synthetic Example
1.
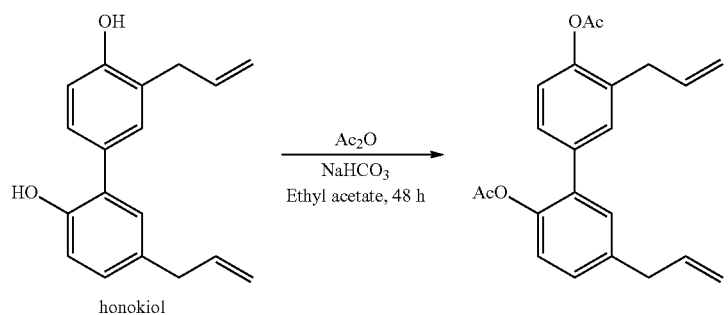
2.
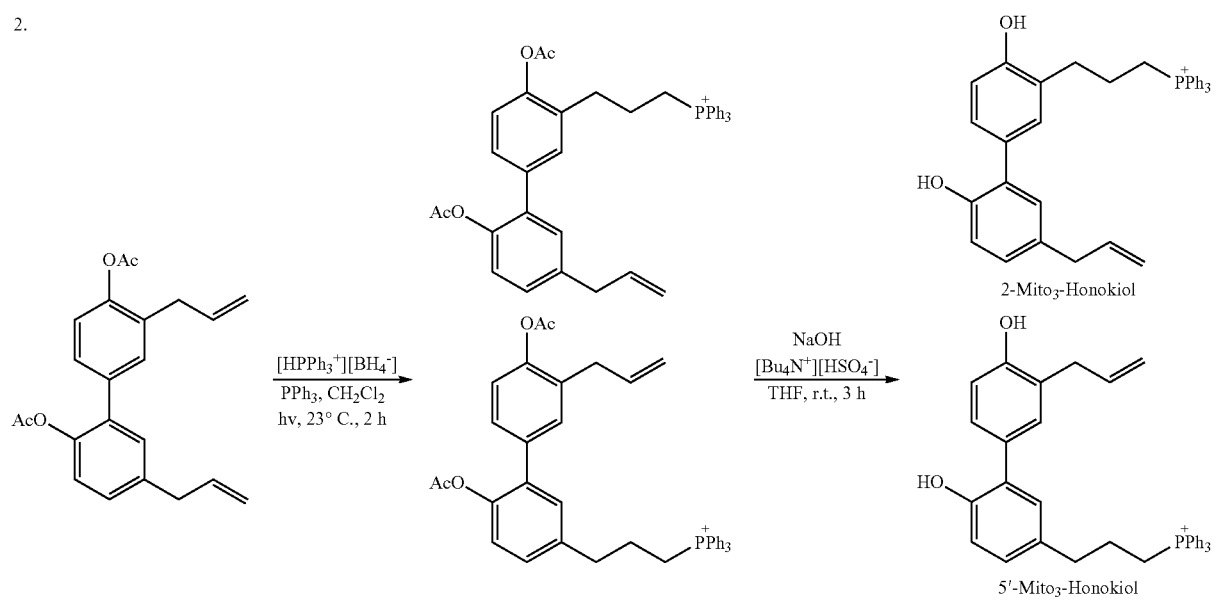
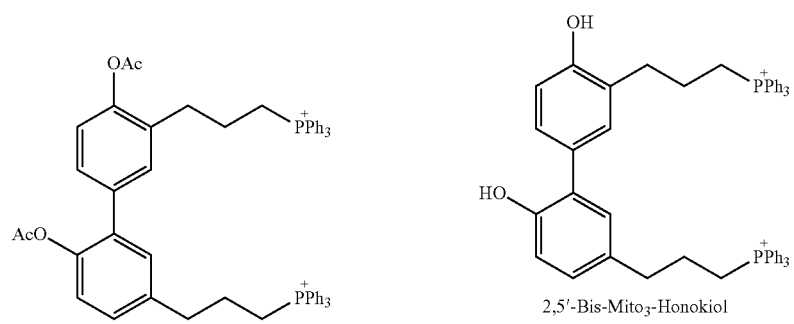

Example 5. Synthesis of
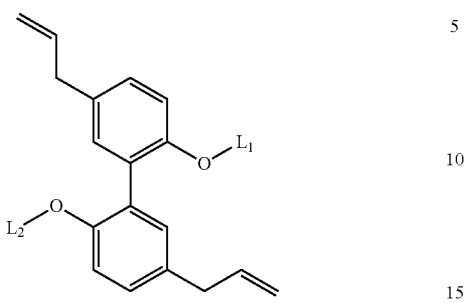
where L1 and/or L2 are comprised of organic linker attached to triphenylphosphonium moiety
Synthetic Example
1.
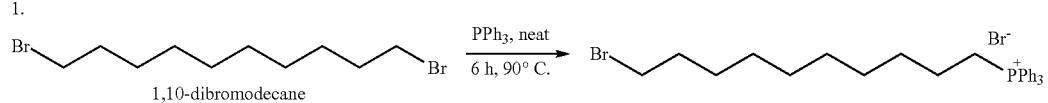
2.
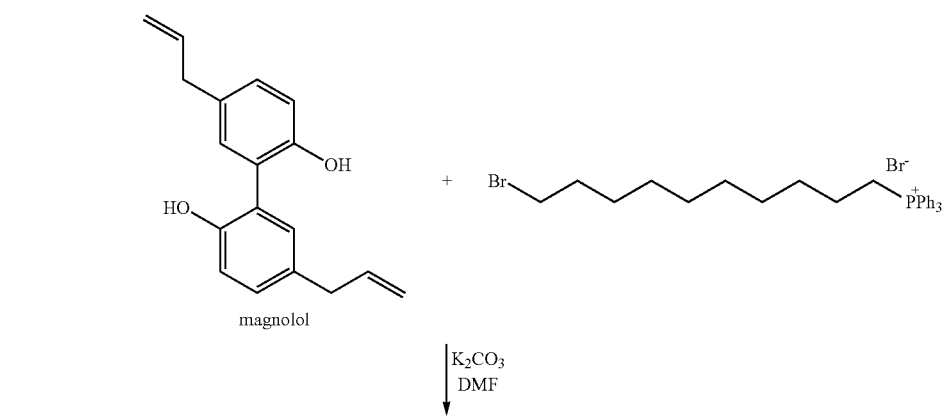
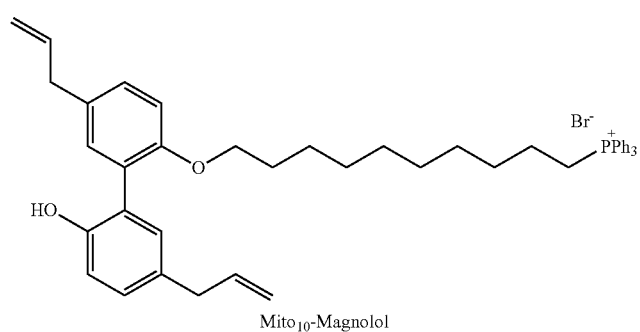

-continued
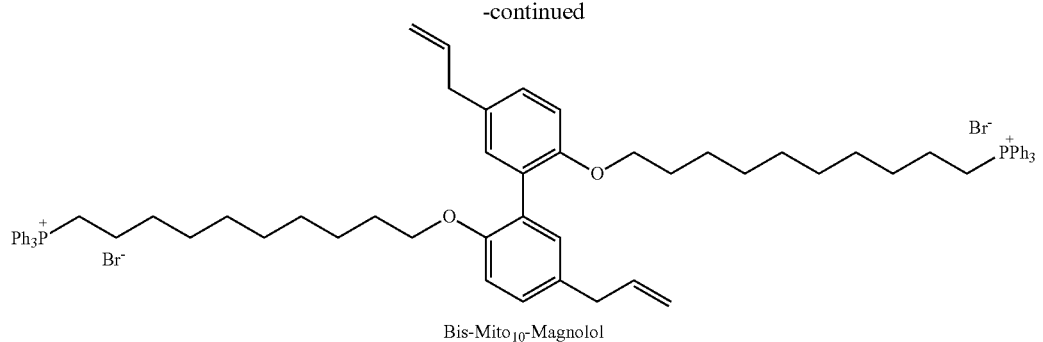
Bis-Mito₁₀-Magnolol
Example 6. Synthesis of
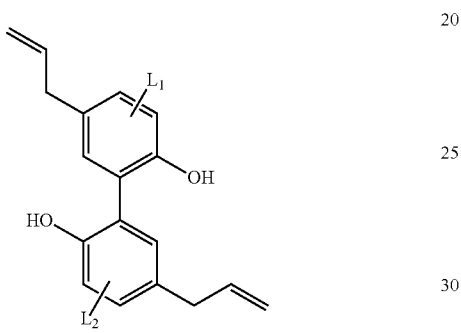
where L1 and/or L2 are comprised of organic linker attached to triphenylphosphonium moiety
Synthetic Example
1.
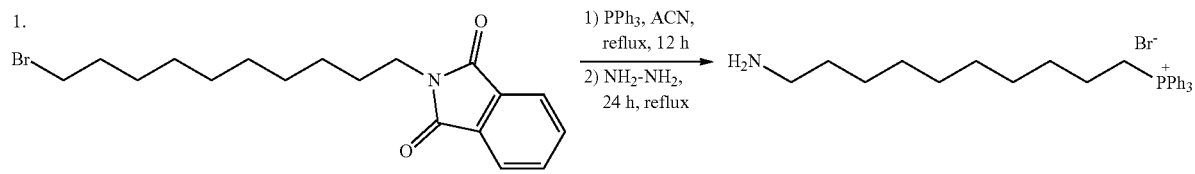
2.
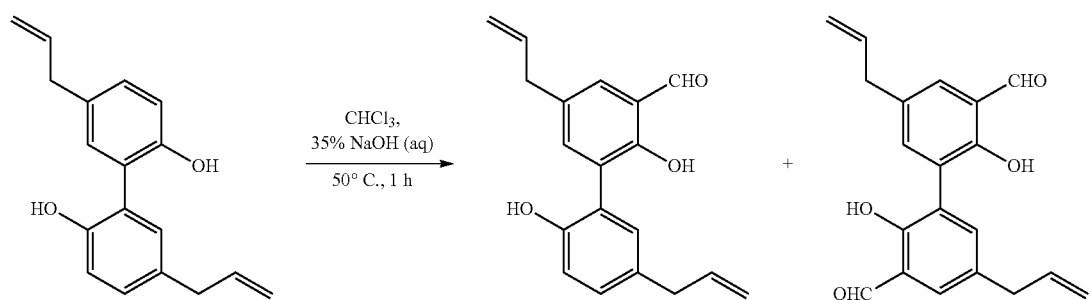

3.
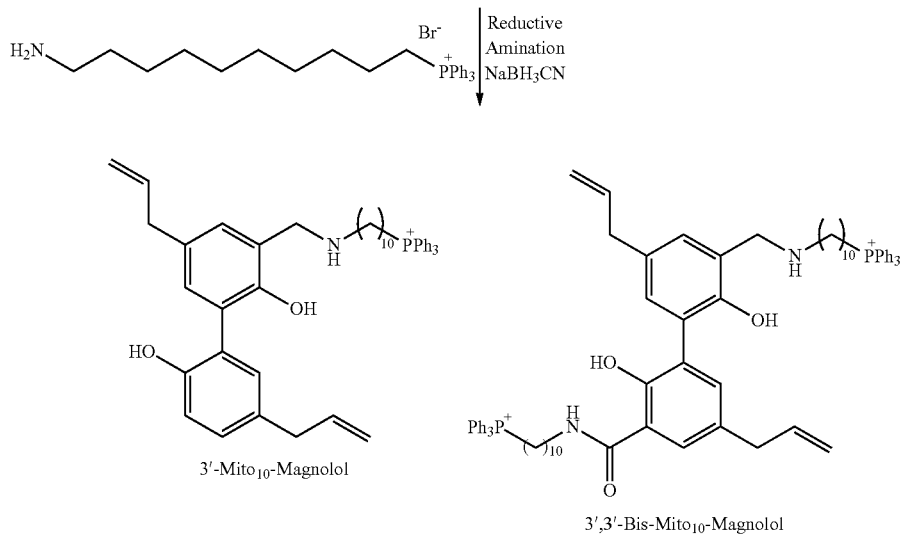
Example 7. Synthesis of
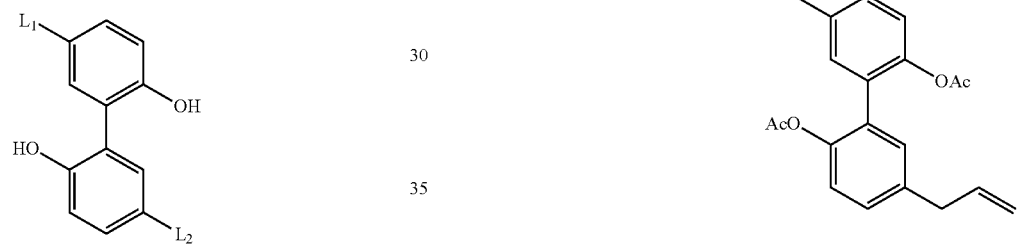
where L1 and/or L2 are comprised of organic linker attached to triphenylphosphonium moiety
Synthetic Example
1.
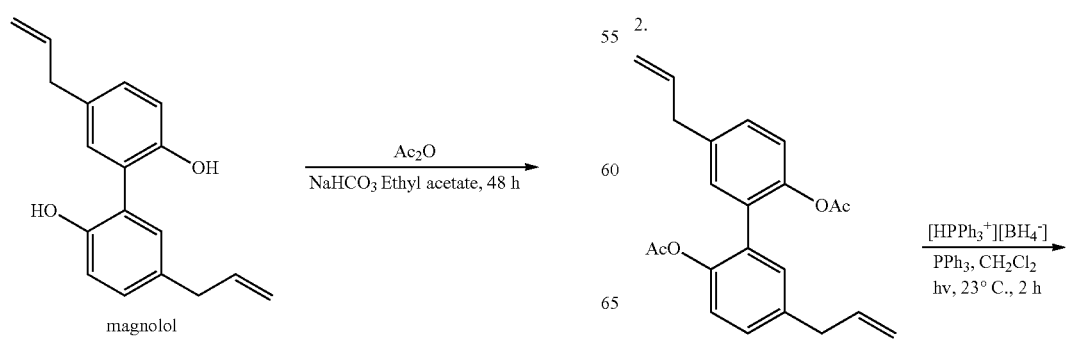

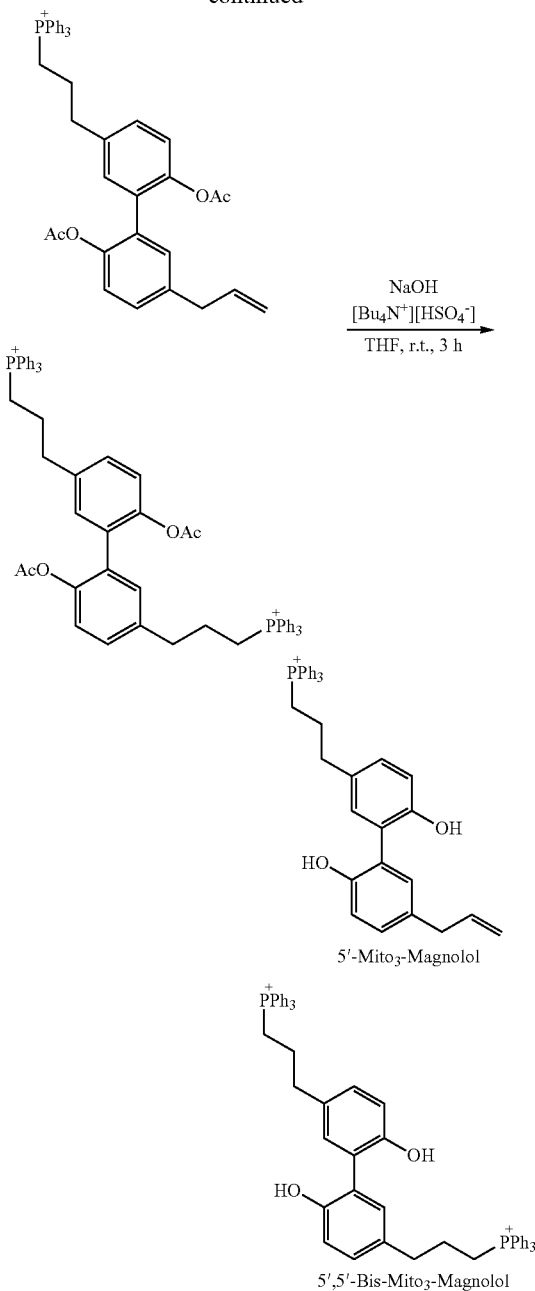

Example 8: Use in Treatment of Cancer and Metastasis

Lung cancer is the leading cause of cancer death in the United States. Metastasis to lymph nodes (LN) and distal organs, especially the brain, leads to severe complications and is a major cause of death. Prevention of lung cancer development and metastases is an important strategy to reduce lung cancer mortality.

This Example demonstrates mitochondria-targeted HNK (Mito-HNK) is significantly more potent than HNK in the inhibition of lung cancer progression and lung cancer metastasis, specifically brain metastasis. The antimetastatic effects of Mito-HNK was evaluated in both LN and brain murine models of lung tumor metastasis. The H2030-BrM3 (Br- brain seeking) and DMS-273 lung tumor cells stably transfected with luciferase and green fluorescent protein were orthotopically injected into the lung for LN metastases, or directly injected into the left ventricle of the mouse for brain metastases. LN and brain metastases were monitored using a noninvasive bioluminescent in vivo imaging. Unless specified, Mito-HNK$_{10}$ (or Mito-HNK) relates to the mixture of the two isomers (2'-Mito-HNK and 4'-Mito-HNK).

The efficacy of Mito-HNK in preventing the migration of tumor cells to LN or the brain was tested by treating mice with Mito-HNK by aerosol (for the lung-to-LN metastasis model) or oral gavage starting the day after the tumor cell injection. Results revealed that Mito-HNK significantly prevented the metastasis of lung cancer cells to LN and the brain. We demonstrated that Mito-HNK decreased LN metastases incidence to 30%, compared with 100% in control mice, and inhibited brain metastasis nearly 70% compared with the control. Furthermore, analysis of Mito-HNK's mechanism of action, utilizing both RNA sequencing and a tyrosine kinase assay, suggests that its effect is mediated primarily by inhibiting the mitochondria complex I-STAT3 pathway. Mito-HNK specifically inhibits STAT3 phosphorylation regardless of EGFR (epidermal growth factor receptor) mutation status, and knockdown STAT3 abrogated both the antiproliferative and antimetastasis effects of Mito-HNK in brain metastatic and small lung cancer cells. These finding suggest that Mito-HNK could provide novel chemopreventive or therapeutic options for preventing both lung tumor progression and lung cancer metastasis.

Materials and Methods

Cell Culture and Reagents

Brain metastatic lung cancer cell lines PC9-BrM3 and H2030-BrM3 were generous gifts from Dr. Joan Massage (Memorial Sloan Kettering Cancer Center, New York, NY). Small cell lung cancer cell line DMS-273 was purchased from Sigma-Aldrich (St. Louis, MO). Both PC9-BrM3 and H2030-BrM3 cell lines were maintained in RPMI-1640 medium (Gibco) supplemented with 10% fetal bovine serum, and DMS-273 cells were maintained in Waymouth's medium supplemented with 10% fetal bovine serum (FBS) (Invitrogen, Carlsbad, CA) and 2 mM glutamine (Fisher Scientific, Pittsburgh, PA) in a 37° C. humidified 5% CO2 incubator. Honokiol was purchased from Sigma-Aldrich (St. Louis, MO).

Cell Proliferation Assay

For the cell proliferation assay, cells were seeded onto 96-well tissue culture plates at 2-3,000 cells per well. Twenty-four hours after seeding, treatment group cells were exposed to various concentrations of HNK for 48 hours, and control group cells received fresh medium. The plate was incubated at 37° C. and 5% $CO_2$ and monitored in IncuCyte (Essen Bioscience, Ann Arbor, MI). Data analysis was conducted using IncuCyte 2011A software. All assays were performed in triplicate.

Transwell Invasion Assay

Boyden chamber transwells precoated with growth-factor-reduced Matrix were purchased from Fisher Scientific (Pittsburgh, PA). Transwell invasion assays were performed as described in the manufacture's protocol. Briefly, 2-3×10$^5$ cells were seeded into each transwell filled with serum-free RPMI-1640 media containing 10 μM HNK. Bottom wells were filled with RMPI-1640 media or Waymouth's medium with 10% FBS and either 10 μM or 20 μM HNK or 0.1 μM or 0.2 μM Mito-HNK. After 36 hours, cells were fixed with 10% formalin and stained with 5% crystal violet in 70% ethanol. Invaded cells were counted at a magnification of 10× in three randomly selected areas of each transwell, and the results were normalized to the control.

PathScan Receptor Tyrosine Kinase Assay

H2030-BrM3 and DMS-273 cells treated with control DMSO and various doses of HNK and Mito-HNK for four hours were lysed with 200 µl lysis buffer containing proteinase inhibitor cocktails (Cell Signaling Technology, Danvers, MA), sheared 10 times with a 28-gauge needle, spun at 16,000×g for 30 min, and normalized by protein concentration as determined by the Bradford method. Normalized lysate was resolved in a PathScan RTK Signaling Array, and the signaling array was examined by a Li-COR Odyssey infrared imaging system (Li-COR Biosciences-Biotechnology, Lincoln, NE).

Western Blot Analysis

Cells were lysed with 200 µl of RIPA buffer containing proteinase inhibitor cocktails (Fisher Scientific, Pittsburgh, PA), sheared 10 times with a 28-gauge needle, spun at 16,000×g for 30 minutes, normalized by protein concentration as determined by the Bradford method, and boiled for 5 min. Normalized lysate was resolved by 4-12% sodium dodecyl sulfate polyacrylamide gel electrophoresis (SDS-PAGE) (Invitrogen, Carlsbad, CA) and immunoblotting with indicated antibodies. The following antibodies were used: p-EGFR (#3777S, Cell Signaling Technology, Danvers, MA), p-STAT3 (#9131S, 9134S, Cell Signaling Technology, Danvers, MA), p-AKT (#40605, Cell Signaling Technology, Danvers, MA), EGFR (4267S, Cell Signaling Technology, Danvers, MA), STAT3 (9139S, Cell Signaling Technology, Danvers, MA), AKT (92725, Cell Signaling Technology, Danvers, MA), Actin (SC-8432, Santa Cruz Biotechnology, Dallas, TX).

RNA Sequencing and Pathway Analysis

We conducted an RNA sequence study of human lung tumor metastases in mouse brains. Three brain metastases were sampled from mice not treated with HNK, and another three brain metastases were obtained from mice treated with HNK. Total RNA samples were extracted from these six samples using a Qiagen RNeasy Mini Kit. The quality of the total RNA samples obtained was very high, with RIN (RNA integrity number) values in the range of 9-10, and subjected to mRNA sequencing. We used a NEBNext Ultra RNA Library Prep Kit for Illumina to construct the RNA sequence libraries for these brain metastasis samples. The Agilent High Sensitivity DNA Chip analysis showed a narrow distribution (200-1000 bp) with a peak size of approximately 300 bp for the prepared RNA sequence library samples, indicating that they are of high quality for sequencing. A whole transcriptome analysis of these RNA-sequence library samples was performed using the HiSeq 2500 Sequencing platforms (Illumina, San Diego, CA). The experiment was single-end with a 50 nt read length. The qualities of the RNA sequence reads were analyzed using the FastQC program (http://www.bioinformatics.babraham.ac.uk/projects/fastqc/). Coverage for the samples ranged from 15 million-32 million reads per sample. The quality scores across all bases of the individual reads were at least >30, with an average around 37, and greatly exceeded the normal threshold of 20. In order to identify and unequivocally separate graft (human) and host (mouse) reads, processed sample reads were sequentially aligned to both graft (complete hg19 human genome [UCSC version, February 2009]) and host (complete mm9 mouse genome [UCSC version, July 2007]) genomes using Bowtie-TopHat (version 2.0.4, segment length 29 nt, one mismatch in segment permitted, for maximum sensitivity, coverage search performed) (Langmead et al., 2009; Trapnell et al., 2009). No deduplication was performed for post-assembly RNA-sequence analysis. Read counts were obtained using HTseq (Anders et al., 2015). Data normalization and differential expression analysis were performed using the statistical algorithms implemented in the EdgeR Bioconductor package (Robinson et al., 2010). False discovery rate (FDR)-corrected p-values of less than 0.05 were used as criteria for significantly regulated genes. In addition, both metastatic tumors (human) and stroma (mouse) cells were used to identify key gene expression patterns in response to HNK using the species-specific RNA-sequence approach. We used a strategy that efficiently separates human lung tumor sequence data from that of xenograft mice (mice with genetically human tumors) into separate microenvironment and tumor expression profiles (Bradford et al., 2013; Rossello et al., 2013). Using this tool, we obtained more-accurate RNA expression profiles for both metastatic human lung tumors and mouse stromal cells.

Endogenous STAT3 Knockdown

Lentiviral particles against STAT3 were purchased from Santa Cruz Biotechnology, Inc. (Dallas, TX). Lentiviral particles were infected in PC9-BrM3, H2030-BrM3, and DMS-273 in the presence of 8 µg/mL polybrene, and infected cells were selected with puromycin (2 µg/ml) for three days to obtain stable knockdown cells.

Brain Metastases in Mouse Model Via Ultrasound-Guided Left Ventricle Injection Technique Animal procedures were performed in accordance with the Medical College of Wisconsin Institutional Animal Care and Use Committee. For the lung cancer brain metastasis study, four-six-week-old, female, nonobese-diabetic-background (NOD/SCID) mice were used. $2 \times 10^5$ brain-seeking cells, H2030-BrM3, were suspended in 0.1 ml PBS and injected into the left ventricle under ultrasound guide (ECHO 707, GE, Milwaukee, WI). One day after engrafting H2030-BrM3 cells in arterial circulation, mice were randomly grouped into the vehicle treatment group or the HNK treatment group (10 mg/kg body weight). Mice were treated with either solvent control (0.1% DMSO in coin oil) or HNK by oral gavage for four weeks; during this time, metastases were monitored by bioluminescence with an Xenogen IVIS-200 (Alameda, CA) alone at treatment time, and were confirmed with ex vivo luminescence, ex vivo green fluorescent protein (GFP) fluorescence, and haematoxylin and eosin (H&E) and GFP staining at the endpoint.

For the lung tumor lymph nodes metastasis study, $10^4$ cells were resuspended in a 1:2 mixture of PBS and growth factor reduced Matrigel (BD Biosciences, San Jose, CA) and then injected into the lung. HNK treatment was started one day post orthotopical injection of tumor cells via aerosol delivery.

In Vivo Orthotopic Lung Cancer Mouse Model

We used an orthotopic model of lung adenocarcinoma cells (H2030-BrM3 cells) in nude mice to evaluate the inhibitory effect of aerosolized HNK on lung tumor growth and lymph node metastasis. Five-week-old male athymic nude mice were used for experiments. Mice were anesthetized with isoflurane and placed in the right lateral decubitus position. A total of $1 \times 10^6$ H2030-BrM3 cells in 50 µg of growth factor reduced Matrigel (BD Biosciences, San Jose, CA) in 50 µL of RPMI-1640 medium were injected through the left rib cages of mice into their left lungs, as previously described (Nguyen et al., 2009). One week after the injections, mice in the HNK group were treated with 5 mg/ml aerosolized HNK once a day, five days a week, for four weeks. Tumor growth and metastases phenotypes were monitored during this time by bioluminescence with an Xenogen IVIS-200. Mice were sacrificed at the endpoint; tissues were extracted, freshly frozen, and OCT-fixed or formalin-fixed with 10% zinc for later western blot and immunohistochemistry (IHC) analyses.

In Vivo Imaging System

An in vivo imaging system (IVIS) consists of a highly sensitive, charge-coupled digital camera with accompanying advanced computer software for image data acquisition and analysis. This system captures photons of light emitted by reagents or cells that have been coupled or engineered to produce bioluminescence in the living animal. The substrate luciferin was injected into the intraperitoneal cavity at a dose of 150 mg/kg body weight (30 mg/ml luciferin) approximately 10 minutes before imaging. Mice were anesthetized with isoflurane/oxygen and placed on the imaging stage. Photons emitted from the lung region were quantified using Living Image software (Xenogen Corporation, Alameda, CA).

Histopathology Analysis

Mouse brains were fixed in a 10% zinc formalin solution overnight and stored in 70% ethanol for histopathology evaluation. Serial tissue sections (5 μm each) were made and stained with H&E or GFP and examined histologically under a light microscope to assess the severity of the tumor development.

Statistical Analysis

Figure 5A:
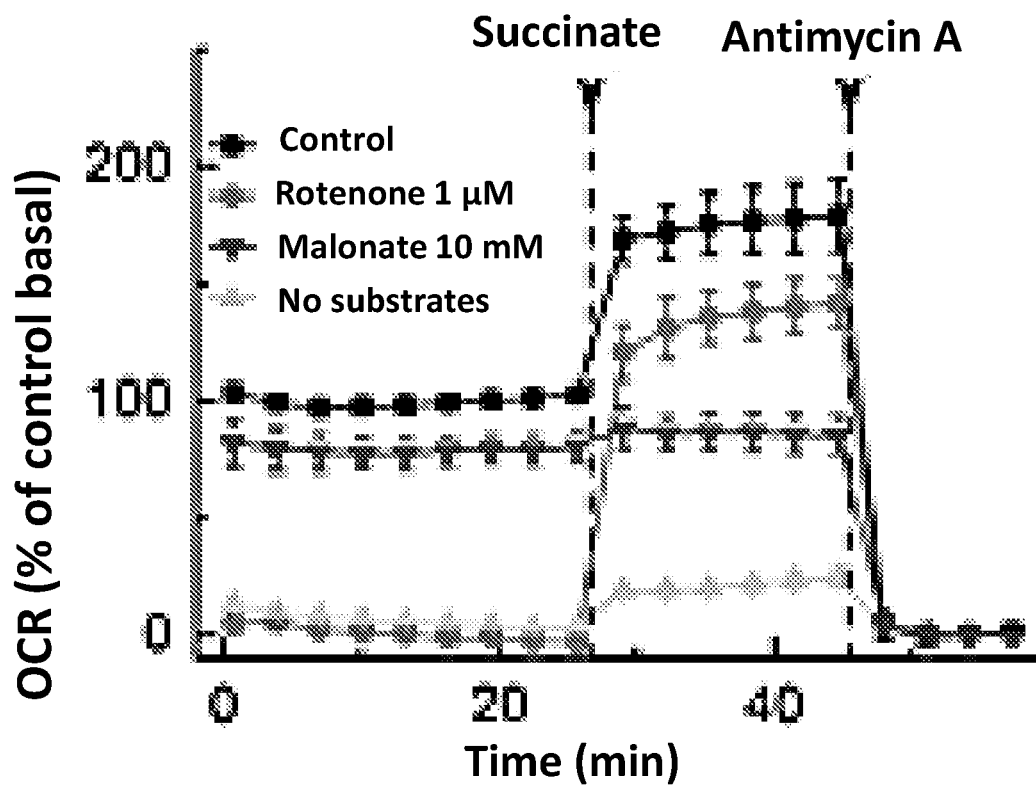
FIG. 5A-5D. Inhibition of mitochondrial complex I activity by mito-honokiol. Cells were pretreated for 24 h with Mito-HNK and HNK, cell-membrane was permeabilized, and OCR measured upon addition of mitochondrial substrates/inhibitors. (A, C) show OCR changes in the control and in rotenone- and malonate-treated permeabilized cells. Rotenone (a complex I inhibitor) greatly diminished OCR that was restored by added succinate. In the presence of malonate (a complex II inhibitor) that did not significantly affect complex I-mediated OCR, the addition of succinate did not stimulate OCR and the addition of antimycin A decreased both pyruvate- and succinate-induced OCR. Both HNK and Mito-HNK inhibit complex I in both H2030-BrM3n (B) and DMS-273 (D) cells.
Figure 5B:
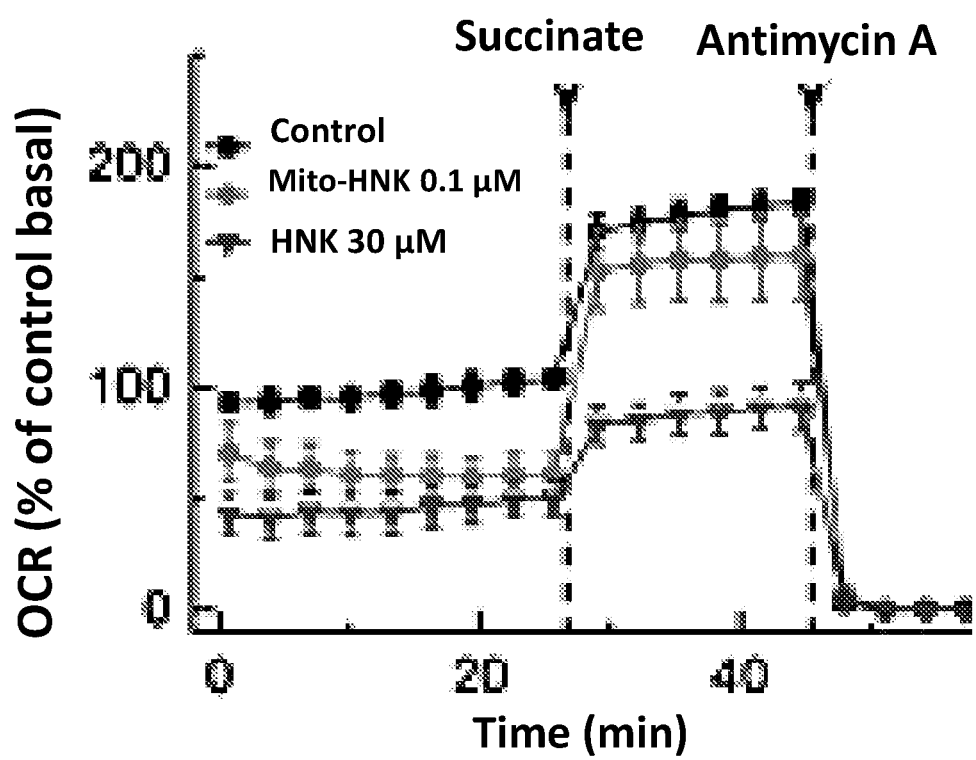
Figure 5C:
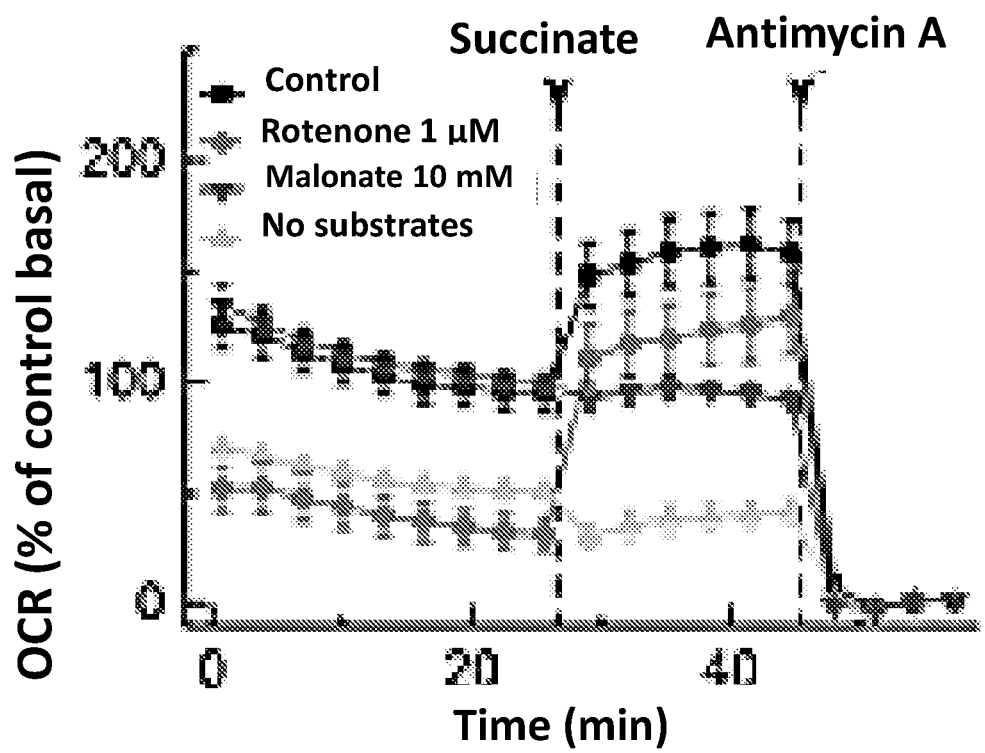
Figure 5D:
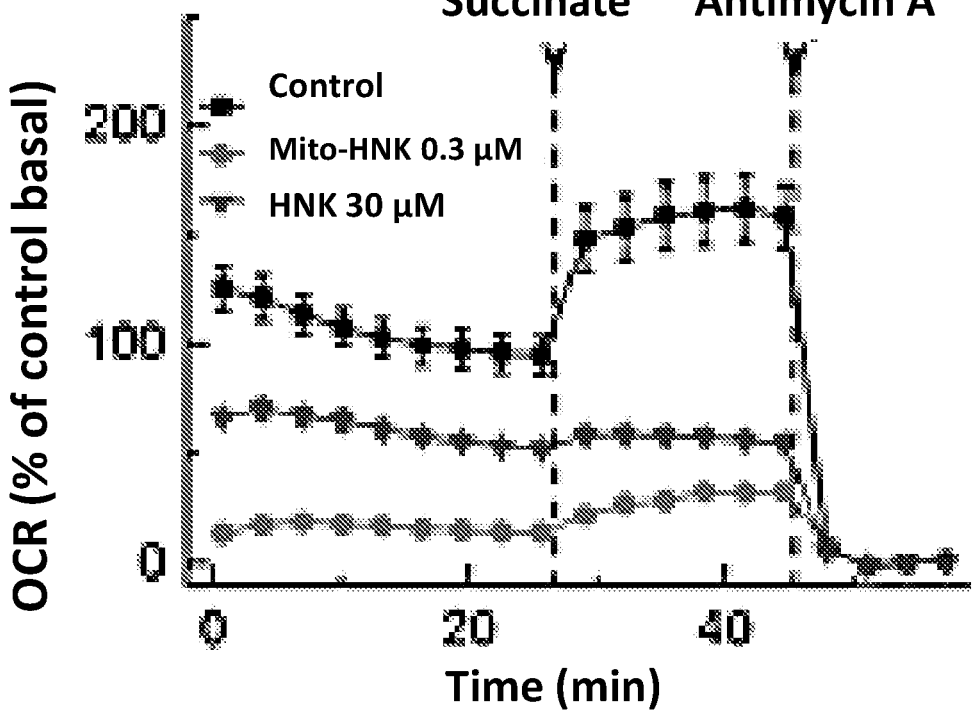

A two-tailed Student's T-test was used to evaluate the differences between the control samples and the treated samples. *P<0.05 and ** P<0.005 were considered statistically significant. Results Inhibition of Mitochondrial Complex I Activity Mito-HNK is designed to target mitochondria, so we examined the specificity of Mito-HNK in the inhibition of mitochondrial function and cellular respiration. We previously published that HNK inhibited squamous lung cancer progression by at least partially targeting mitochondria. Results indicate that Mito-HNK inhibits cellular respiration (or OCR) and mitochondrial function at a concentration more than 100-fold lower than HNK in intact H2030-BrM3 brain metastatic lung cancer cells (FIGS. 5A and 5B) and highly invasive DMS-273 small cell lung cancer cells (FIGS. 5C and 5D). Both the basal respiration and the response to mitochondrial stressors (oligomycin, dinitrophenol) were diminished by Mito-HNK (not shown). To investigate the mechanism of inhibition of mitochondrial function, we measured the activity of mitochondrial complexes in response to HNK and Mito-HNK. We pretreated cells with Mito-HNK and HNK for 24 h, permeabilized their cell membranes, and measured their OCR upon the addition of mitochondrial substrates/inhibitors. This approach has many advantages, including high throughput, the lack of requirement of cell fractionation, and the possibility of monitoring the effect on two mitochondrial complexes in a single run. FIGS. 5A and 5C show OCR changes in control and rotenone- and malonate-treated permeabilized cells. Rotenone (a complex I inhibitor) greatly diminished the OCR that was restored by added succinate. In the presence of malonate (a complex II inhibitor) that did not significantly affect complex I-mediated OCR, the addition of succinate did not stimulate OCR and the addition of antimycin A decreased both pyruvate- and succinate-induced OCR (FIGS. 5A and 5C). These studies established the optimal use of permeabilized cells for bioenergetics function assays (Salabei J K, Gibb A A, Hill B G. Comprehensive measurement of respiratory activity in permeabilized cells using extracellular flux analysis. Nat Protoc. 2014; 9(2):421-38).

Figures 6A, 6B, 6C, 6D:
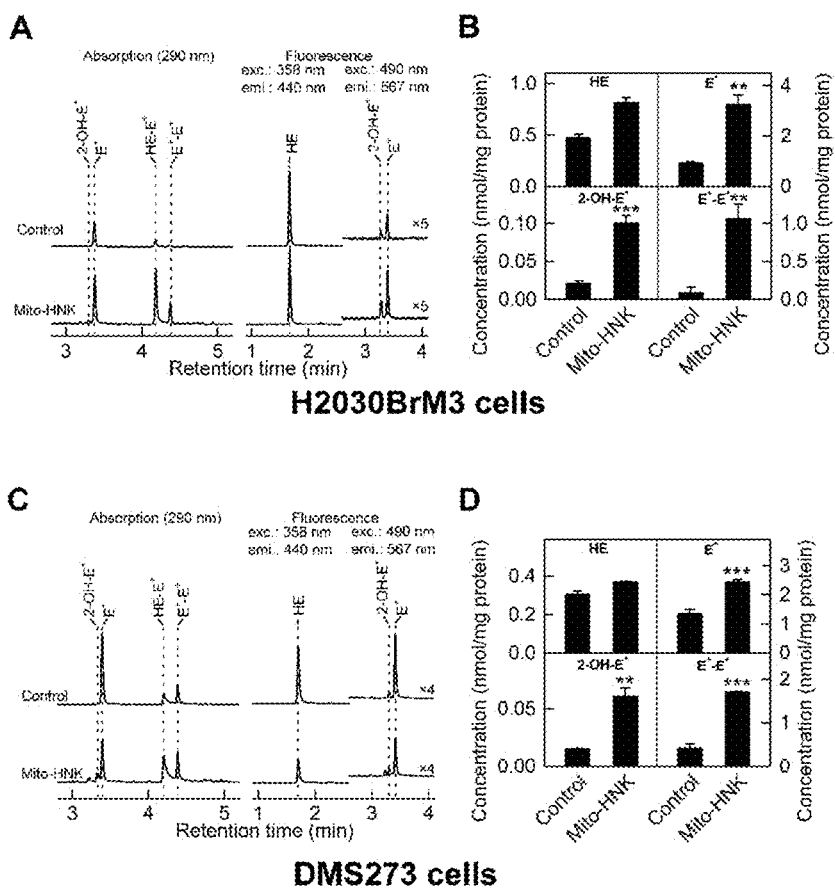
FIG. 6A-6D. Production of superoxide ($O_2^{\cdot-}$) and other oxidants by mito-honokiol. The effect of Mito-HNK on cellular ROS production, as measured by HPLC-based analyses of the oxidation of the HE probe. (A, C) HPLC traces recorded; (B, D) quantitative analyses of the products of HE oxidation. $p<0.01$, *$p<0.001$ in both H2030BrM3 (A,B) and DMS273 (C,D) cells.
Figures 7A, 7B:
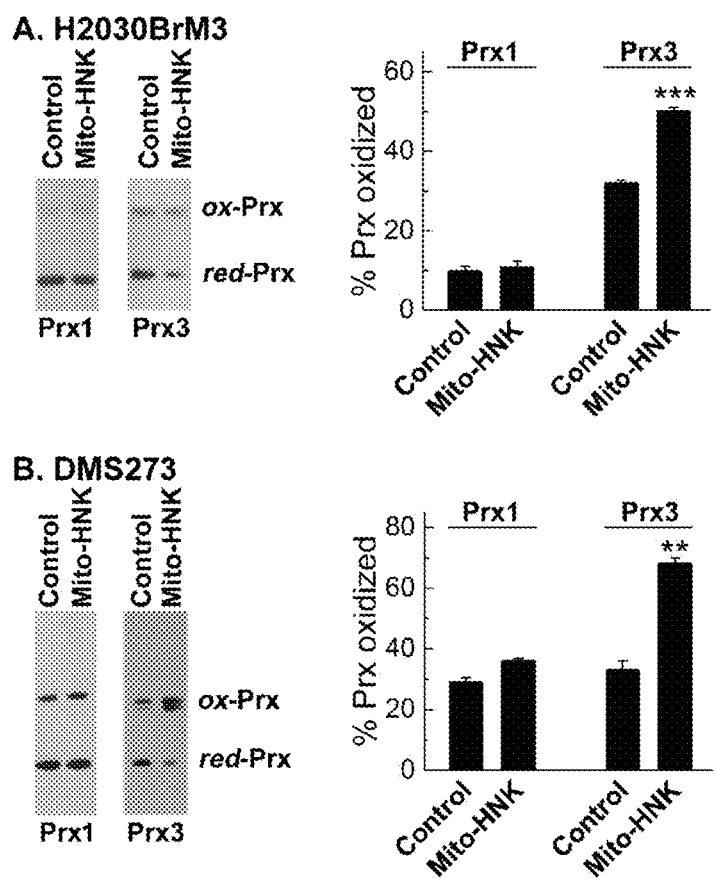
FIG. 7A-7B. Induction of mitochondrial peroxiredoxin-3 (Prx3) oxidation. 24-h treatment of H2030BrM3 (A) or DMS-273 (B) cells with Mito-HNK (0.2 μM and 0.4 μM, respectively) led to significant oxidation of mitochondrial Prx3, whereas the oxidation status of cytosolic Prx1 did not significantly change.

Effects of Mito-Honokiol in Production of Superoxide ($O_2^{\cdot-}$) and Mitochondrial Peroxiredoxin-3 Oxidation Many factors may be responsible for the Mito-HNK-induced activation of AMPK, one of the proposed mechanisms involving ROS generation (Hwang A B, Ryu E A, Artan M, Chang H W, Kabir M H, Nam H J, et al. Feedback regulation via AMPK and HIF-1 mediates ROS-dependent longevity in *Caenorhabditis elegans*. Proc Natl Acad Sci USA. 2014; 111(42)). We have shown that HNK induces mitochondrial ROS production (Pan i, Zhang O Liu Q, Komas S M, Kalyanaraman B, Lubet R A, et al. Honokiol inhibits lung tumorigenesis through inhibition of mitochondrial function. Cancer Prev Res (Phila). 2014; 7(11):1149-59). Because Mito-HNK is more potent than HNK in complex I inhibition (FIG. 5), we hypothesized that Mito-HNK would significantly increase ROS levels in lung cancer cells. Preliminary data show that Mito-HNK induces ROS formation in H2030-BrM3 cells. 2-OH-E$^+$, the $O_2^{\cdot-}$-specific product of hydroethidine (HE) oxidation, was increased in Mito-HNK (1 μM)-treated H2030-BrM3 and DMS-723 cells (FIG. 6). A strong induction of one-electron oxidation of HE with the formation of diethidium (E$^+$-E$^+$) also was observed, indicating that Mito-HNK induces generation of another, stronger oxidant in both H2030-BrM3 and DMS-273 cells (FIG. 7). To determine the possible direct targets of ROS stimulated upon inhibition of the mitochondrial complex I, we tested the oxidation status of cytosolic (Prx1) and mitochondrial (Prx3) peroxiredoxins. Results indicate that 24-h treatment of H2030-BrM3 and DMS-273 cells with Mito-HNK (0.2 and 0.4 μM, respectively) leads to significant oxidation of mitochondrial Prx3 with relatively a small extent of oxidation of cytosolic Prx1 (FIG. 7). This is consistent with Mito-HNK-induced mitochondrial ROS formation, with possible diffusion of a fraction of $O_2^{\cdot-}$ and/or $H_2O_2$ into the cytosol.

Figures 8A, 8B, 8C, 8D:
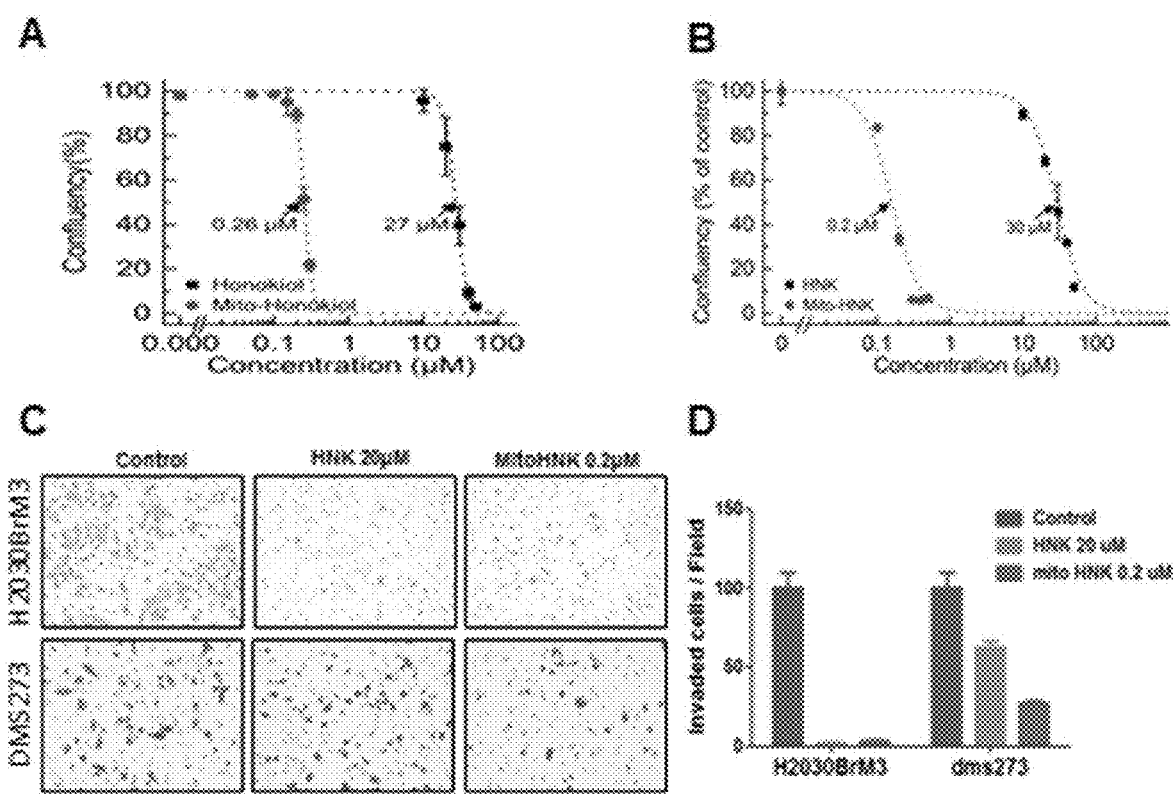
FIG. 8A-8D. Mito-honokiol exhibits inhibitory effects on lung cancer proliferation and invasion at submicromolar concentrations. Effects of Mito-HNK on the inhibition of lung cancer cells proliferation and invasion were examined in H2030-BrM3 NSCLC (A) and DMS-273 SCLC (B) cell lines. (A-B) H2030-BrM3 or DMS-273 cells were treated with control DMSO, various doses of HNK, or Mito-HNK for 24 hours, and cell proliferation was monitored with an IncuCyte Live imaging system. Mito-HNK significantly inhibited both H2030-BrM3 and DMS-273 cell proliferation in a dose-dependent manner, and Mito-HNK was more than 100-fold more potent than HNK in suppressing the proliferation of both H2030-BrM3 and DMS-273 SCLC cells. (C) Anti-invasive effects of Mito-HNK were examined via Boyden chamber invasion assay in H2030-BrM3 and DMS-273 cells. (D) Quantification of the invasion assay in H2030-BrM3 and DMS-273 treated with either control DMSO, HNK, or Mito-HNK indicate that Mito-HNK is about 100-fold more potent in the inhibition of lung cancer cells invasion.

Mito-HNK Exhibits Sub-Micromole Potency on Lung Cancer Proliferation and Invasion Next, we examined the anticancer effects of Mito-HNK compared to HNK in vitro. Various doses of HNK and Mito-HNK were treated in either H2030-BrM3 or DMS-273 cells, and the antiproliferative effects were monitored with an IncuCyte Live-Cell Imaging Analyzer. Both HNK and Mito-HNK show antiproliferative effects in H2030-BrM3 and DMS-273, as shown in FIGS. 8A and 8B, respectively. Interestingly, Mito-HNK inhibits cell proliferation at significantly lower doses than HNK with the IC50 values of 0.26 and 27 μM for H2030-BrM3 and 0.2 and 30 μM for DMS-273, respectively. Furthermore, we examined the anti-invasive effects of Mito-HNK in H2030-BrM3 and DMS-273 cells via a Boyden chamber invasion assay. Both cells were treated with vehicle control (DMSO), HNK (20 μM), and Mito-HNK (0.2 μM) for 36 hours, and invaded cells were determined. As shown in FIG. 8C, H2030-BrM3 and DMS-273 cells treated with both HNK and Mito-HNK have significantly fewer invasive cells than the vehicle-control-treated cells (FIGS. 8C and 8D). Antiproliferative (FIGS. 8A and 8B) and anti-invasive effects (FIGS. 8C and 8D) of MitoHNK in vitro demonstrated nearly a 100-fold increase in antiproliferative and anti-invasive potency by targeting HNK to mitochondria.

Figure 9A:
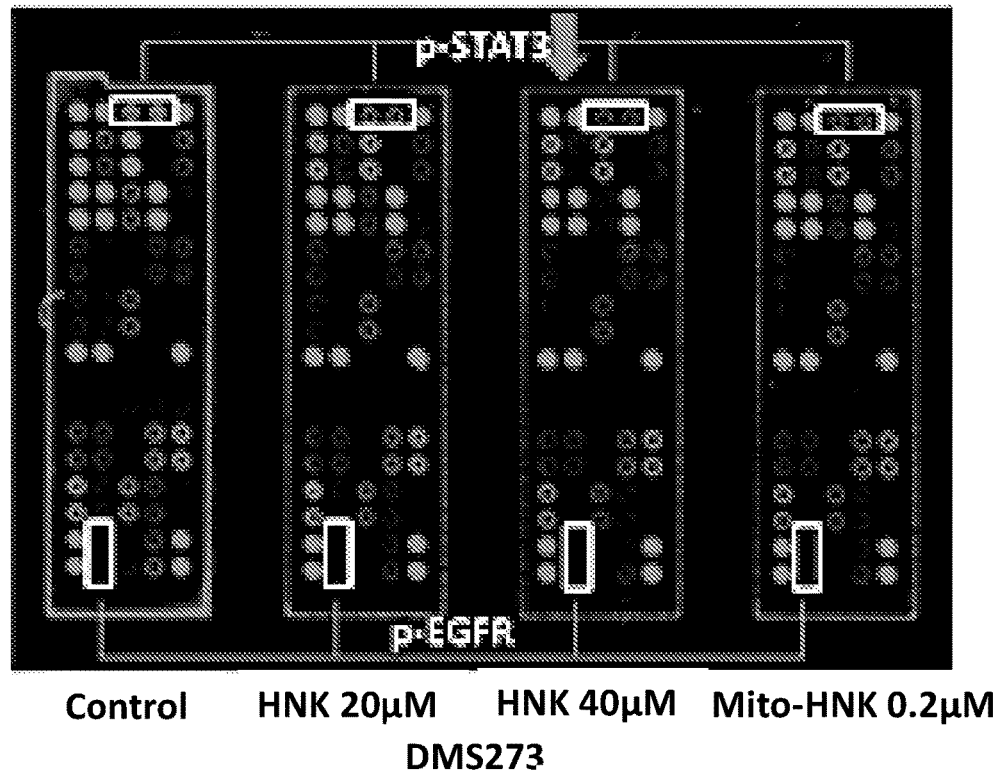
Figure 9B:
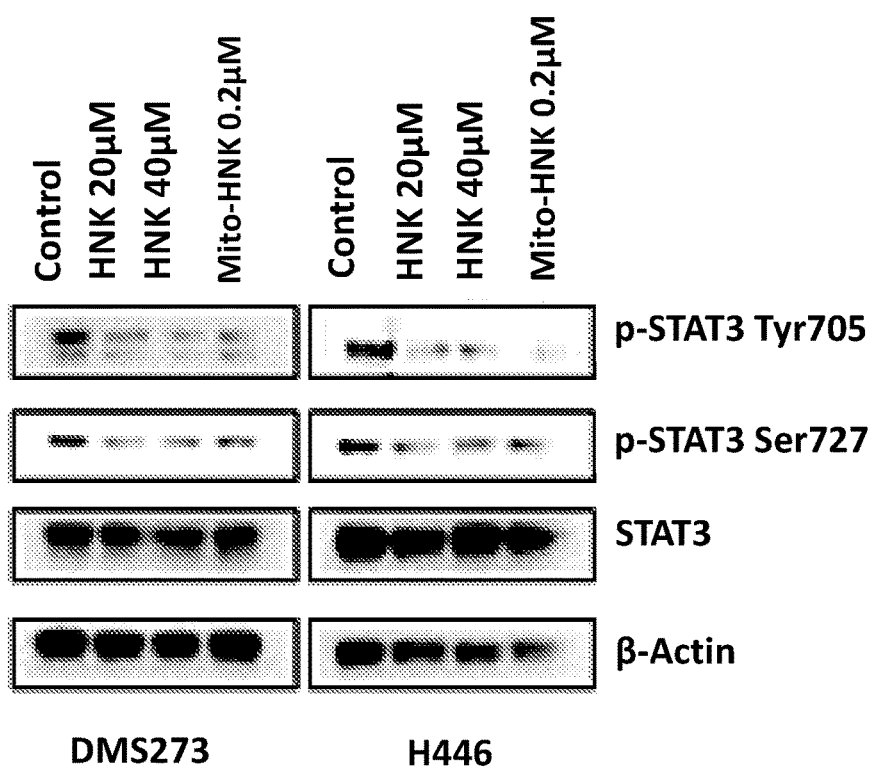

STAT3-Mitochondrial Complex I as Potential Target of Mito-HNK in the Inhibition of Lung Cancer Brain Metastasis Our results demonstrated the effects of Mito-HNK on the inhibition of lung cancer brain metastasis, but we wanted to look at the molecular mechanism of action behind the effects of Mito-HNK. We examined the potential mechanisms of Mito-HNK action on the inhibition of both brain metastatic lung cancer cell and SCLC cell progression via a PathScan receptor tyrosine kinases (RTK) assay (FIG. 9A), which has been used extensively to study mechanisms of action of candidate drugs (Vazquez-Martin et al., 2013). The PathScan RTK signaling array allows the examination of 28 different tyrosine kinase receptors as well as 11 downstream signaling nodes that frequently are deregulated in many types of cancer, including lung cancers. For the RTK signaling array, we treated DMS-273 cells with two different doses of HNK (10 µM and 20 µM) and Mito-HNK (0.2 µM) for six hours. The PathScan RTK signaling array results revealed that both HNK and Mito-HNK treatments dramatically decreased STAT3 phosphorylation levels compared to that of vehicle-control-treated cells (FIG. 9A), suggesting that STAT3 could be the major downstream target of Mito-HNK. We also observed similar pattern in H2030-BrM3 cells treated with HNK or Mito-HNK (Sup FIG. 9A). Then, we further validated the effects of HNK and Mito-HNK on STAT3 phosphorylation in DMS-273 cells via a Western blot analysis (FIG. 9B). Both cytoplasmic and mitochondrial STAT3 phosphorylation was significantly inhibited by Mito-HNK (FIG. 9B). Previously, HNK was reported to be effective in the treatment of head and neck squamous cell carcinoma by targeting the EGFR signaling pathway (Park et al., 2009). However, we observed that HNK only targets EGFR phosphorylation in the PC9-BrM3 cell line that harbors the EGFR mutation but not in the H2030-BrM3 that harbors the KRAS mutation (data not shown). Therefore, the effects of HNK on the EGFR signaling pathway could be in a manner specific to cell type, tissue, or driver mutation. Mito-HNK-inhibited STAT3 phosphorylation in PC9-BrM3 (EGFR mutation), H2030-BrM3 (KRas mutation), and DMS-273 (both EGFR and KRas wild type) regardless of the driver mutation status, suggesting that STAT3 could be a universal target of HNK via multiple receptor tyrosine kinases regardless of driver mutations in lung cancers.

Next, we validated the role of STAT in mediating anticancer effects of Mito-HNK in lung cancer cells. We used the shRNA approach to knock down endogenous STAT3 expression levels (FIG. 9C) and tested if the STAT3 knockdown decreased the anticancer effects of Mito-HNK. We found that the STAT3 knockdown significantly decreased the proliferation rate of DMS-273 cells compared to vector control infected cells (FIG. 9D). In addition, the fact that the STAT3 knockdown abrogated the antiproliferative effect of Mito-HNK in DMS-273 cells at the dose and time we tested indicates that STAT3 plays a significant role in mediating the anticancer effects of Mito-HNK.

We examined the toxicity of Mito-HNK in NHBE (normal lung epithelial cells) and confirmed that Mito-HNK has minimal toxic effects in normal lung cells, whereas it has great cytotoxic effects in lung cancer cells (FIG. 9E).

Mito-HNK Overcomes EGFR TKI Resistance in Lung Cancer

Figure 10B:
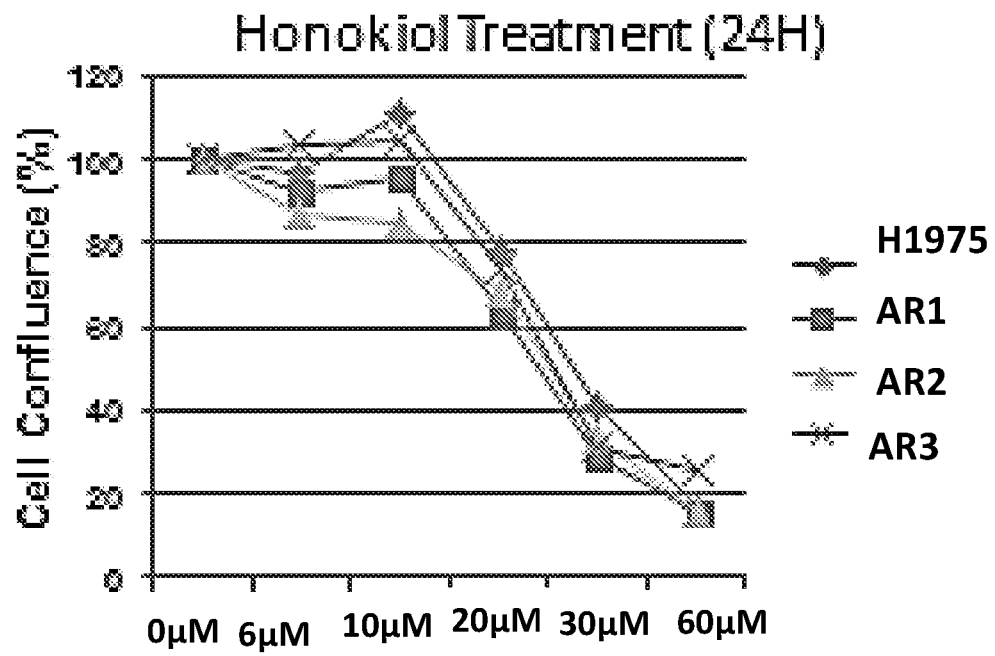
Figure 10C:
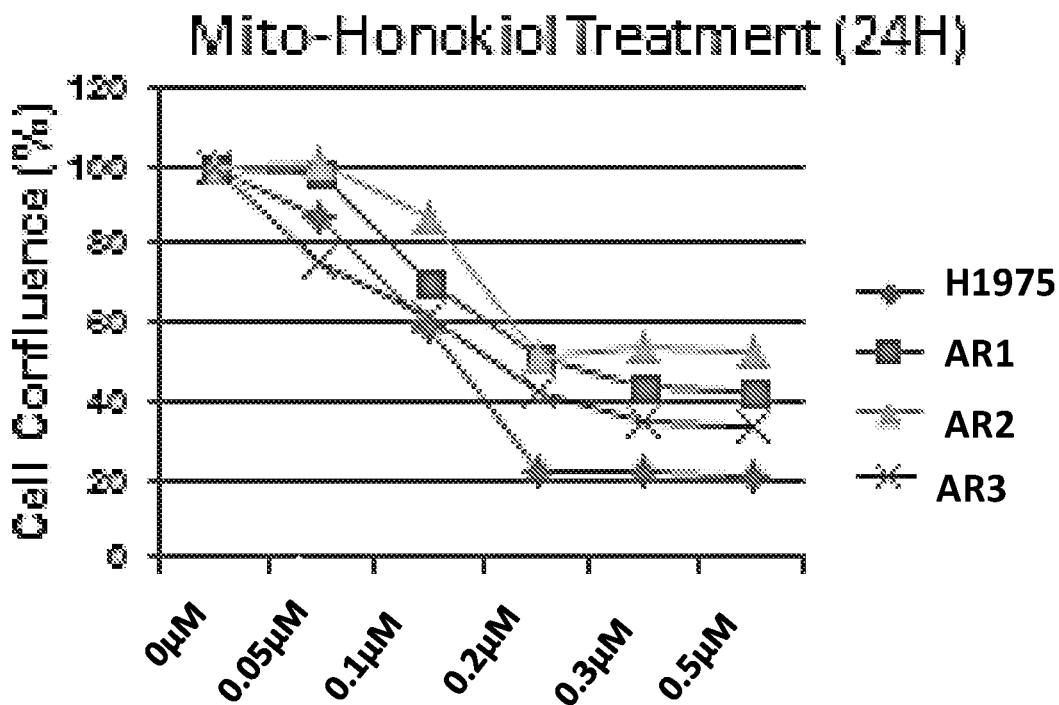

Mitochondrial ROS and STAT3 have been demonstrated to play a critical role in mediating cancer drug resistance in many types of cancers ((Alas and Bonavida, 2003; Bewry et al., 2008; Lee et al., 2014; Li et al., 2016; Nair et al., 2012; Yu et al., 2015). Therefore, we examined if Mito-HNK has an anticancer effect in afatinib, the EGFR TKI drug-resistant lung cancer cell lines (AR1, AR2, and AR3) that we previously developed (Lee et al., 2016). As shown in FIG. 10, both afatinib-sensitive H1975 cells and afatinib-resistant AR1, AR2, and AR3 cells were sensitive to HNK (FIG. 10B) and Mito-HNK (FIG. 10 A,C), with Mito-HNK showing efficiency at submicromolar concentrations.

Mito-HNK Exhibits AntiCancer Effects in Orthotopic Lung Cancer Model In Vivo

In both the H2030-BrM3 and DMS-273 orthotopic lung cancer models, lung tumors grew within the left lung and then spread within the lung, to the mediastinum, and to the chest wall of the left hemithorax. Mice did not show any observable side effects when treated with HNK or Mito-HNK. Remarkably, Mito-HNK significantly reduced lymphatic tumor metastasis compared to that of the groups treated with either vehicle control or HNK (FIG. 11).

Mito-HNK Inhibits both NSCLC and SCLC Brain Metastasis In Vivo

To investigate the effect of Mito-HNK on metastasis, a previously characterized experimental lung cancer brain metastasis model was used to generate brain metastases (Nguyen et al., 2009). We also generated GFP-luciferase expressing DMS-273 SCLC cells and confirmed brain metastasis of DMS-273 cells. We used an ultrasound-guided procedure to secure the precise injection of brain-seeking lung cancer cells into the left ventricle of NOD/SCID mice (FIG. 12A). One day after cell inoculation, the mice were randomly put into vehicle control, HNK, and Mito-HNK groups; tumor growth/brain metastases were monitored over 15 days using bioluminescence with an Xenogen IVIS-200. Mito-HNK-treated mice showed significantly fewer brain metastases compare to vehicle-control- or HNK-treated groups (FIG. 12C). At necropsy on 15 days post left-ventricle injection, brain metastases were qualified by ex vivo bioluminescence imaging, H&E and GFP staining as shown in FIG. 12B. Mito-HNK treatment decreased brain metastasis to nearly one-third of that of the control, as measured by luminescence intensity in the mouse brain. (FIGS. 12D,E). These data suggest that Mito-HNK could be a potent agent in preventing lung cancer brain metastases.

Discussion

Lung cancer is the leading cause of cancer mortality in the United States, and the metastatic spread of tumor cells to the brain is a major contributor to lung-cancer-related mortality (Goldberg et al., 2015; Jemal et al., 2010). A key approach to controlling this disease is the prevention of lung cancer development as well as its progression, especially metastases. Current available therapies to address CNS metastases include whole brain/CNS irradiation or surgical resection in eligible patients, and treatment with anti-EGFR agents in patients with EGFR mutations (Goldberg et al., 2015). However, these treatment options are available only after the diagnoses of brain tumors and at certain disease stages, whereas in many cases these metastasized tumors remain undiagnosed for a long time or are unable to be treated with either radiation therapy or surgery. Therefore, development of systematic prevention options to control metastases before diagnosis is necessary. Recently, we demonstrated the potent efficacy of HNK in the chemoprevention of lung tumor development in mice (Pan et al., 2014). Analysis of HNK's mechanism of action suggests that its effect is primarily mediated by inducing apoptosis through a mitochondria-dependent mechanism (Lin et al., 2012; Martin et al., 2013; Pan et al., 2014). Here, by using novel mitochondria-targeted HNK with a well-documented brain metastasis murine model, we report that Mito-HNK exerts an inhibition effect on lung cancer brain metastases, and we demonstrate HNK as a potential chemoprevention agent not only effective in primary lung tumor but also on lung cancer brain metastases.

Direct injection of tumor cells into the left ventricle is the most widely used brain metastasis model in rodents; though it bypasses precolonization steps such as dissemination, extravasation, and homing, it recapitulates the cancer cells' BBB crossing, invasion, and outgrowth in the brain microenvironment. Metastatic brain lesions vary from round, circumscribed lesions typical of those seen in humans, to very infiltrative tumor cells, which, if given time, will form typical round lesions; such lesions are ideal for use in evaluating the preventive effect of Mito-HNK on lung cancer metastasis. The brain homing H2030 and PC9 cell lines were developed to have 100% brain-metastatic potential, H2030 with a KRASG12C mutation (Phelps et al., 1996), and PC9 with an EGFRΔexon19 mutation (Koizumi et al., 2005). These cells were engineered to stably express GFP-luciferase fusion for real-time monitoring of metastatic tumor growth. In our study, we monitored metastatic tumor growth by both live animal imaging and endpoint ex vivo imaging. Also, tumor growth was validated with H&E and GFP staining assays, which consistently showed nearly 70% inhibition on brain metastases.

In this study, we represent that Mito-HNK effectively inhibits brain metastatic lung cancer proliferation, migration, and invasion mainly through inhibition of mitochondria complex I-STAT3 phosphorylation. HNK has been reported to target multiple signaling pathways including EGFR, MAPK, and PI3K-Akt (Crane et al., 2009; Deng et al., 2008; Garcia et al., 2008; Tse et al., 2005). Recently, SIRT3 and GRP78 also were suggested as potential binding targets of HNK in different tissue types (Martin et al., 2013; Pillai et al., 2015). Interestingly, STAT3 is a major downstream mediator of multiple receptor tyrosine kinase pathways (De Simone et al., 2015; Wu et al., 2014; Yau et al., 2005; Zhou et al., 2007).

In this study we also demonstrate that, regardless of EGFR mutation status, Mito-HNK decreased STAT3 phosphorylation in both PC9-BrM3 and H2030-BrM3 brain metastatic lung cancer cell lines. In addition, the knock down of endogenous STAT3 abrogated the antiproliferative, antimigratory, and anti-invasive effects of Mito-HNK in both brain metastatic lung cancer cell lines. Our data suggest that STAT3 could be a universal downstream target of Mito-HNK, regardless of the lung cancer's driver mutation status.

The development of new and effective therapies for patients with either brain metastatic NSCLC or highly metastatic SCLC is urgently needed. Targeting cancer metabolism is a novel therapeutic strategy to treat lung cancers. Here, we demonstrate a new mitochondria-targeted compound, Mito-HNK, to facilitate its delivery of HNK to mitochondria. We successfully demonstrate the therapeutic potential of Mito-HNK using both in vitro and in vivo models and determine its mechanism of action. The Mito-HNK provides novel preventive and therapeutic options for lung cancer patients with brain metastases.

Example 9: Additional In Vitro Testing

Figures 14A, 14B, 14C, 14D:
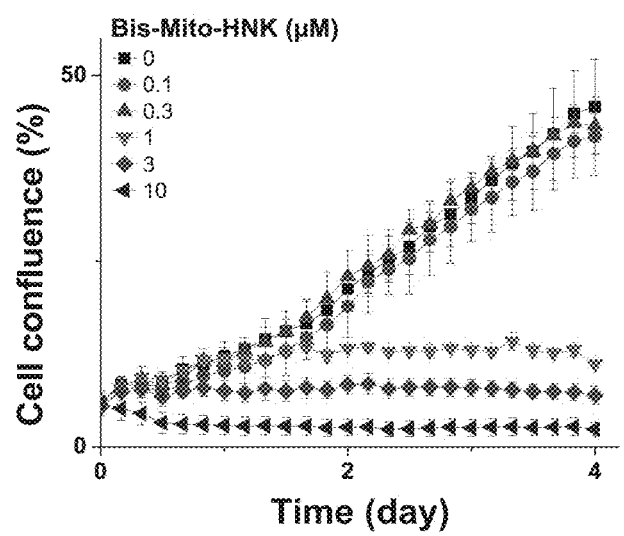
FIG. 14A-14D. Effects of mito-honokiol in a brain cancer cell line. The effects of Mito-HNK (14B and 14C) and Bis-Mito-HNK (14D) on U87 cells, a brain cancer cell line, is shown as compared with HNK alone (FIG. 14A).

Using similar methods as described in Example 8, Mito-HNK was tested in other tumor cell lines. FIG. 14B-D shows the effects of Mito-HNK (14B and 14C) and Bis-Mito-HNK (14D) on U87 cells, a brain cancer cell line, as compared with HNK alone (FIG. 14A). Thus, Mito-HNK can be used to reduce and inhibit brain cancer.

Figures 16A, 16B, 16C, 16D:
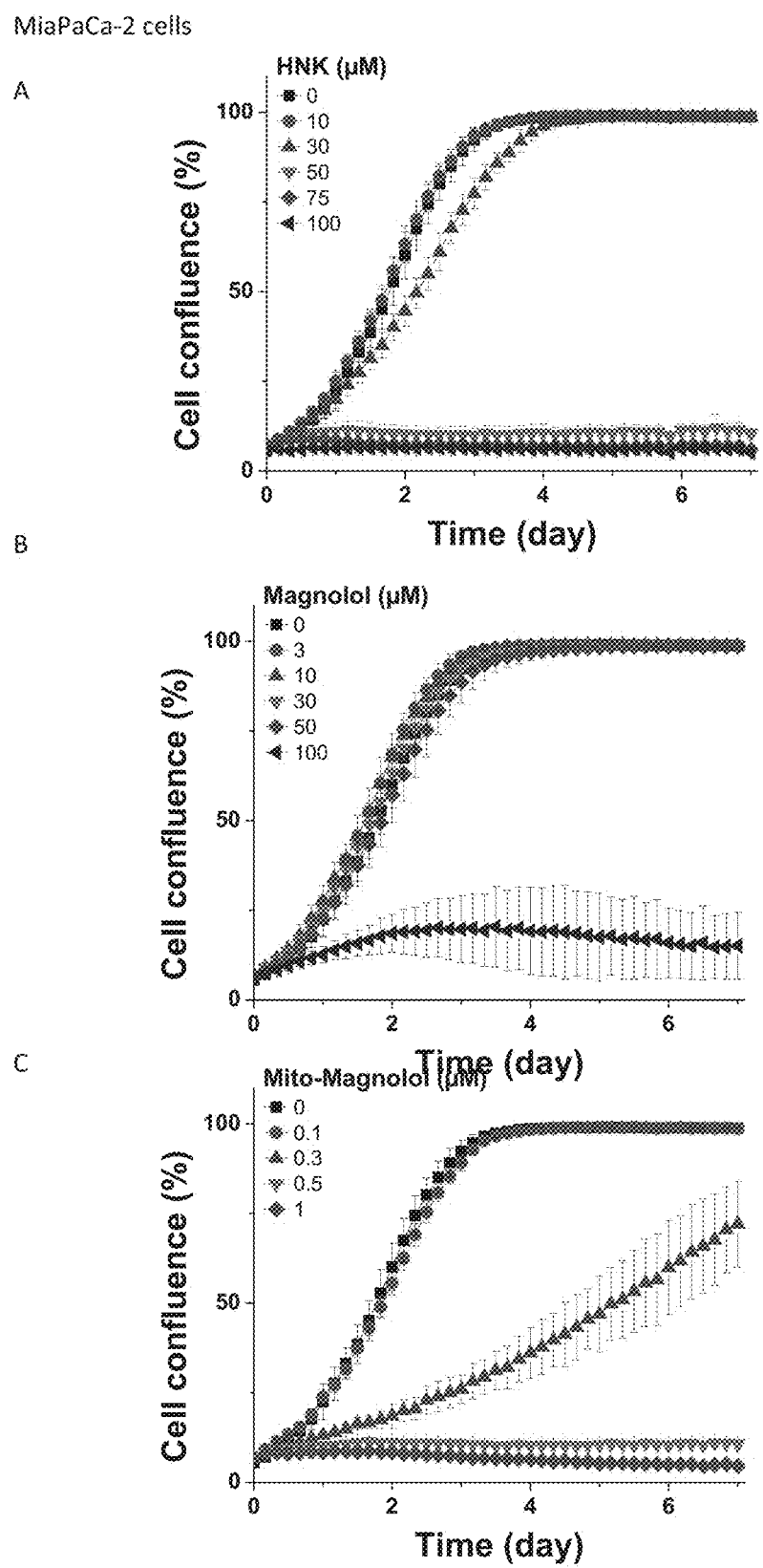
FIG. 16A-16B. In vitro effects of mito-magnolol. In vitro inhibition of cell growth for MiaPaCa cells for HNK alone (FIG. 16A), magnolol (FIG. 16B), as compared to mito-magnolol (FIG. 16C) and mito-phenyl-HNK (FIG. 16D).

FIGS. 15A and B demonstrates the effect of Mito-HNK as compared with HNK at two different concentrations, 0.2 μM (FIG. 15A) and 1 μM (FIG. 15B) in MiaPaCa-2 cells (pancreatic cancer cell line). Further, the combining the mito-honokiols of the present invention with antiglycolytic agents (e.g. 2-deoxyglucose) reduced the rate of proliferation of pancreatic cancer cells than either treatment alone, as shown for a number of different concentrations in FIG. 15C-F. FIG. 16 further demonstrates in vitro inhibition of cell growth for MiaPaCa cells for HNK alone (FIG. 16A), magnolol (FIG. 16B), as compared to mito-magnolol (FIG. 16C) and mito-phenyl-HNK (FIG. 16D).

FIGS. 17A and B show the effects of the combination of mito-honokiols with 2-deoxyglucose on total ATP levels in Capan-2 cells (pancreatic adenocarcinoma cell line).

EXAMPLES

The following examples are, of course, offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

Example 1. Development of OXPHOS Inhibitors for Use in Treatment of Cancer

This Example demonstrates methods of making mito-magnolol, and the ability of mito-magnolol to inhibit proliferation of both wild type and drug resistant melanoma in vitro. This Example further demonstrates that mito-magnolol compounds can stimulate ROS and cause oxidation of mitochondrial antioxidative enzyme in BRAFV600E inhibitor-resistant melanoma cells.

Synthesis of Mito-magnolol. Mito-magnolol was prepared by reacting 10-bromodecyltriphenylphosphonium bromide with magnolol in the presence of potassium carbonate in DMF (FIG. 29A). To a mixture of magnolol (0.2 g, 0.75 mmol) and anhydrous potassium carbonate (0.22 g, 1.5 mmol) in DMF (20 mL) was added 10-bromodecyltriphenylphosphonium bromide (0.42 g, 0.75 mmol) at 0° C. The mixture was stirred at 35° C. for 24 hours. The residue was taken up into water and extracted with $CH_2Cl_2$. The organic layer was dried over $Na_2SO_4$, and the solvent was removed under reduced pressure. Ether was added to precipitate the crude product. Purification by flash chromatography using the following gradient from $CH_2Cl_2$ (100%) to $CH_2Cl_2$/EtOH (80/20) as eluent delivered the corresponding Mito-magnolol (200 mg, 35% yield) and the Mito-bis-magnolol (80 mg, 14% yield) as white solids.

Figure 19:
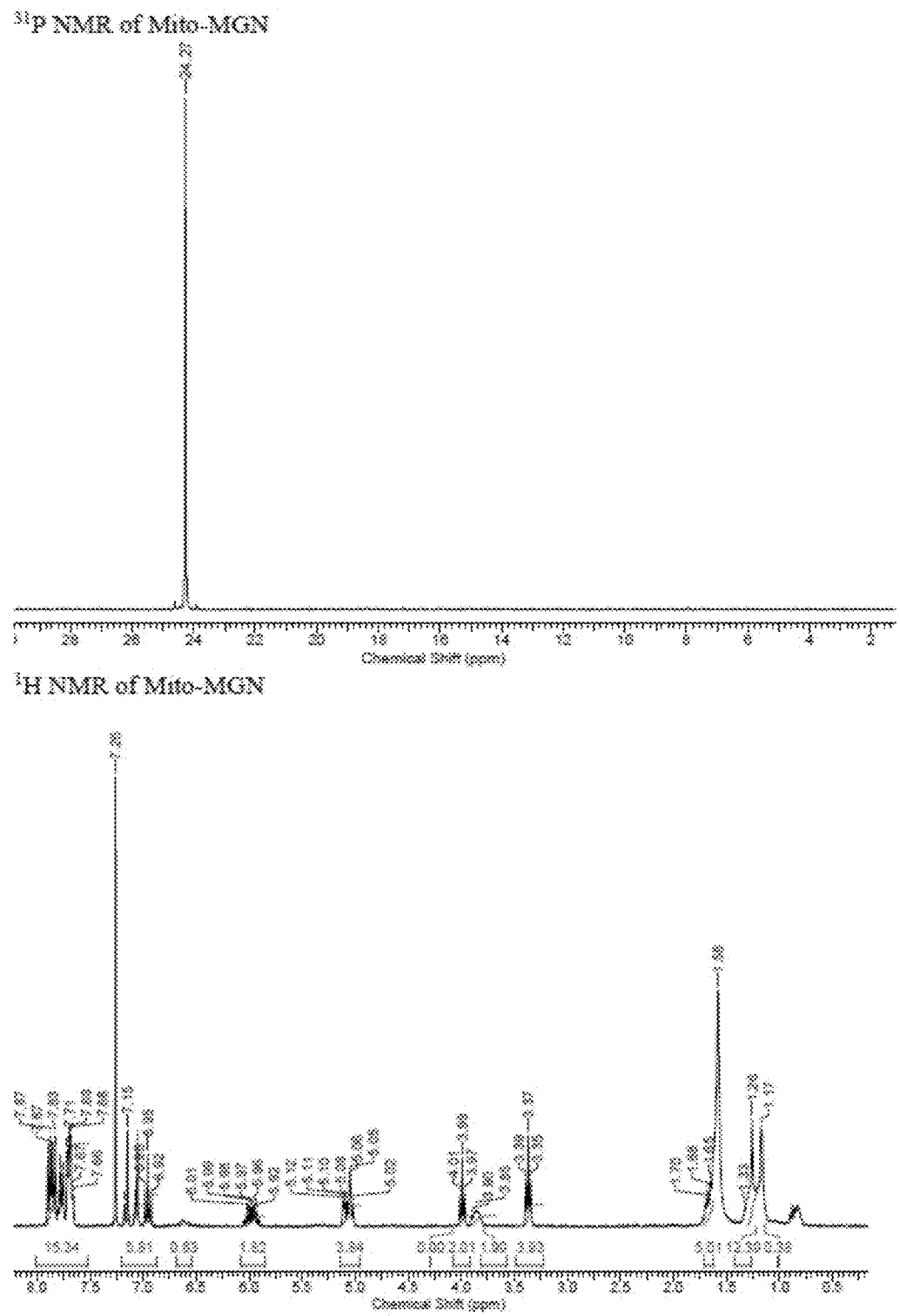
FIG. 19 shows NMR spectra of Mito-magnolol (Mito-MGN) and Mito-methylmagnolol (Mito$_{Me}$-MGN).
Figure 19:
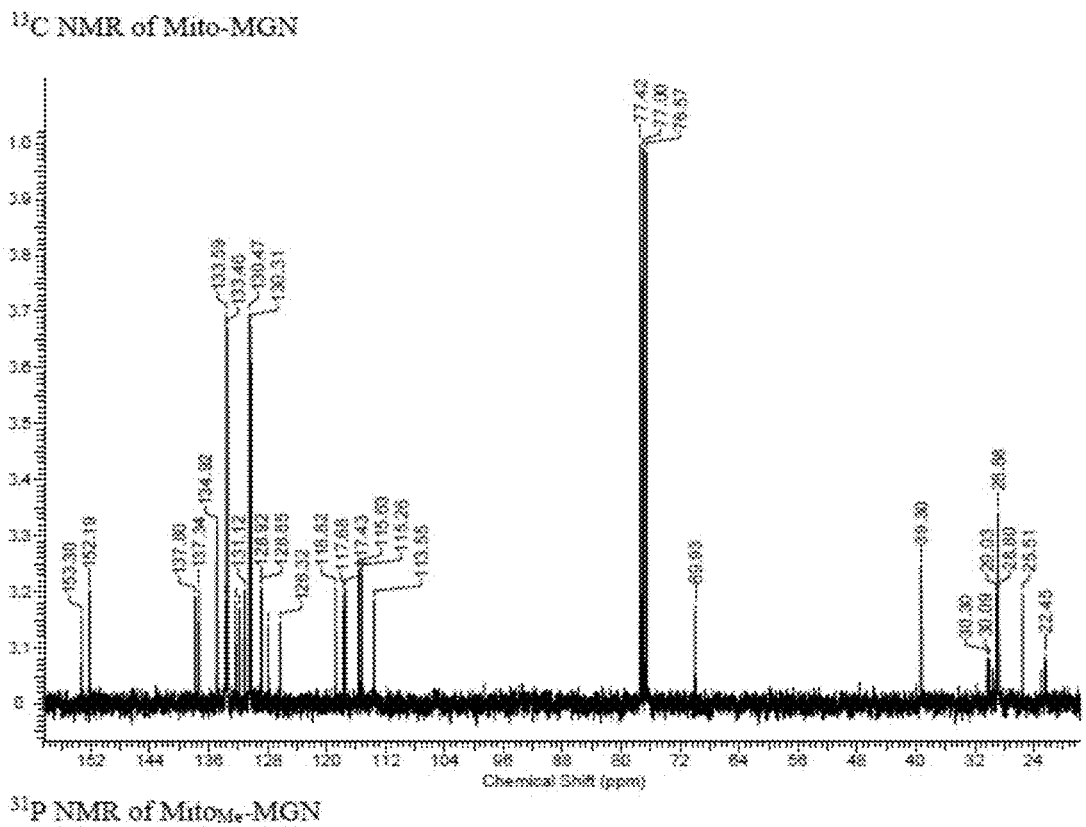
Figure 19:
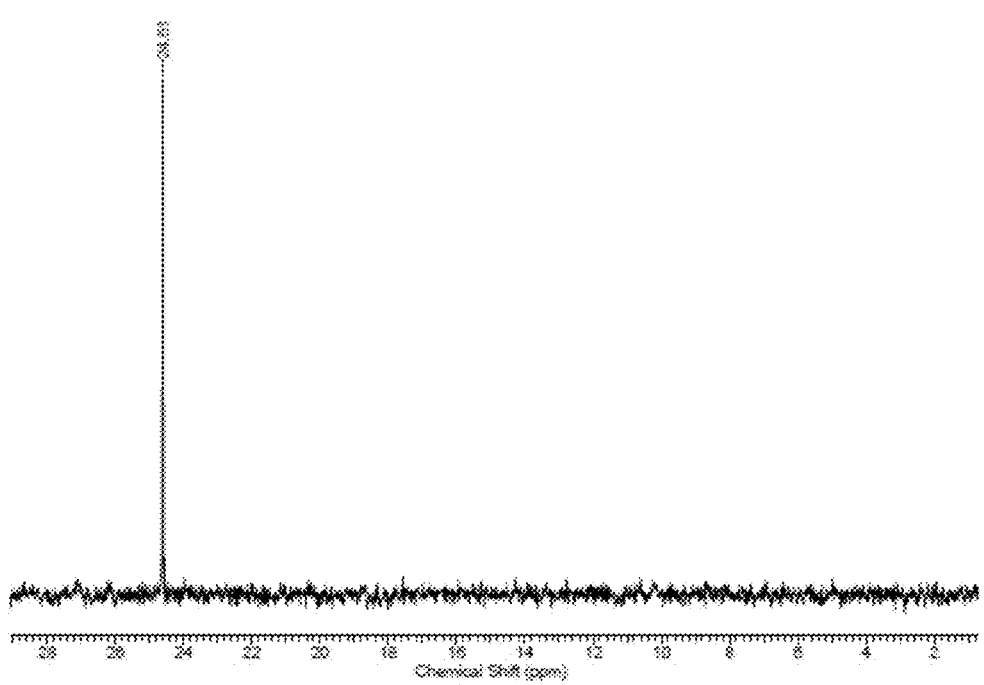
Figure 19:
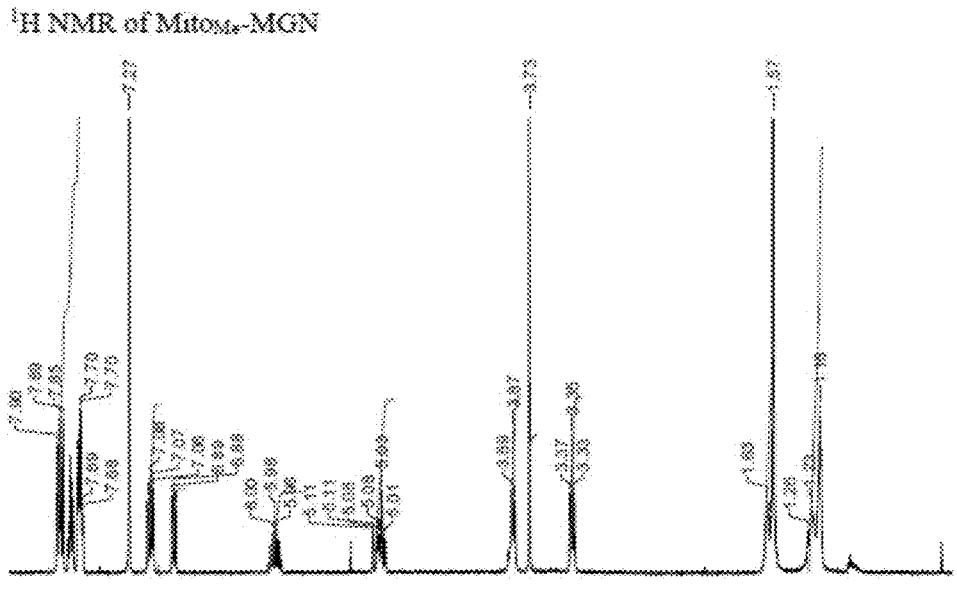
Figure 19:
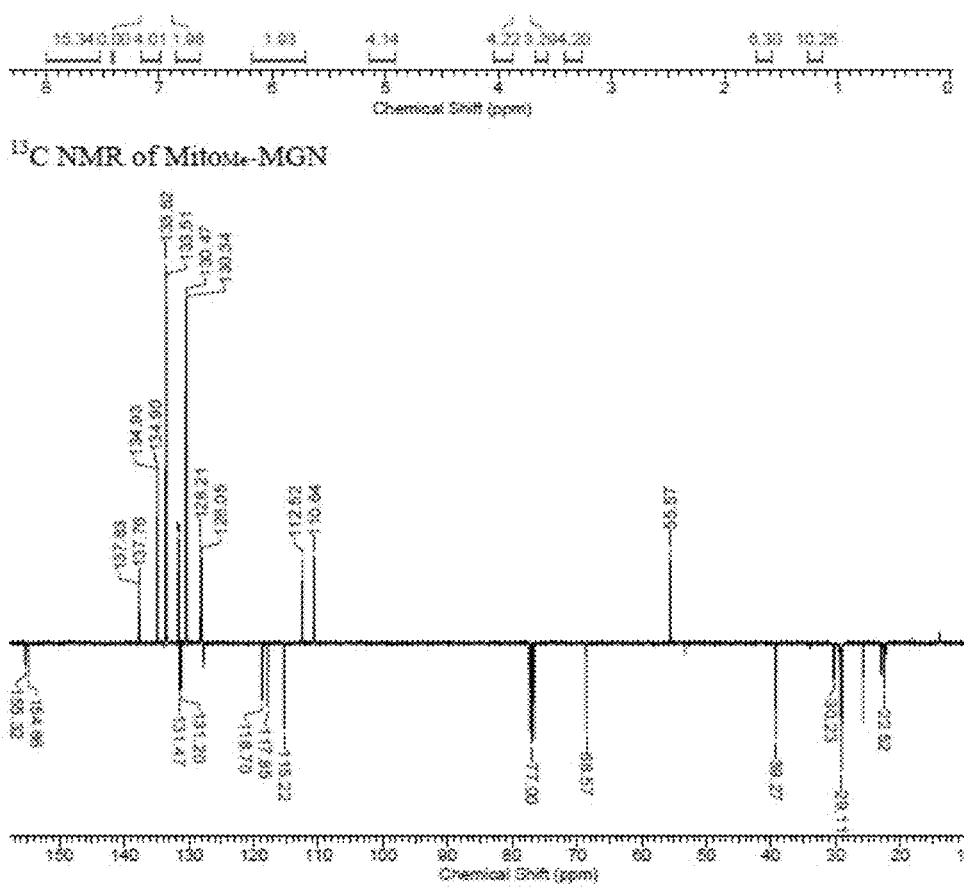

FIG. 19 shows the NMR of Mito-magnolol. HRMS calculated for Mito-magnolol C46H52O2P $[MH]^+$: 667.3699, found: 667.3699 31P (400.13 MHz, CDCl3) δ 24.27. 1H NMR (400.13 MHz, CDCl3) δ 7.80-7.65 (15H, m), 7.18-6.92 (6H, m), 6.06-5.86 (2H, m), 5.12-5.02 (4H, m), 3.99 (2H, t, J=6.5), 3.90-3.79 (2H, m), 3.37 (4H, t, J=6.9), 1.70-1.50 (4H, m). 1.39-1.13 (12H, m). (75 MHz, CDCl3) δ 153.3, 152.2, 137.8, 137.3, 133.9, 134.8, 133.6, 133.4, 132.4, 131.8, 131.1, 130.5, 130.3, 128.9, 128.8, 127.9, 126.3, 118.8, 117.7, 117.4, 115.6, 115.3, 113.6, 69.9, 39.3, 39.2, 30.3, 30.1, 29.0, 28.8, 25.5, 23.2, 22.5, 22.4, 22.3.

Synthesis of Mito$_{Me}$-magnolol.

Me-magnolol and DiMe-magnolol were prepared by reacting methyl iodide with magnolol in the presence of potassium carbonate in DMF. Williamson reaction of 2-O-methylmagnolol and 10-bromodecyl-triphenylphosphonium bromide in the presence of potassium carbonate led to Mito$_{Me}$-magnolol (FIG. 29B). To a mixture of 2-O-methylmagnolol (0.3 g, 1 mmol) and anhydrous potassium carbonate (0.3 g, 2 mmol) in DMF (4 mL) was added 10-bromodecyltriphenylphosphonium bromide (0.6 g, 1 mmol). The mixture was stirred at 40° C. for 18 h. 20 mL of water was added and the product was extracted with $CH_2Cl_2$ (80 mL). The organic layer was dried over $Na_2SO_4$, and the solvent was removed under reduced pressure. The product is precipitated with $Et_2O$. Purification by flash chromatography ($CH_2Cl_2$ and $CH_2Cl_2/EtOH$) delivered the corresponding $Mito_{Me}$-magnolol as a white solid (0.5 g, 62% yield).

FIG. 19 shows the NMR of $Mito_{Me}$-magnolol. HRMS calculated for MitoMe-MGN C47H54O2P [M]$^+$: 681.3856, found: 681.3857. 31P (400.13 MHz, CDCl3) δ 24.61. 1H NMR (400.13 MHz, CDCl3) δ 7.90-7.65 (15H, m), 7.07 (4H, 2dd, J=2.3, 8.3; 2.1, 5.6), 6.87 (2d, 2H, J=5.6; 5.8), 6.04-5.92 (2H, m), 5.10-4.98 (4H, m), 3.91-3.85 (4H, m), 3.73 (3H, s), 3.41-3.35 (4H, m), 1.67-1.59 (6H, m), 1.25-1.10 (10H, m). 13C NMR (75 MHz, CDCl3) δ 155.3, 154.8, 137.8, 137.7, 134.93, 134.90, 133.6, 133.5, 131.7, 131.5, 131.4, 131.2, 130.5, 130.3, 128.2, 128.0, 118.7, 117.8, 115.3, 115.2, 112.5, 110.6, 68.6, 55.6, 39.3, 30.4 (d, J=15.4), 29.3, 29.1, 29.1, 29.0, 22.8 (d, J=45.5), 22.4 (d, J=4.5).

Figure 30:
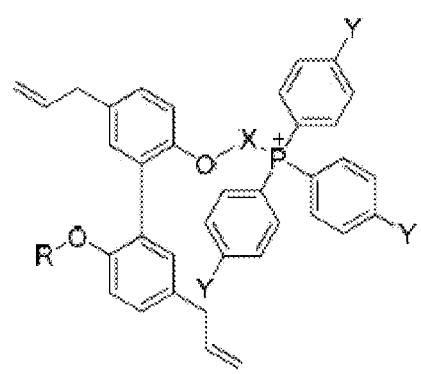
FIG. 30 demonstrates the generic structure of mito-magnolol.

FIG. 30 gives the generic structure of Mito-MGN derivatives that can be prepared using this procedure.

The MitoPEG-MGN compounds of the present invention can be synthesized according to the following reactions:

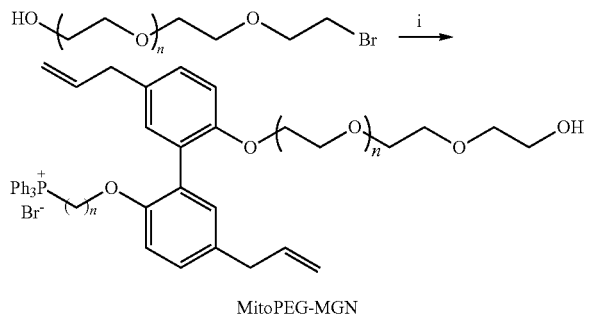

MitoPEG-MGN
Reagents and conditions: i, Mito$_n$-MGN, K$_2$CO$_3$, DMF.

The MitoPhen-MGN compound of the present invention can be synthesized according to the following reactions:

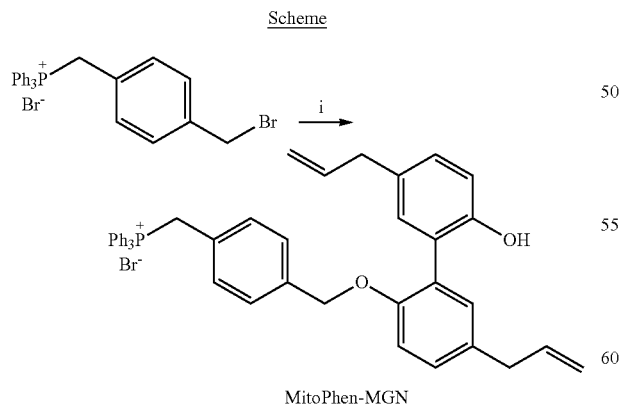

MitoPhen-MGN
Reagents and conditions: i, MGN, K$_2$CO$_3$, DMF.

The MitoCy-MGN compound of the present invention can be synthesized according to the following reactions:

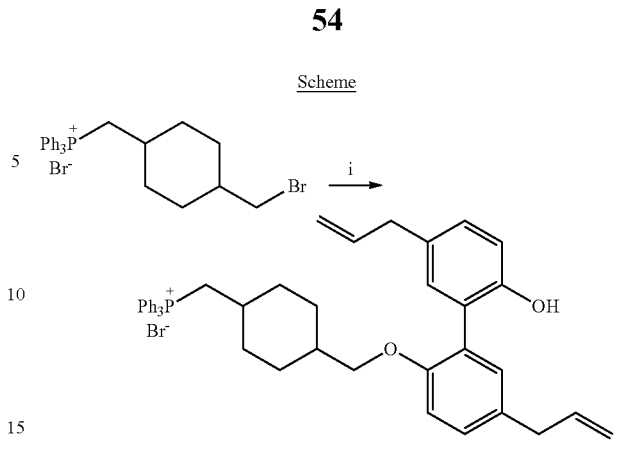

MitoCy-MGN
Reagents and conditions: i, MGN, K$_2$CO$_3$, DMF.

The Mito$_{Me}$-MGN compounds of the present invention can be synthesized according to the following reactions:

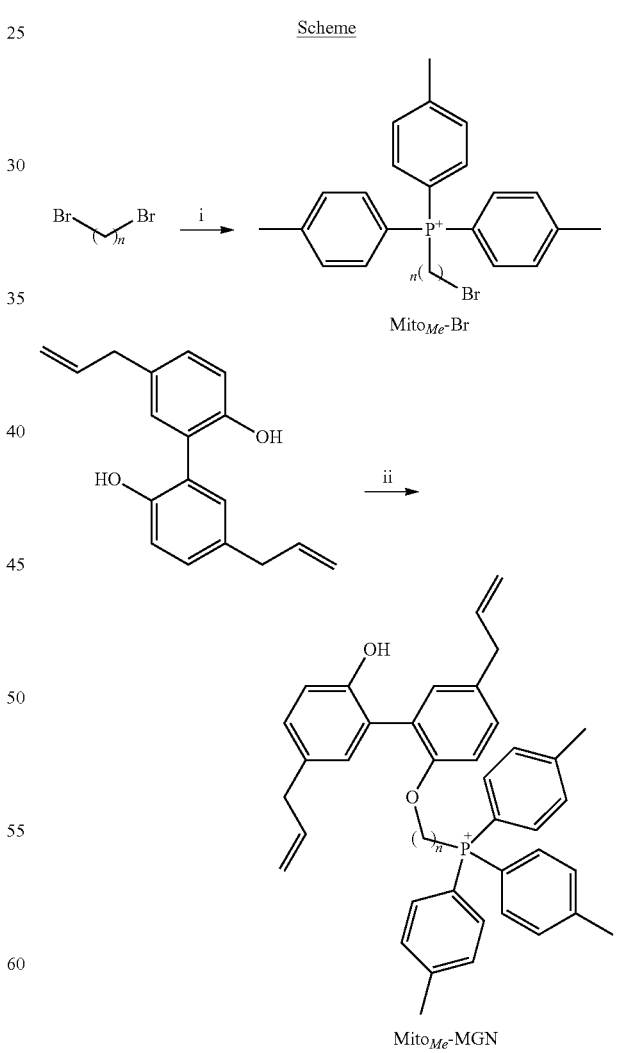

Mito$_{Me}$-MGN
Synthesis of Mito$_{Me}$-MGN derivatives. Reagents and conditions: i, tri-p-tolylphosphine, neat, 80° C.; ii, Mito$_{nMe}$-Br, K$_2$CO$_3$, DMF.

The Mito$_{OMe}$-MGN compounds of the present invention can be synthesized according to the following reactions:

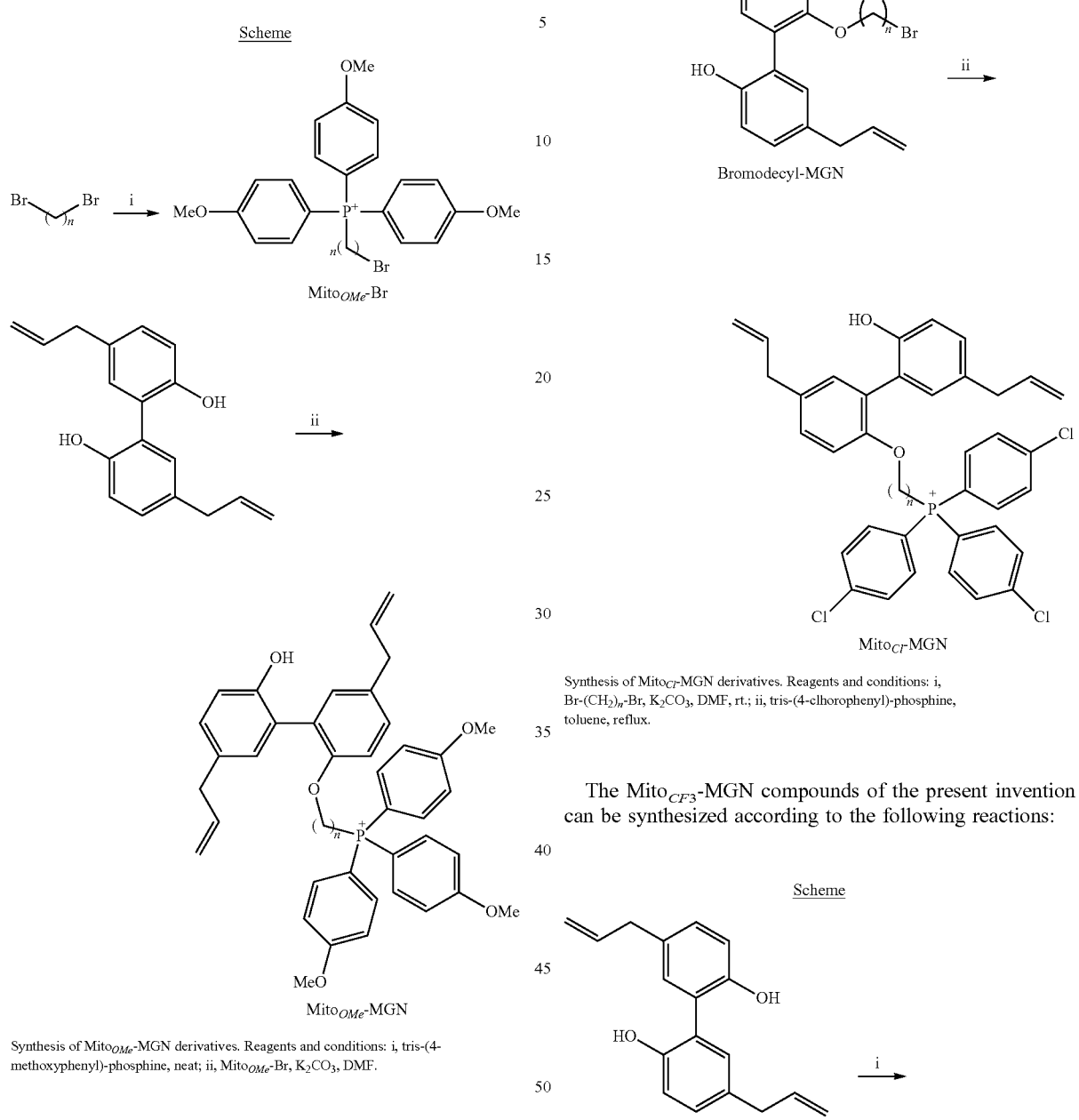

Synthesis of Mito$_{OMe}$-MGN derivatives. Reagents and conditions: i, tris-(4-methoxyphenyl)-phosphine, neat; ii, Mito$_{OMe}$-Br, K$_2$CO$_3$, DMF.

The Mito$_{Cl}$-MGN compounds of the present invention can be synthesized according to the following reactions:

Synthesis of Mito$_{Cl}$-MGN derivatives. Reagents and conditions: i, Br-(CH$_2$)$_n$-Br, K$_2$CO$_3$, DMF, rt.; ii, tris-(4-chlorophenyl)-phosphine, toluene, reflux.

The Mito$_{CF3}$-MGN compounds of the present invention can be synthesized according to the following reactions:

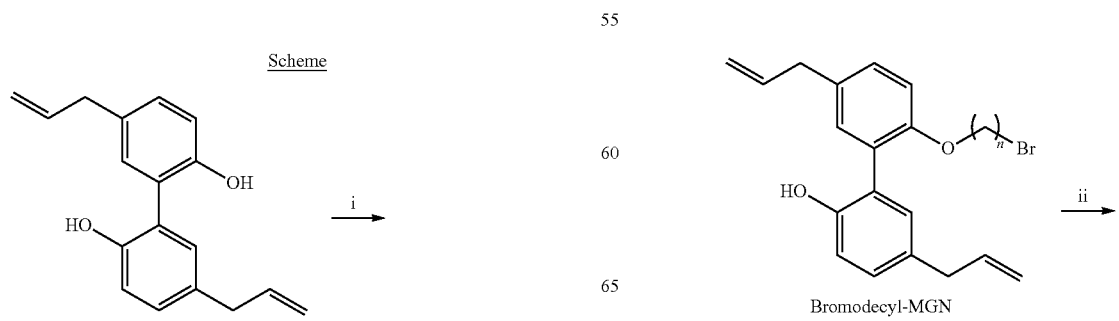

-continued

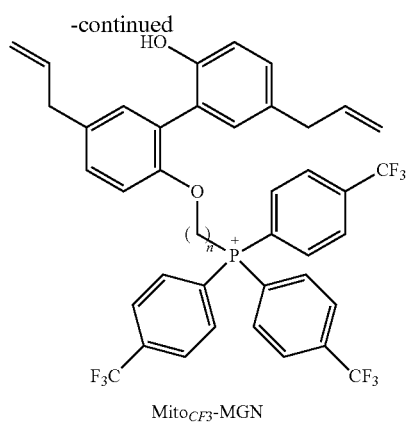

Mito$_{CF3}$-MGN

Synthesis of Mito$_{CF3}$-MGN derivatives. Reagents and conditions: i, Br-(CH$_2$)$_n$-Br, K$_2$CO$_3$, DMF, rt., 33%; ii, tris-[4-(trifluoromethyl)phenyl]-phosphine, toluene, reflux.

The Mito$_n$-MGN2 compounds of the present invention can be synthesized according to the following reactions:

Scheme

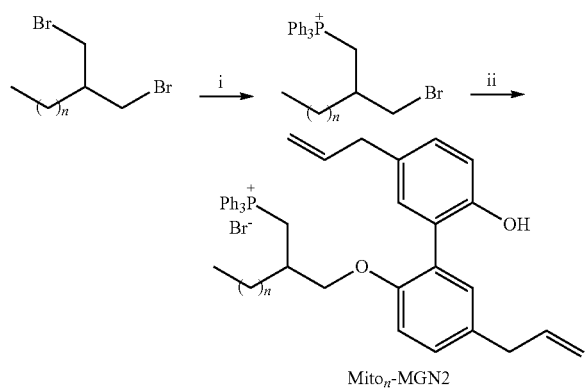

Mito$_n$-MGN2

Synthesis of Mito$_n$-MGN2 derivatives. Reagents and conditions: i, PPh$_3$, neat; ii, Magnolol, K$_2$CO$_3$, DMF, 40° C.

Generation of PLX4720-Resistant Melanoma Cell Line.

Figure 20:
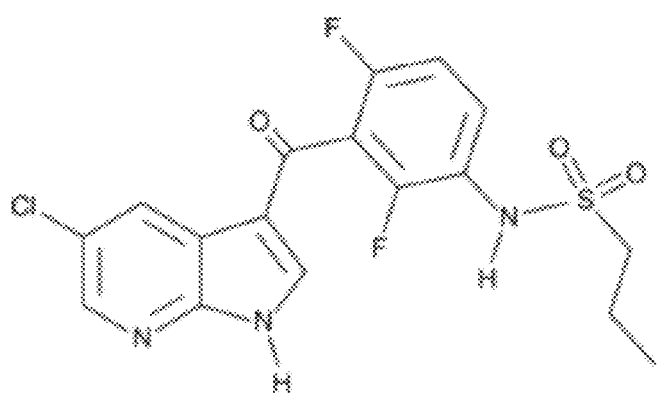
FIG. 20 shows the chemical structure of PLX4720 BRAF inhibitor.

Mutations in the BRAF kinase, especially the mutation BRAFV600E, contribute to melanoma. This mutation is not effectively targeted by inhibitors of wild type BRAF. PLX4720 (FIG. 20) has been used as a highly selective inhibitor of BRAFV600E (or also Raf Kinase inhibitor V). PLX4720 was found to be much less effective against wild type BRAF and induces cell cycle arrest and apoptosis in melanoma cells expressing BRAF mutation.

To establish PLX4720-resistant melanoma cell line, UACC-62 cells (ATCC) were continuously exposed to increasing concentrations of PLX4720 (1-20 µM) for six months until the logarithmic growth resumed. PLX4720-containing media were replaced twice a week. Resistant cell line (UACC-62R) was maintained in routine culture in the presence of 20 µM PLX4720. FIGS. 21A and 21B show the effect of PLX4720 on proliferation of UACC-62-WT and UACC-62-R cells. FIG. 21C shows the phase contrast images obtained after six days of treatment with 0.5-10 µM PLX4720 of the WT and resistant cells. As can be seen, there are considerably fewer WT cells compared to resistant cells in the presence of 10 µM PLX4720. FIG. 21D shows the IC$_{50}$ values (concentration at which 50% of cell proliferation is inhibited). These results clearly show the difference in sensitivity of UACC-62-WT and UACC-62-resistant cells to PLX4720.

Metabolic Reprogramming in Drug-Resistant Melanoma Cells: Enhanced OXPHOS.

Melanoma cells harboring BRAF oncogenic mutations use aerobic glycolysis (the Warburg effect) to meet their energy demands. However, cells with acquired resistance to BRAF inhibitors exhibit metabolic reprogramming, i.e., decreased glycolysis and a compensatory activation of mitochondrial OXPHOS (FIG. 21E, red arrow from WT to R). One reason for the acquired resistance to PLX4720 is the adaptive change from glycolysis to OXPHOS. The two-dimensional map of oxygen consumption rate (OCR) and extracellular acidification rate (SCAR), quantified as proton production rate (PPR), shows a ~55% increase in OCR and an 11% decrease in PPR, in UACC-62-R cells (FIG. 21E). Mito-MGN treatment minimally affected glycolysis in WT and resistant cells, while significantly inhibiting OXPHOS in both cell lines (FIG. 21E, blue).

Mito-MGN Inhibits Mitochondrial Complex I Activity.

We used a Seahorse XF96 Analyzer to measure OCR, a readout of mitochondrial respiration, and SCAR, a surrogate marker for glycolysis, in real time. OCR is measured after adding substrates and inhibitors of complexes I-IV. In preliminary studies, Mito-MGN inhibited complex I activity in both WT and resistant cells (FIG. 21F). The IC$_{50}$ to inhibit complex I-mediated respiration (1 h Mito-MGN treatment) was 0.35 µM for UACC-62-WT cells, and 0.66 µM for UACC-62-R.

Mito-Magnolol Inhibits Proliferation of Both Wild Type and Drug Resistant Melanoma Cells.

Figures 22A, 22B, 22C, 22D:
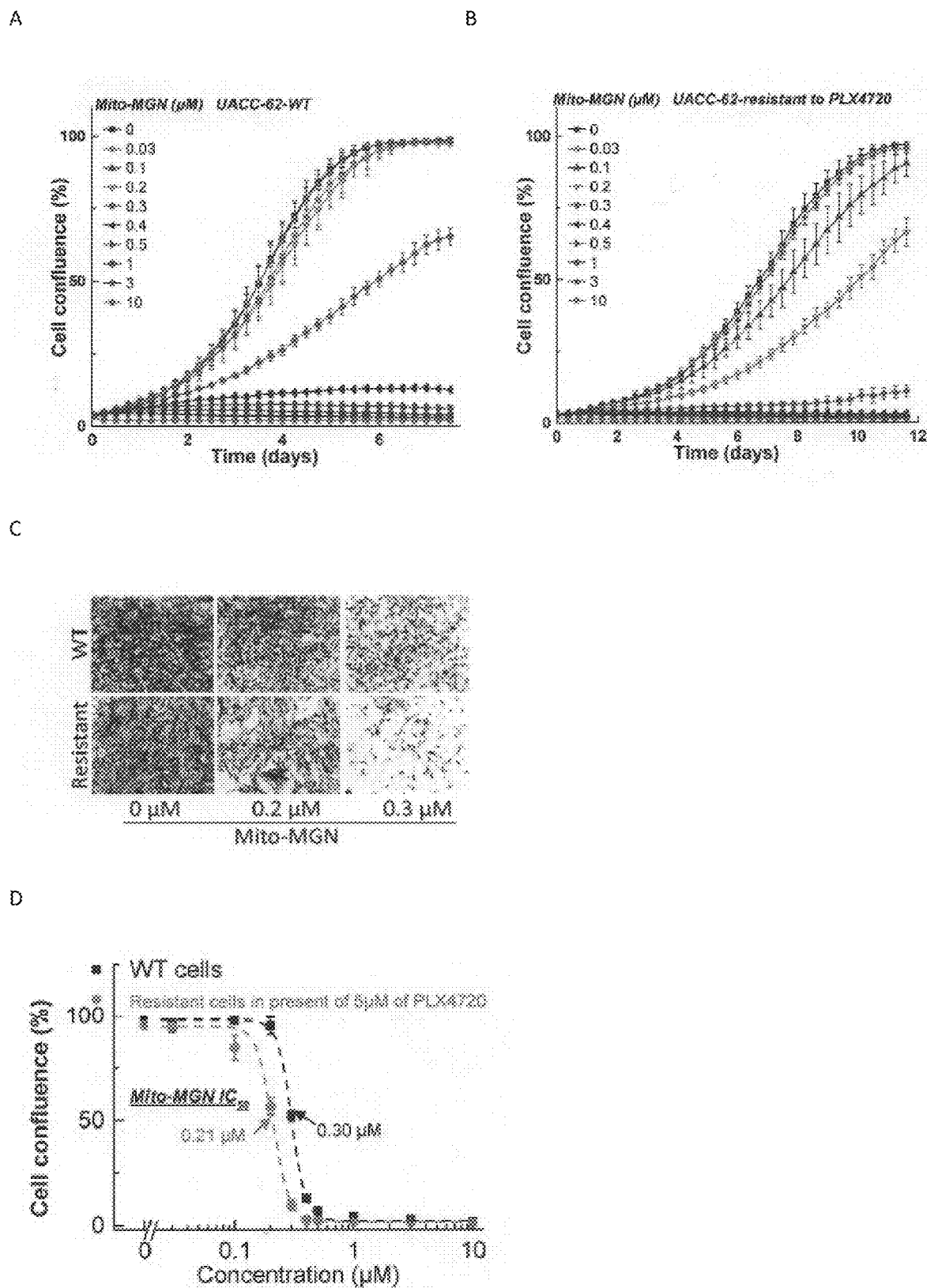
FIG. 22A-22D demonstrates the effect of Mito-MGN on proliferation of UACC-62-WT cells and UACC-62-R cells. UACC-62-WT cells (A) or UACC-62-R cells (B) were treated with Mito-MGN as indicated. Cell proliferation was monitored in real time with the continuous presence of indicated treatments until the end of each experiment. (C) Representative images shown are the segmentation of phase contrast images (segmentation mask illustrated in black). (D) The cell confluence (as control groups reach 95% confluency) is plotted against Mito-MGN concentration. Dashed lines represent the fitting curves used to determine the IC$_{50}$ values.

FIGS. 22A and 22B show the effect of Mito-magnolol on proliferation of UACC-62-WT and UACC-62-R cells. Cell proliferation was monitored in real time for cells incubated continuously under treatment conditions as shown. FIG. 22C shows the phase contrast images obtained after six days of treatment of WT and PLX4720-resistant cells in the presence of 0.1-0.3 µM of Mito-magnolol. As can be seen, both cell lines were exquisitely sensitive to Mito-magnolol treatment. FIG. 22D shows the IC$_{50}$ values of Mito-magnolol in WT and resistant cells. Results show that Mito-magnolol is effective in inhibiting the proliferation of drug resistant melanoma cells (FIG. 22).

Mito-magnolol inhibitory effect in drug resistant melanoma cells was a totally unexpected result. Melanoma cells use metabolic reprogramming as a survival mechanism. Melanoma cells harboring BRAF mutations or BRAFV600E melanomas use aerobic glycolysis (the Warburg effect) to meet their energetic demands. Selective inhibitors of BRAF mutation (e.g., vemurafenib or PLX4032) that inhibit glycolysis cause a compensatory activation of oxidative metabolism, stimulating energy production through mitochondrial oxidative phosphorylation. It is believed that this adaptive change—from glycolysis to OXPHOS—is one of the reasons for the acquired resistance to vemurafenib. The vemurafenib-resistant melanoma cells exhibited increased oxidative stress and reactive oxygen species. One of the new strategies that was proposed to enhance the killing of vemurafenib-resistant cells involved the use of pro-oxidants or pro-oxidative drugs such as elesclomal (22). It was also suggested that mitochondrial pro-oxidants may have a clinical potential for treatment of drug resistant melanomas. Antioxidants (compounds or drugs that quench formation of oxidants and reactive oxygen species) reversed the effect of pro-oxidative drugs in vemurafenib-resistant melanoma cells.

Mito-magnolol is a structurally modified analog of magnolol, a naturally occurring bioactive polyphenol that has been shown to have an antioxidative and anti-inflammatory property (23,24). Mito-magnolol is synthesized by conjugating a triphenylphosphonium moiety to the phenolic hydroxyl group of magnolol. Magnolol elicits antioxidant behavior in both chemical and cellular systems. Magnolol inhibits oxidant-induced lipid peroxidation, a pro-oxidative process. Previously, it has been shown that Mito-Q, a triphenylphosphonium based modification of a naturally occurring antioxidant co-enzyme Q, shows potent antioxidant property in mitochondria (25).

Mito-magnolol stimulates ROS and causes oxidation of mitochondrial antioxidative enzyme in BRAFV600E inhibitor-resistant melanoma cells. UACC-62-WT and UACC-62-R cells were preincubated with Mito-magnolol for 24 h and then treated with hydroethidine. Cell lysates were analyzed by HPLC and the superoxide-specific hydroxylation product (2-OH-E$^+$) and other two-electron and one-electron oxidation products (E$^+$ and E$^+$-E$^+$) were determined.

Figure 23A:
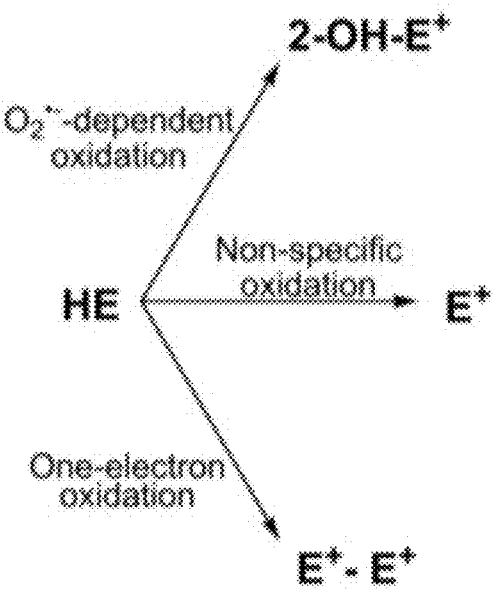
FIG. 23A-23B shows Mito-MGN effects on oxidant production in UACC-62-WT cells and UACC-62-R cells. (A) Scheme of ROS-dependent oxidation of hydroethidine (HE) probe. (B) Effect of Mito-MGN on different oxidation products of HE probe.
Figure 23B:
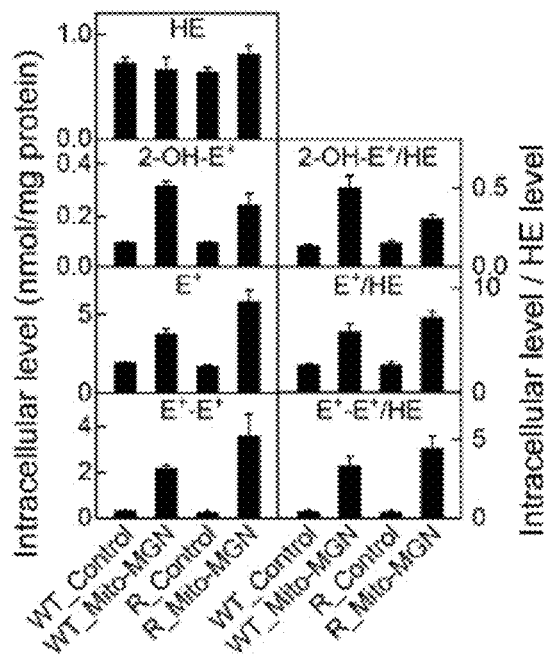

As shown in FIG. 23, Mito-magnolol induces significantly higher amount of 2-OH-E$^+$ and E$^+$ and E$^+$-E$^+$ in both WT and resistant cells. Hydroethidine (HE) was used to measure intracellular $O_2^{\cdot-}$ formation. 2-Hydroxyethidium (2-OH-E$^+$), the diagnostic marker product of $O_2^{\cdot-}$/HE reaction (FIG. 23A) increased in Mito-MGN treated melanoma cells (FIG. 23B). In addition, Mito-MGN induced the iron or peroxidase-dependent oxidation of HE as evidenced by enhanced intracellular formation of E$^+$-E$^+$ and E$^+$ (FIG. 23B).

Figure 24A:
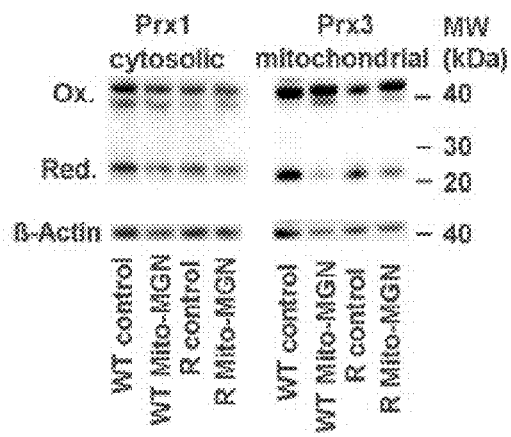
FIG. 24A-24C shows that Mito-MGN induces the oxidation of mitochondria- and peroxide-specific antioxidative enzyme (Prx3) in wild type (WT) and resistant (R) melanoma cells. (A) Western blot show the redox status of cytosolic (Prx1) and mitochondrial (Prx3) peroxiredoxins. (B) Quantitative analysis of the extent of Prx1 and Prx3 oxidation. Values are mean±SD, n=3. **, P≤0.01. (C) Scheme showing the pathways controlling the redox state and covalent dimer formation of peroxiredoxins in cells.
Figure 24B:
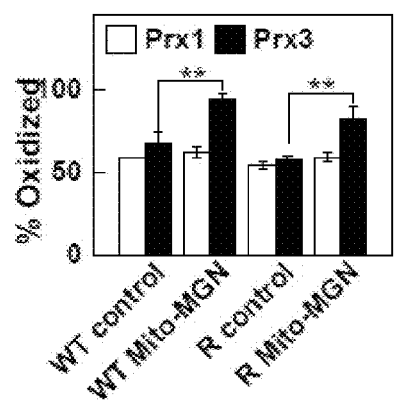
Figure 24C:
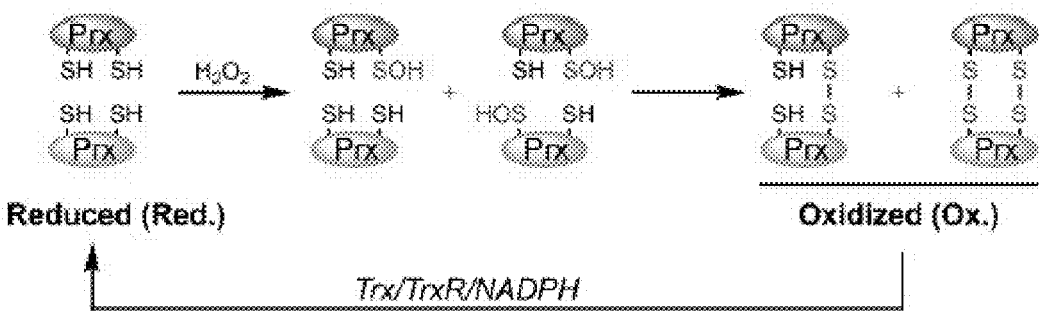

Peroxiredoxins (Prx) are abundant endogenous intracellular thiol peroxidases that act as compartment-specific sensors of hydrogen peroxide ($H_2O_2$) in mitochondrial (Prx3) and cytosolic (Prx1) compartments (62-64). Prxs rapidly react with $H_2O_2$ ($k=10^6$-$10^7$ M$^{-1}$ s$^{-1}$) (64, 65). Prx3 accounts for nearly 90% of mitochondrial peroxidase activity (64, 66). Experiments indicated that Mito-MGN stimulated the oxidation of mitochondrial Prx3, while cytosolic Prx1 was largely unaffected (FIGS. 24A and 24B) in both WT and resistant melanoma cells. FIG. 24C shows the scheme of oxidation of reduced thiol group in Prx3 to an oxidized form in the dimeric form.

Figure 25A:
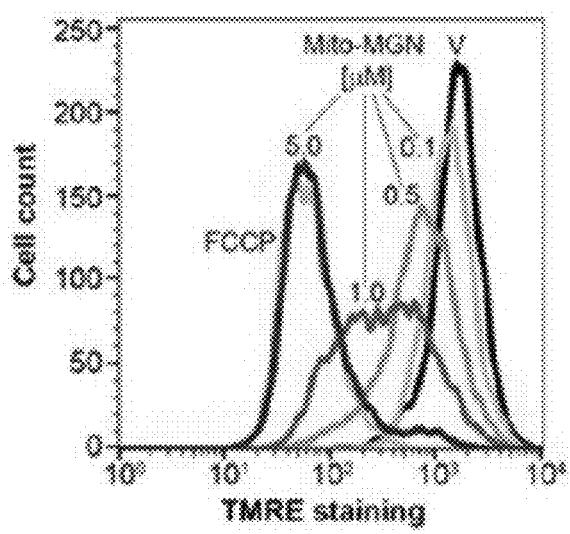
FIG. 25A-25B demonstrates mitochondrial depolarization in response to Mito-MGN. (A) Representative TMRE quantification using flow cytometry. (B) Mean fluorescence intensity (MFI) of TMRE in Mito-MGN-treated and vehicle (V)-treated UACC-62-WT cells. Values are mean±SEM, n=3
Figure 25B:
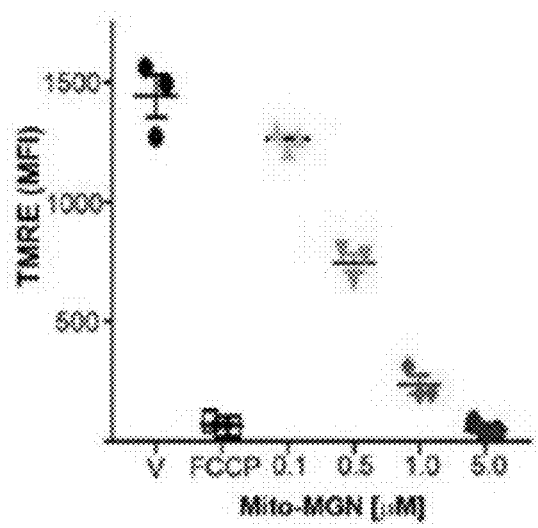

Not to be bound by any theory, but it is believed that Mito-MGN-induced ROS halts melanoma proliferation through induction of mitophagy. ROS at high μM concentrations have detrimental effects on lipids, proteins, and DNA, whereas at nM concentrations, ROS exerts potent signaling effects (11, 41, 65). We postulate that OXPHOS inhibition by Mito-MGN increases ROS levels, which in turn stimulates mitophagy. To test this hypothesis, we will use an iterative approach to first measure mitochondrial membrane damage, followed by the parallel examination of molecular markers and phagolysome activation needed for mitophagy. Tetramethylrhodamine ethyl ester (TMRE) is retained in metabolically active mitochondria and released into the cytosol and extracellular space of cells with depolarized/damaged mitochondria (67), as illustrated in our recent paper using related mitochondria-targeted agents (12). Pilot experiments indicate that Mito-MGN dose dependently decreases mitochondrial membrane potential in treated UACC-62 cells (FIGS. 25A and 25B).

Figure 26:
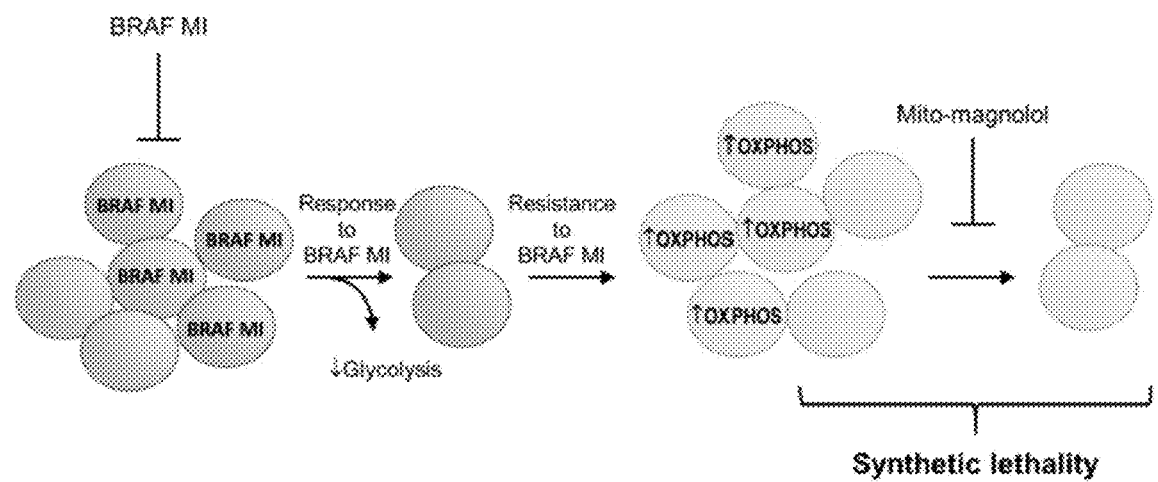
FIG. 26 is a schematic representation of Mito-magnolol inducing synthetic lethality to tumor cells resistant to kinase inhibitor (BRAF MI).
Figure 27A:
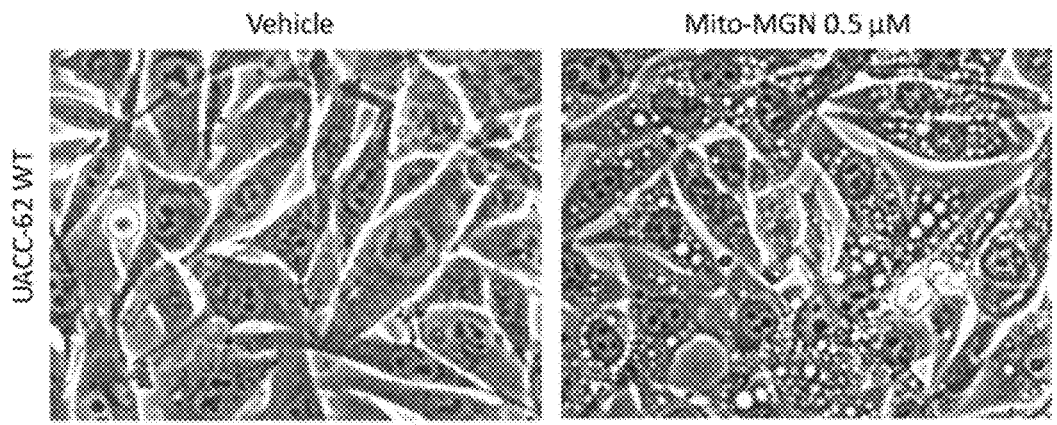
FIG. 27A-27C shows photomicrographs and Western blot analysis of melanoma cells UACC-62-WT in the absence and presence of Mito-MGN (A), and UACC-62-R cells in the absence and presence of Mito-MGN (B). Autophagic vacuoles are seen in Mito-MGN-treated both wild type and resistant melanoma cells. (C) Western blot of cell cycle- and autophagy-regulated proteins in Mito-MGN treated melanoma cells. UACC-62-WT and UACC-62-R cells were incubated for 24 h with 0.5 µM Mito-MGN. Data are representative of 3 separate biological replicates.
Figure 27B:
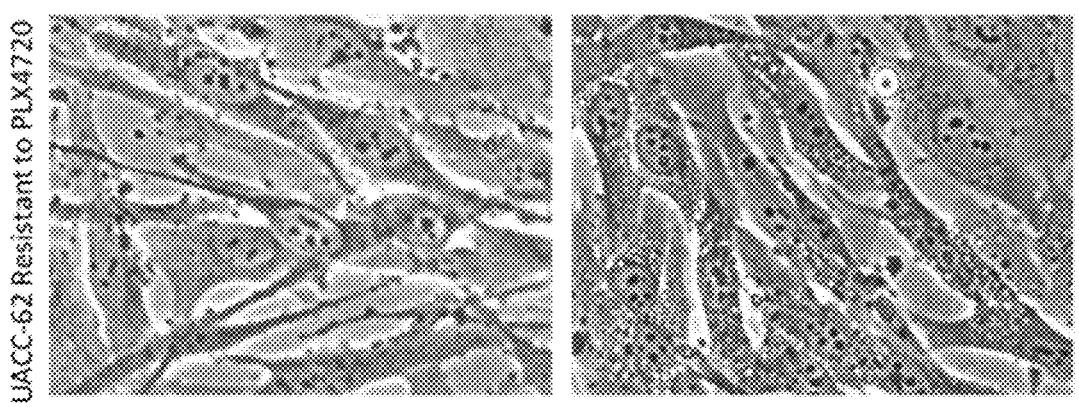
Figure 27C:
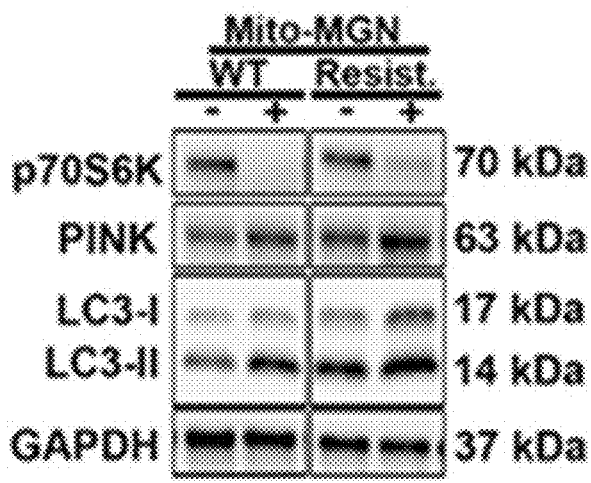

Based on the results, we postulate a novel mechanism by which Mito-magnolol inhibits the proliferation of BRAFV600E inhibitor-resistant melanoma cells (FIG. 26). This is a specific example of synthetic lethality induced by Mito-magnolol. Initial studies reveal that the mechanism of inhibition of cell proliferation in Mito-magnolol-treated melanoma wild type and drug resistant cells involve autophagy as evidenced by the accumulation of vacuoles (FIGS. 27A and 27B) and induction of autophagy regulated proteins, such as LC3-II (FIG. 27C).

Synergy Between Mito-Magnolol and PD-1 Blockade Therapy.

The interaction between programmed cell death (PD-1), a surface receptor expressed in activated T cells, and its ligand PD-L1 in antigen presenting cells (tumor cells) is responsible for evasion of tumor cells in humans. The idea that PD-1-PD-L1 blockade could improve the clinical outcome in patients potentially revolutionized personalized cancer therapy. Blocking PD-1 with PD-L1 monoclonal antibody (PD-L1 mAb) enhanced the tumor killing effects of T cells through increased recognition of tumor cells. PD-L1 mAb enhanced the mitochondrial oxidative metabolism and ROS in cytotoxic T cells (26).

Figure 28:
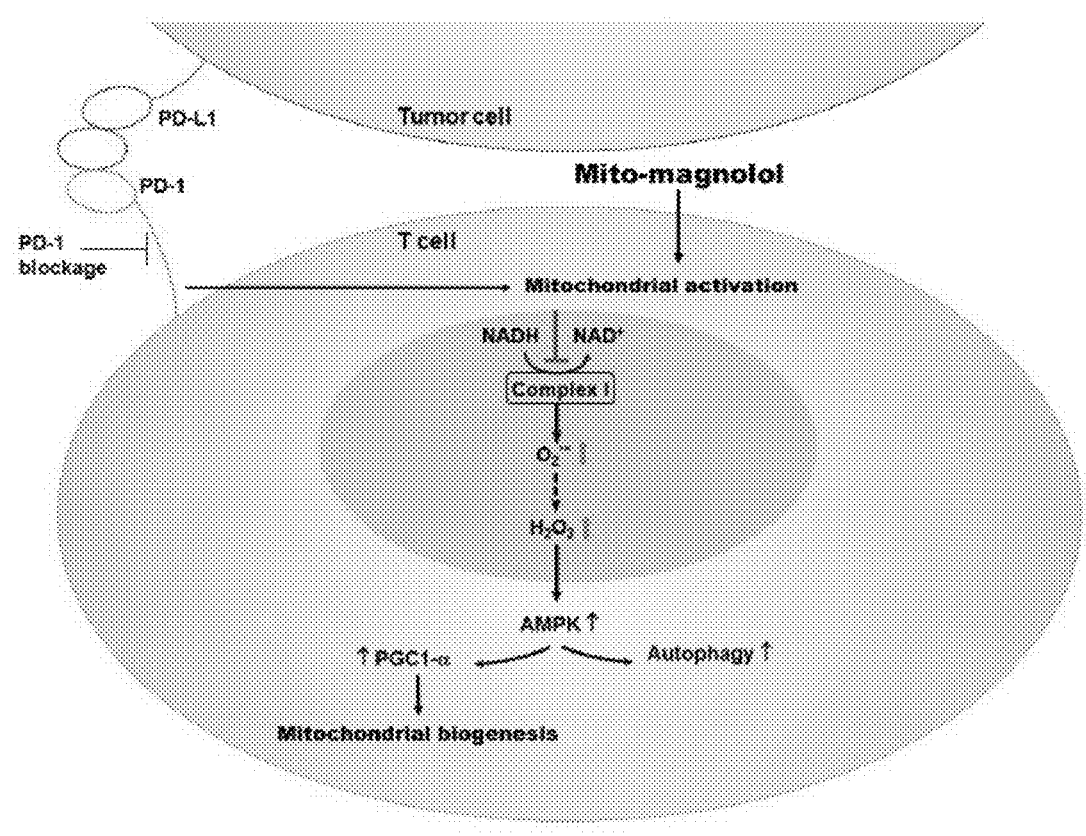
FIG. 28 shows a proposed mechanism of activation of mitochondrial biogenesis by Mito-magnolol in T cells: Enhanced tumor cell cytotoxicity.

Although PD-1 blockade immunotherapy has revolutionized treatment of some cancers (melanoma, lung cancer), many patients did not respond favorably to immunotherapy. The lack of response was attributed to an overall exhaustion of T cells (in the immunosuppressive tumor microenvironment) caused by mitochondrial dysfunction and decreased energy metabolism. During PD-1 blockade therapy, it was shown that tumor reactive CD8+ T cells exhibited higher mitochondrial membrane potential and ROS. It was suggested that mitochondrial stimulation in T cells likely supports the antitumor activity (26). It was rationalized that unresponsive T cells may be activated using combinatorial therapies involving PD-1 blockade therapy and mitochondrial ROS stimulators. Our surprising discovery—Mito-magnolol-mediated chemotherapy in drug resistant melanoma—in combination with PD-1 blockade therapy, can help overcome the unresponsiveness of immunotherapy by stimulating its mitochondrial ROS and the key energy sensors, e.g., AMP-activated protein kinase (AMPK). A hypothetical scheme combining PD-1 blockade and mitochondrial OXPHOS and ROS stimulators (Mito-magnolol) in activating and stimulating mitochondrial biogenesis in T cells (FIG. 28), thereby enhancing their tumor cell cytotoxicity.

References Example 1

1. Kim H K, Noh Y H, Nilius B, Ko K S, Rhee B D, Kim N, Han J. Current and upcoming mitochondrial targets for cancer therapy. Semin Cancer Biol. 2017 December; 47:154-67.
2. Gottesman MM1, Fojo T, Bates S E. Multidrug resistance in cancer: role of ATP-dependent transporters. Nat Rev Cancer. 2002 January; 2(1):48-58.
3. Haq R, Fisher D E, Widlund H R. Molecular pathways: BRAF induces bioenergetic adaptation by attenuating oxidative phosphorylation. Clin Cancer Res. 2014 May 1; 20(9):2257-63.
4. Berridge M V, Tan A S. Effects of mitochondrial gene deletion on tumorigenicity of metastatic melanoma: reassessing the Warburg effect. Rejuvenation Res. 2010 April-June; 13(2-3):139-41.
5. Pollak M. Targeting oxidative phosphorylation: why, when, and how. Cancer Cell. 2013 Mar. 18; 23(3):263-4.
6. Vazquez F, Lim J H, Chim H, Bhalla K, Girnun G, Pierce K, Clish C B, Granter S R, Widlund H R, Spiegelman B M, Puigserver P. PGC1α expression defines a subset of human melanoma tumors with increased mitochondrial capacity and resistance to oxidative stress. Cancer Cell. 2013 Mar. 18; 23(3):287-301.

7. Haq R, Shoag J, Andreu-Perez P, Yokoyama S, Edelman H, Rowe G C, Frederick D T, Hurley A D, Nellore A, Kung A L, Wargo J A, Song J S, Fisher D E, Arany Z, Widlund H R. Oncogenic BRAF regulates oxidative metabolism via PGC1α and MITF. Cancer Cell. 2013 Mar. 18; 23(3):302-15.

8. Fanciulli M, Bruno T, Giovannelli A, Gentile F P, Di Padova M, Rubiu O, Floridi A. Energy Metabolism of Human LoVo Colon Carcinoma Cells: Correlation to Drug Resistance and Influence of Lonidamine. Clin Cancer Res. 2000 April; 6(4):1590-7.

9. Vellinga T T, Borovski T, de Boer V C, Fatrai S, van Schelven S, Trumpi K, Verheem A, Snoeren N, Emmink B L, Koster J, Rinkes I H, Kranenburg O. SIRT1/PGC1α-Dependent Increase in Oxidative Phosphorylation Supports Chemotherapy Resistance of Colon Cancer. Clin Cancer Res. 2015 Jun. 15; 21(12):2870-9.

10. Tan Z, Luo X, Xiao L, Tang M, Bode A M, Dong Z, Cao Y. The Role of PGC1α in Cancer Metabolism and its Therapeutic Implications. Mol Cancer Ther. 2016 May; 15(5):774-82.

11. Ippolito L, Marini A, Cavallini L, Morandi A, Pietrovito L, Pintus G, Giannoni E, Schrader T, Puhr M, Chiarugi P, Taddei M L. Metabolic shift toward oxidative phosphorylation in docetaxel resistant prostate cancer cells. Oncotarget. 2016 Sep. 20; 7(38):61890-904.

12. Petrylak D P, Tangen C M, Hussain M H, Lara P N Jr, Jones J A, Taplin M E, Burch P A, Berry D, Moinpour C, Kohli M, Benson M C, Small E J, Raghavan D, Crawford E D. Docetaxel and estramustine compared with mitoxantrone and prednisone for advanced refractory prostate cancer. N Engl J Med. 2004 Oct. 7; 351(15):1513-20.

13. Gottschalk S, Anderson N, Hainz C, Eckhardt S G, Serkova N J. Imatinib (STI571)-mediated changes in glucose metabolism in human leukemia BCR-ABL-positive cells. Clin Cancer Res. 2004 Oct. 1; 10(19):6661-8.

14. Cheng G, Zielonka J, Dranka B P, McAllister D, Mackinnon A C Jr, Joseph J, Kalyanaraman B. Mitochondria-targeted drugs synergize with 2-deoxyglucose to trigger breast cancer cell death. Cancer Res. 2012 May 15; 72(10):2634-44.

15. Cheng G, Zielonka J, McAllister D, Tsai S, Dwinell M B, Kalyanaraman B. Profiling and targeting of cellular bioenergetics: inhibition of pancreatic cancer cell proliferation. Br J Cancer. 2014 Jul. 8; 111(1):85-93.

16. Weinberg F, Hamanaka R, Wheaton W W, Weinberg S, Joseph J, Lopez M, Kalyanaraman B, Mutlu G M, Budinger G R, Chandel N S. Mitochondrial metabolism and ROS generation are essential for Kras-mediated tumorigenicity. Proc Natl Acad Sci USA. 2010 May 11; 107(19):8788-93.

17. Cheng G, Zielonka J, McAllister D M, Mackinnon A C Jr, Joseph J, Dwinell M B, Kalyanaraman B. Mitochondria-targeted vitamin E analogs inhibit breast cancer cell energy metabolism and promote cell death. BMC Cancer. 2013 Jun. 13; 13:285.

18. Asin-Cayuela J, Manas A R, James A M, Smith R A, Murphy M P. Fine-tuning the hydrophobicity of a mitochondria-targeted antioxidant. FEBS Lett. 2004 Jul. 30; 571(1-3):9-16.

19. Zielonka J, Joseph J, Sikora A, Hardy M, Ouari O, Vasquez-Vivar J, Cheng G, Lopez M, Kalyanaraman B. Mitochondria-Targeted Triphenylphosphonium-Based Compounds: Syntheses, Mechanisms of Action, and Therapeutic and Diagnostic Applications. Chem Rev. 2017 Aug. 9; 117(15):10043-120.

20. Brunen D, Bernards R. Drug therapy: Exploiting synthetic lethality to improve cancer therapy. Nat Rev Clin Oncol. 2017 June; 14(6):331-2.

21. Kaelin W G Jr. The concept of synthetic lethality in the context of anticancer therapy. Nat Rev Cancer. 2005 September; 5(9):689-98.

22. Corazao-Rozas P, Guerreschi P, Jendoubi M, Andrê F, Jonneaux A, Scalbert C, Garcon G, Malet-Martino M, Balayssac S, Rocchi S, Savina A, Formstecher P, Mortier L, Kluza J, Marchetti P. Mitochondrial oxidative stress is the Achille's heel of melanoma cells resistant to Braf-mutant inhibitor. Oncotarget. 2013 November; 4(11): 1986-98.

23. Chuang D Y, Chan M H, Zong Y, Sheng W, He Y, Jiang J H, Simonyi A, Gu Z, Fritsche K L, Cui J, Lee J C, Folk W R, Lubahn D B, Sun A Y, Sun G Y. *Magnolia* polyphenols attenuate oxidative and inflammatory responses in neurons and microglial cells. J Neuroinflammation. 2013 Jan. 29; 10:15. doi: 10.1186/1742-2094-10-15.

24. Tian Y, Feng H, Han L, Wu L, Lv H, Shen B, L1 Z, Zhang Q, Liu G. Magnolol Alleviates Inflammatory Responses and Lipid Accumulation by AMP-Activated Protein Kinase-Dependent Peroxisome Proliferator-Activated Receptor a Activation. Front Immunol. 2018 Feb. 5; 9:147. doi: 10.3389/fimmu.2018.00147. eCollection 2018.

25. Murphy M P, Smith R A. Targeting antioxidants to mitochondria by conjugation to lipophilic cations. Annu Rev Pharmacol Toxicol. 2007; 47:629-56.

26. Chamoto K, Chowdhury P S, Kumar A, Sonomura K, Matsuda F, Fagarasan S, Honjo T. Mitochondrial activation chemicals synergize with surface receptor PD-1 blockade for T cell-dependent antitumor activity. Proc Natl Acad Sci USA. 2017 Jan. 31; 114(5):E761-E70.

Figure 31:
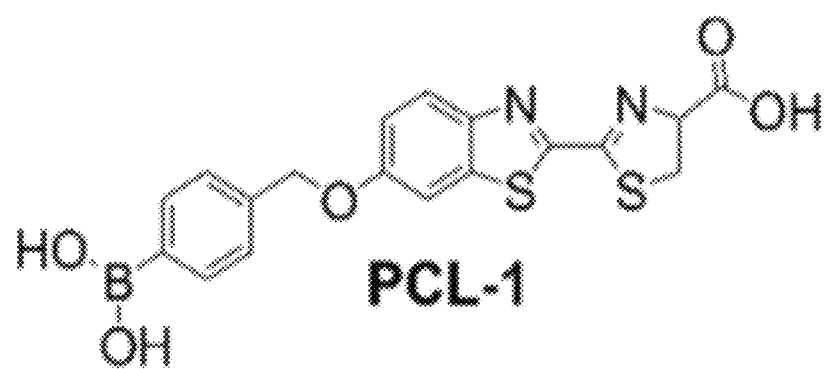
FIG. 31 shows the chemical structure of PCL-1 molecular probe for oxidant detection in vivo.

Example 2: In Vivo Efficacy and Molecular Mitochondrial Mechanism of Mito-MGN Effects on Melanoma Progression Not to be bound by any theory, but from the cell culture results, Mito-MGN seem to inhibit tumor bioenergetics, stimulate mitochondrial ROS and redox signaling, and mitigate tumorigenesis in human UACC-62 and B16 melanoma models. To investigate these effects in vivo on tumor growth, ROS formation, and mitophagy, we are using state-of-the-art analytical approaches, including micro-computed tomography (μCT), bioluminescence imaging (BLI) of a peroxy-caged luciferin (PCL-1, FIG. 31) and a probe-free ex vivo cryogenic EPR technique (75, 76). Although new and improved fluorescent probes can detect specific ROS in cell culture systems, extrapolation of these assays to cancer xenografts has proven difficult (31, 50). Thus, our use of an ex vivo, low temperature, probe-free, EPR technique is vital for assessing oxidant formation and redox changes and metabolic reprogramming in tumor mitochondria.

Figure 32A:
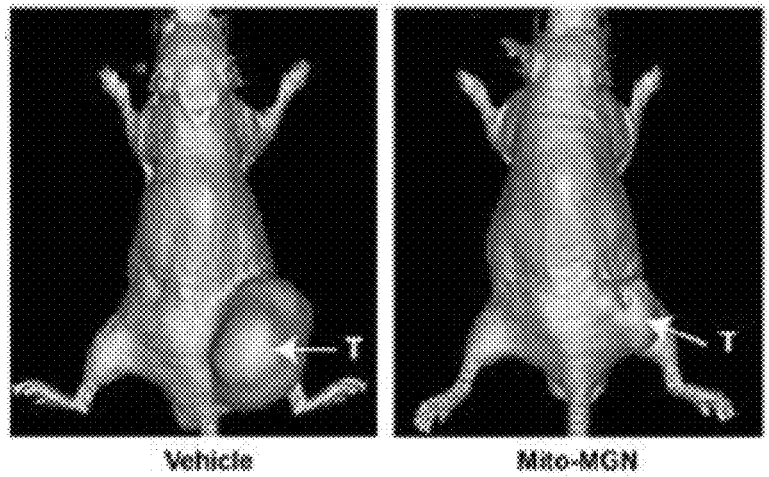
FIG. 32 shows computed tomography (CT) imaging of melanoma in control and Mito-MGN treated mice. (A) Representative μCT images on day 58 from UACC-62-WT xenographed (T=tumor) mice treated twice a week with vehicle (left) or 1 mg Mito-MGN (right). Data representative of 2 mice per group. (B) Quantification of tumor volume (mm$^3$) measured using calipers ex vivo on day 58.
Figure 32B:
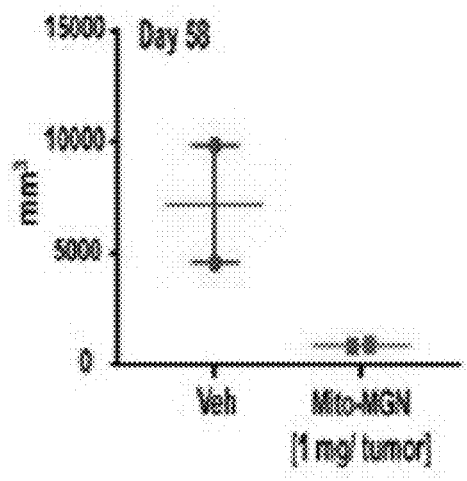

The efficacy of Mito-MGN in a murine model of melanoma was tested using cells sensitive and resistant to BRAF inhibitors as tools to probe the anti-tumor effects of targeted OXPHOS inhibitors. Treatment of mice orthotopically engrafted with UACC-62-WT cells with 1 mg Mito-MGN, injected intratumorally in 50 μL, potently reduced tumor size as measured in vivo using μCT imaging (FIG. 32A) and ex vivo from excised tumors (FIG. 32B).

Figure 33:
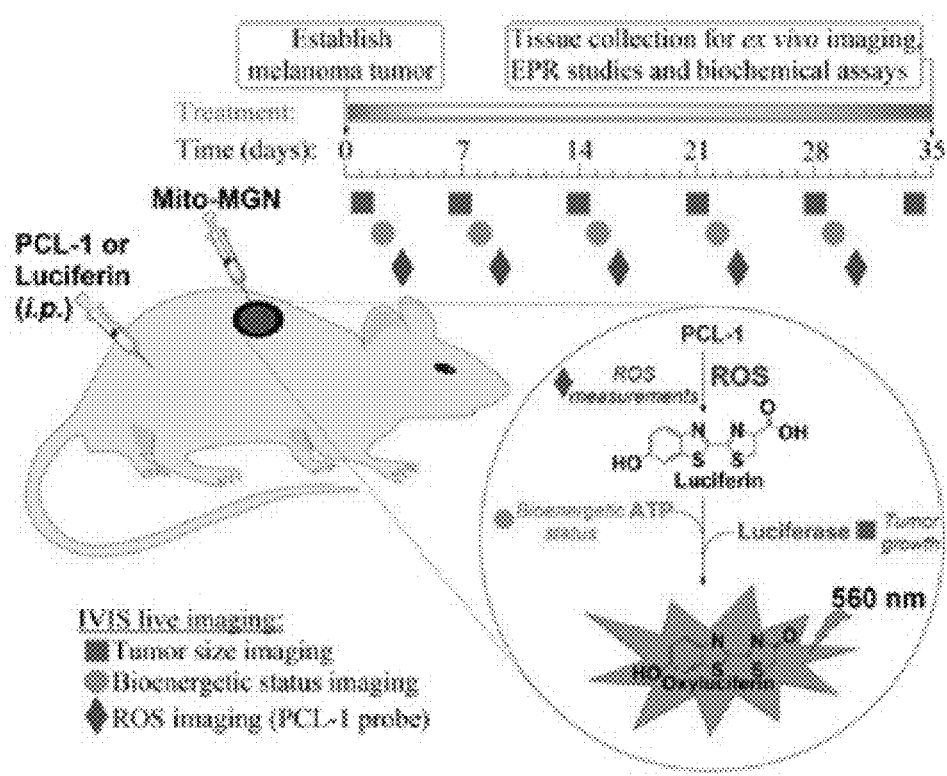
FIG. 33 depicts the protocol for in vivo bioluminescence imaging of tumor growth, bioenergetic status, and ROS in murine melanoma models.
Figure 34:
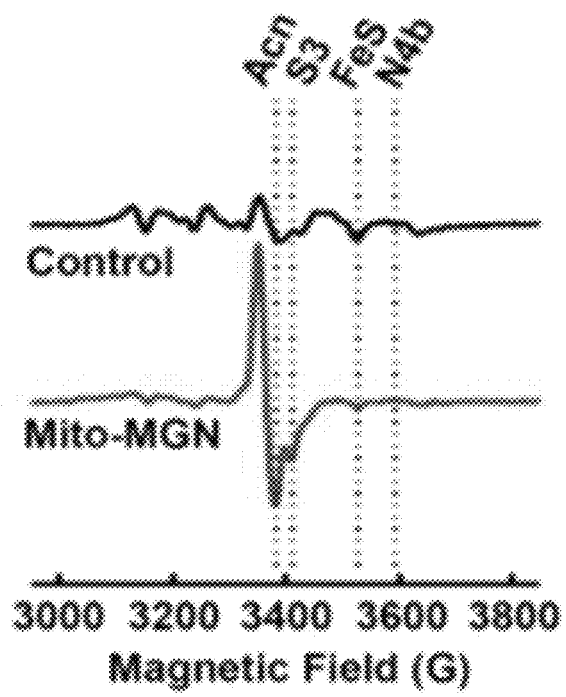
FIG. 34 demonstrates ex vivo EPR detection of oxidants in cancer. UACC-62-WT melanoma cells were examined by low-temperature EPR to monitor oxidants formed in control and Mito-MGN-treated cells. Increased levels of oxidized aconitase (Acn) provides a biomarker for in vivo Mito-MGN effect on melanoma. S3=cluster from complex I and II; FeS=reduced iron sulfur; N4b=4Fe-4S.

Example 3: Dose Limiting Effects of Mito-MGN in BRAF Inhibitor Resistant UACC-62-R Cells as Well as B16 BRAF WT Melanoma Cells The objective of this experiment is to use human melanoma xenograft and metastatic B16.F10 syngeneic orthograft models to investigate functional effects of Mito-MGN on tumor growth and metastasis in vivo. UACC or B16 tumor-bearing mice will be treated via intra-tumoral injection with 0.1, 0.5, 1, and 5 mg Mito-MGN. Immunohistochemistry will be used to investigate tumor mitophagy, proliferation, and cell death. BLI will be performed as illustrated in FIG. 34 and described in our prior publications (6, 10, 60, 77-79). BLI is based on the ATP-dependent, luciferase-catalyzed oxidation of luciferin accompanied by light emission proportional to the number of cancer cells (FIG. 33, Tumor size imaging). To monitor tumor size and ROS formation in vivo, UACC-62 and B16 melanoma cells will be engineered to express firefly luciferase. Because luc-catalyzed oxidation of luciferin requires ATP as a cofactor, this reaction can also be used to monitor changes in ATP level, when the tumor size is not a variable. Mice will be imaged first for tumor size and again the next day for ATP, a few hours after administering Mito-MGN (FIG. 33, Bioenergetic status imaging). To detect $H_2O_2$, HOCl, and $ONOO^-$ ROS, we will use PCL-1, a small-molecule cell-permeable probe that upon oxidation, yields luciferin in situ that is further oxidized in luciferase-transfected tumor cells to produce luminescence (FIG. 33, ROS imaging). Luciferin and PCL-1 are cleared within hours, so they can be used sequentially after 24 h (75).

Side-by-side experiments contrasting Mito-MGN effects on WT and BRAF resistant human xenograft and murine B16.F0, B16.F1, and B16.F10 melanoma progression will be completed. Mice will be randomly assigned to either Mito-MGN or vehicle treatment groups immediately after tumor cell inoculation. Tumor size will be measured weekly using BLI as we have shown previously (10, 60, 77-80), or using μCT as shown in FIG. 32. Imaging and histopathology will be completed by laboratory personnel blinded to the treatment conditions. Each group will comprise 4-6 mice and be repeated in 2-3 replicate studies to ensure sufficient statistical power. For example, a cumulative group size of 12 mice will provide 80% power to detect a difference of 1.27 radiance luminescence units (6.57 to 5.30), as calculated from our pilot studies and analyzed with a one-way ANOVA and a Tukey's multi-comparison test (a set at 0.05). Melanoma has a slightly higher incidence in men relative to women (1, 2), so our preclinical studies will include equal numbers of male and female mice.

Example 4: In Vivo Tumor Progression in Mito-MGN Treated Melanoma and Stimulation of ROS In Vivo Human UACC-62 xenografted SCID mice or B16 cells engrafted to C57BL/6 mice will be treated 3 times per week with 0.1, 0.5, 1, and 5 mg intratumoral doses of Mito-MGN. These doses were rationally selected based on the in vitro data and our prior reports using other mitochondria-targeted agents (8, 10, 17). Mice treated with vehicle will be the control. BLI and μCT and will be used for in vivo measurement of tumor growth and metastasis. At the completion of the experiment, mice will be sacrificed, and the primary tumor as well as the metastatic target organs (liver, lung, and brain) removed to measure overall tumor burden. Metastasis will be quantified by luminescence detection and wet weight of those organs. The incidence of metastasized tumors in control compared to treated mice will be recorded as a ratio of luminescent tumors in each organ and stated as overall tumor burden.

To quantify mitophagy in vivo, mice will be engrafted with mKeima transduced UACC-62 or B16 cells and treated with Mito-MGN. Tumors will be excised and phagosome acidification, as a measure of in vivo mitophagy, will be quantified using immunofluorescence microscopy (71). A portion of the excised tumor will be fixed in zinc formalin for histological analyses. Immunohistochemistry will be performed using anti-Ki67, anti-cleaved caspase-3, or anti-Parkin to visualize and quantify tumor cell growth, death, and mitophagy, respectively.

Ex Vivo EPR Analysis of Mitochondrial Complexes in Mouse Melanoma.

To determine if Mito-MGN treatment stimulates ROS in vivo, low-temperature EPR spectroscopy will be employed. Mitochondria exhibit multiple EPR signals, depending on the local redox environments of the individual mitochondrial complexes. EPR spectra (recorded at liquid helium temperatures) of mitochondria can be modeled as the sum of a set of simulated basis spectra from the redox centers of mitochondrial complexes I-IV and aconitase (49). FIG. 34 illustrates pilot EPR data of melanoma cells. The relative signal peaks indicate expression levels, the local and global redox states, and the integrity of the electron transport chain in control (black line) and Mito-MGN treated (red line) melanoma cells.

Melanoma tumors will be obtained from UACC xenograft or B16 engrafted mice after control and Mito-MGN treatment using an optimized sample harvesting procedure as described in our recent publication (49). Briefly, tumor tissues are flash frozen in liquid nitrogen, minced, and transferred to EPR tubes for measurements at liquid helium temperatures. A strong signal at g=1.94 indicates a reduced form of a $[2Fe-2S]^+$ center of mitochondrial complex I reflecting blocked electron transfer. The level of oxidatively inactivated mitochondrial aconitase is an established marker of mitochondrial oxidative stress (49). Aconitase is inactivated by superoxide-induced oxidation of the $[4Fe-4S]^{2+}$ cluster. The $[4Fe-4S]^{2+}$ cluster of active aconitase is EPR silent, whereas superoxide-damaged aconitase has a $[3Fe-4S]^+$ cluster with characteristic EPR signals in the g=2.03 and 2.01 regions (49). Thus, increased ROS-mediated oxidative stress is indicated by increased aconitase (Acn) signal in the melanoma cells in vitro and tissue ex vivo.

Pilot studies indicate that three weekly treatment with Mito-Mag at 5 mg/kg resulted in little liver or kidney toxicity (Table 1).

TABLE 1

| | Toxicity | | |
|---|---|---|---|
| | ALT[IU/L] ref (22-77) | AP[IU/L] ref (45-222) | BUN[mg/dL] ref (12-28) |
| Control | 60.4 ± 22.2 | 52.2 ± 4.9 | 24.4 ± 1.6 |
| Mito-MGN | 58.7 ± 12.7 | 36.7 ± 10.8 | 24.5 ± 1.9 |

Serum levels assayed on day 19. ALT: alanine transaminase; AP: alkaline phosphatase; BUN: Blood urea nitrogen. Mean ± SE, n = 4-5

Example 5: Mito-MGN in Combination with BRAF Kinase Inhibitor Therapy

Multi-modal treatment approaches, including those targeting metabolism are an increasingly powerful strategy to treat cancer (28, 29). We will therefore examine the potential for Mito-MGN to provide additive or synergistic benefit to standard-of-care BRAF inhibitor chemotherapy. We hypothesize that the OXPHOS inhibitor Mito-MGN can synergize with the traditional BRAF inhibitor, vemurafenib, to abrogate melanoma progression in vivo. Tumor size and metastasis will be measured at study end (day 35). BRAF inhibitor sensitive B16 or UACC-62-WT melanoma engrafted mice will first be treated 3× weekly starting on day 2 with Mito-MGN, at an initial 1 mg per tumor dose, followed by a weekly injection with BRAF inhibitor (500 nM) starting on day 3. Subsequent experiments will test a range of Mito-MGN doses from 0.1, 0.5 and 5 mg. Next, we will reverse the sequence of drug administration in which melanoma engrafted mice will first receive weekly vemurafenib starting on day 2 with Mito-MGN 3× per week starting on day 3.

We expect that Mito-MGN will abrogate the growth and progression of both BRAF inhibitor resistant and sensitive melanoma in vivo and block growth and metastasis across a range of non-metastatic (F0, F1) and metastatic (F10) B16 melanoma. Dual targeting of glycolysis using BRAF inhibitors plus Mito-MGN to inhibit OXPHOS is expected to strongly inhibit melanoma progression in vivo. The in vivo toxicity of Mito-MGN will be monitored using histopathologic assessment by a board-certified pathologist and serum quantification of hepatic, kidney, and cardiac biomarkers using veterinary assays. As proof of biological safety, an analogous compound, mito-honokiol, is well-tolerated, with no overt toxicity when administered at doses 20-times higher than those used for Mito-MGN (61). Prior reports effectively used catalase or superoxide dismutase over-expressing cells to scavenge cellular ROS/RNS (81). Changes in tumor cell metabolism may elicit alterations in accessory cells within the tumor microenvironment. Endothelial, fibroblast, and neuronal changes will be investigated using immunohistochemistry. While we expect the PCL-1 experiments to document changes in ROS within the tumor microenvironment, if we observe changes in those cells we would use a multiplex system to interrogate the secretome of Mito-MGN treated tumors. LCMS will be used to profile extracellular metabolites such as lactate or alanine. We will detect the major and minor products derived from Mito-B reaction with ROS/RNS.

Example 6: Analyze the Impact of Mito-MGN on Anti-Melanoma Immunity and Energy Metabolism of Tumor Reactive T Cells Melanoma is a variably immunogenic tumor with sensitivity to immune-targeted therapies (53, 82, 83). Melanoma lymphocyte infiltrate is highly associated with improved survival (84). Despite the prevalence of immune cells, anti-tumor immunity may be prevented by upregulation of checkpoint inhibitor ligands on tumor cells (85) that suppress anti-tumor effector CD8+ cytotoxic T lymphocytes (CTL) (85, 86). Paradoxically, while there are unproductive immune responses in the tumor microenvironment, there is an accumulation of tumor-reactive helper T cells and CTLs. As illustrated by Chen and Mellman (52), immune responses to cancer require effective infiltration of tumor reactive cells into the tumor and activated T cell-mediated killing of tumor cells. We propose that selectively targeting tumor mitochondria with Mito-MGN will promote anti-melanoma immune responses. Not to be bound by any theory, but we believe that Mito-MGN will promote anti-tumor immunity by inhibiting tumor cell OXPHOS and increasing ROS and mitophagy, which will in turn activate tumor killing independent of checkpoint protein expression.

Figure 35A:
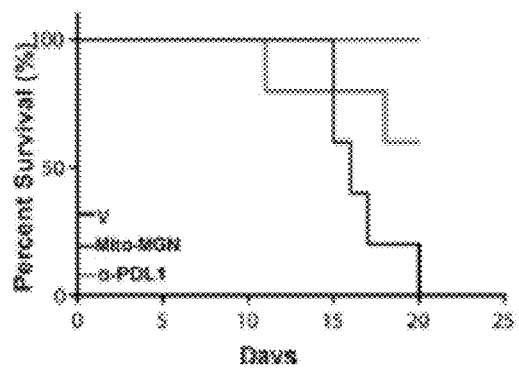
FIG. 35A-35C demonstrates that Mito-MGN increases survival and decreases tumor size in B16-F10 melanoma. (A) Kaplan-Maier survival curves of B16-F10 engrafted mice treated on days 7, 9, 11, 14, 16, & 18 with Mito-MGN [1 mg] or with α-PD-L1 [250 μg]. (B) Tumor size (mm2) over time. (C) Tumor volume measured on day 19. Values are mean±SD, n=4 mice/group. ***, P≤0.001.
Figure 35B:
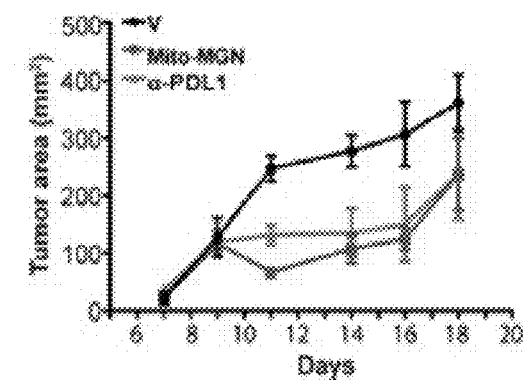
Figure 35C:
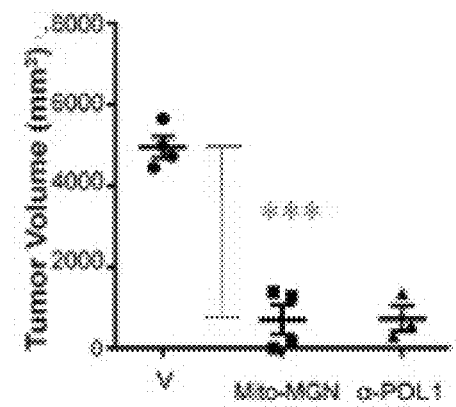
Figure 36:
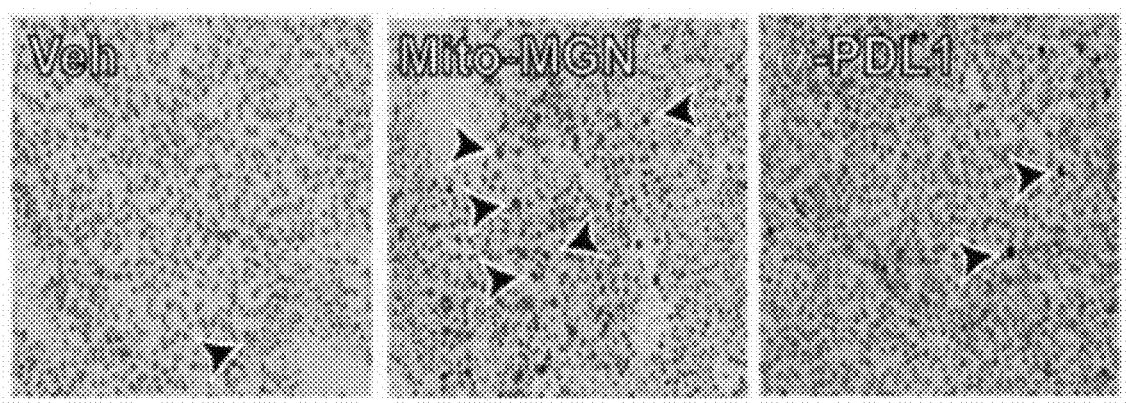
FIG. 36 demonstrates tumor infiltrating CD3+ T cells from vehicle (Veh), Mito-MGN, and anti-PD-L1 treated murine B16-F10 melanoma. T cells were detected using CD3 immunostaining (brown). Arrowheads highlight CD3+ T cells in melanoma (blue cells). Data representative of 4 separate mice.

In a pilot experiment, mice orthotopically engrafted with B16.F10 cells and treated with 1 mg/tumor Mito-MGN or 250 µg neutralizing anti-PD-L1 antibody showed increased survival (FIG. 35A) and decreased melanoma growth in vivo (FIG. 35). Mito-MGN efficiency was equal to anti-PD-L1 in abrogating tumor progression and size (FIG. 35B-C). Immunostaining of excised tumors with antibody against CD3, a pan-T cell marker, indicated that Mito-MGN and anti-PD-L1 each increased T cell levels compared to vehicle control tumors (FIG. 36), supporting our hypothesis that Mito-MGN is an immune stimulant that potently inhibits melanoma progression. Our data suggest the exciting potential for Mito-MGN to either synergize with checkpoint inhibitors such as PD-L1 or to improve immunotherapy independent of tumor checkpoint protein expression.

The B16 orthotopic syngeneic melanoma model will be used to investigate functional effects of Mito-MGN on immune cell proliferation and activation in melanoma. Flow cytometry will be used to comprehensively quantify lymphoid and myeloid cell populations within tumors of Mito-MGN treated and control mice. Immunohistochemistry will be used to visualize localization of intra-tumoral T cells and myeloid cells. To measure functional effects of Mito-MGN, apoptosis of melanoma cells cultured with tumor-reactive T cells will be measured using high-throughput IncuCyte cytotoxicity assays. Bioenergetic metabolism of immune cells will be measured using the Seahorse Extracellular Analyzer. Tumor cell levels of checkpoint inhibitor proteins will be measured by flow cytometry.

Effect of Mito-MGN on T Cell Activation and Melanoma Cell Killing.

To test the hypothesis that Mito-MGN enhances immune proliferation, we will first profile and quantify the lymphoid and myeloid cell subsets within melanomas of mice treated with 0.1, 0.5, 1, and 5 mg Mito-MGN or vehicle control. Mice treated with magnolol will serve as a separate control. Mice will be euthanized on days 7, 12, or 19 and bone marrow, spleen, and the tumor excised and immune cells dissociated. One half of the tumor will be fixed for immunohistochemical analysis and morphometric enumeration of immune cell localization. Immune cell subsets will be comprehensively profiled using a battery of lymphoid and myeloid markers from the remaining half of the tumor tissue (Table 1). Leukocyte proliferative capacity will be assessed by staining CD45+ cells for Ki67. Levels of tumor cell expressed PD-L1 will be measured from dissociated CD45− cells.

TABLE 1

Flow Cytometry

| Cell subset | Associated markers |
|---|---|
| Pan-leukocyte marker | CD45 |
| Activated CTL | CD3+, CD8+ CD69+ CD44+ granzyme B+ |
| Helper T cell | CD3+ CD4+ |
| Treg | CD3+ CD4+ *foxp3*+ |
| TAM | CD11b+ Ly6G+ Ly6C$^{low}$ |
| Granulocytic MDSC | CD11b+ Ly6G− Ly6C$^{high}$ |
| NK cell | CD3− NK1.1+ |

CTL, cytotoxic T lymphocytes, Treg, regulatory T cell, TAM, Tumor-associated macrophage; MDSC, myeloid-derived suppressor cell; NK, Natural Killer; Italicized markers: intracellular Flow cytometry of isolated CD45+ immune cells will be used to test if Mito-MGN enhances T cell activation. T cell activation will be quantified by enumeration of Granzyme B, IFNγ, and PD-1 staining. To test the hypothesis that Mito-MGN increases tumor cell killing by infiltrating T cells, that portion of the tumor not used for flow cytometry will be digested to isolate and expand T infiltrating lymphocytes (TIL) ex vivo. TILs will be incubated 10:1 with anti-CD3/28 antibody-loaded and irradiated K562 artificial antigen presenting cells engineered to express CD32 and CD137L. TIL-K562 cells will be co-cultured in full growth medium supplemented with the proliferative cytokines IL2, IL7, and IL15. After 7-10 days in culture expanded TILs will be incubated at 5:1, 10:1, or 20:1 with 1×105 B16 cells and tumor cell killing measured using an IncuCyte caspase-3/7 assay. IFNγ ELISPOT will be measured as a second readout for activated T cell killing. T cells from non-tumor bearing mice will be a control.

Mito-MGN-Induced ROS Effects on T Cell Activation and Melanoma Cell Killing.

Our prediction is that mitochondrial ROS drives activation of tumor-reactive $CD8^+$ CTLs. To test this, we will assay both T cell proliferation and activation using the IncuCyte in vitro imaging system. Naïve $CD8^+$ T cells will be isolated from the spleens of non-tumor bearing mice. TILs will be dissociated from melanoma-bearing mice. T cells will be expanded 7-10 days (see above) and incubated separated from B16 cells in a transwell (0.4 µm pore size). B16 cells will be treated with anti-proliferative doses of Mito-MGN or remain untreated as a control. Mitochondrial ROS (e.g., $H_2O_2$) will be quenched by pre-treating melanoma with catalase, PEG-catalase, or SOD mimetics prior to the addition of TILs to the transwell insert (102). T cell proliferation in the melanoma co-culture will be enumerated every 6 h by measuring T cell confluence using the IncuCyte imager.

Effector T cells use aerobic glycolysis while memory T cells rely on OXPHOS (88, 103). Activators of AMPK and inhibitors of mTORC1 signaling stimulate effector T cells (104). The dynamic bioenergetic metabolism of T cells may impact mitochondrial membrane potential (105). Thus, it is possible that Mito-MGN activates CTLs by inhibiting OXPHOS metabolic reprogramming. As we have done for normal and cancer epithelial cells, we will ascertain the potential for Mito-MGN to directly affect T cells, using LCMS will quantify Mito-MGN localization, or in separate experiments, ATP levels, within naïve $CD8^+$ T cells and TILs from melanoma tumors. Separate B16 cell cultures will be treated and assayed in parallel to directly compare Mito-MGN selectivity for these cells. Seahorse bioenergetic profiles will measure SCAR and OCR, while TMRE flow cytometry will be used to measure mitochondrial metabolism and membrane potential in Mito-MGN-treated naïve T cells and effector TILs. Lastly, we will expand melanoma TILs ex vivo with CD3 and CD28 antibodies in the presence or absence of titrated levels of Mito-MGN. Proliferation of T cells will be enumerated every 2 h using IncuCyte and confirmed using Ki67 flow cytometry. To examine the potential for Mito-MGN to increase anti-tumor functional effects, TILs will be expanded ex vivo and after 7 days co-incubated with B16 cells to measure tumor cytotoxicity using the caspase 3/7 assay as illustrated above.

Mito-MGN Effects in Combination with Checkpoint Blockade.

While we hypothesize that Mito-MGN stimulates T cell proliferation into the tumor mass, it remains possible that cellular mechanisms within the tumor parenchyma functionally prevent tumor cell killing by CTLs, an in vivo caveat our in vitro killing assays may not detect. The interaction between programmed death (PD-1), a surface receptor expressed on activated T cells, and its ligand, PD-L1 on tumor cells, is responsible for evasion of immune surveillant cytotoxic T cells (106). Although PD-1 blockade has revolutionized treatment in melanoma, T cell exhaustion caused by mitochondrial dysfunction and decreased energy metabolism renders cancers resistant to checkpoint (82, 107). We will test the hypothesis that Mito-MGN will reverse T cell exhaustion and work independently and/or cooperatively with checkpoint inhibitors such as anti-PD-L1 in anti-melanoma immune responses. Initial experiments will group mice into Mito-MGN alone, anti-PD-L1 antibody at 250 µg only, or combinations of Mito-MGN with anti-PD-L1 treatment arms. The negative control groups will receive vehicle or 250 µg isotype control antibody. Mito-MGN will be administered three times per week by intra-tumoral injection starting on day 1 post-implantation while anti-PD-L1 will be administered on days 7, 11, and 16. The rationale for this initial treatment sequence is that we believe Mito-MGN will increase T cell proliferation and/or infiltration prior to blocking the suppressive effects mediated by PD-L1 blockade. Experiments reversing the sequence, with anti-PD-L1 treatment preceding the OXPHOS inhibitor will also be completed. Tumor wet weights and metastasis will be measured, and the tumor processed for flow cytometry. EPR will also be performed to assess metabolic reprogramming, as assessed by an increase in oxidized Acn signal (shown in FIG. 34).

We predict that Mito-MGN will increase levels of T cells throughout the melanoma tumor mass. Levels of PD-L1 on the tumors may diminish with Mito-MGN treatment (92). While not expected, if $CD8^+$ T cell proliferation remains unchanged upon treatment, we would shift our attention to the effects of Mito-MGN on myeloid cells or natural killer cells. Indeed, because OXPHOS supports the differentiation of regulatory T cells and suppressive myeloid cells, we expect our immune profile analysis to detect decreases in both of those suppressive cell populations. Other checkpoint inhibitor antibodies against CTLA-4 or PD-1 expressed on immune cell subsets would be a viable complement for the proposed checkpoint inhibitor experiments (25). In vivo monitoring of T cell-cancer interactions will utilize our published intravital microscopy approach to visualize and quantify TIL movement in the melanoma microenvironment in real time, using Imaris software to identify and track individual TILs and calculate speed and contact time with melanoma cells (108-111). It is also possible that any elevation in T cells within the tumor may reflect Mito-MGN stimulating the mobilization of tumor reactive, as well as non-tumor reactive, T cells, into the peripheral blood, where they can then traffic into the melanoma tumor. To assess this potential, we will use flow cytometry to quantify T cells within the peripheral blood and, use IFNγ ELISPOT to determine the tumor reactivity of any circulating T cells. Experiments will be repeated in $RAG^{-/-}$ mice that lack T and B cells to rigorously resolve if the therapeutic effects of Mito-MGN are T cell mediated. To assess the potential for Mito-MGN to increase TILs by stimulating T cell migration and tumor infiltration, we will use $CXCR3^{-/-}$ mice to disrupt T cell chemotaxis. Autophagy plays a role in down-regulating tumor immune suppression in myeloid-derived suppressor cells or suppressive tumor-associated macrophages, a potential we fully expect our immune profiling to detect. If myeloid cell populations are affected by Mito-MGN, we would use flow cytometry to measure their activation and cell culture suppression assays to investigate functional changes. Organoid-T cell co-culture systems show increasing utility and provide an approach with which to examine tumor-immune interactions in a more physiologically relevant microenvironment. We have recently established a patient-derived organoid biomimetic system in pancreatic cancer (112) and envision future studies using this approach to examine ROS and mitophagy interactions between melanoma and reactive T cells (113,114).

REFERENCES

Alas, S., and Bonavida, B. (2003). Inhibition of constitutive STAT3 activity sensitizes resistant non-Hodgkin's lymphoma and multiple myeloma to chemotherapeutic drug-mediated apoptosis. Clin Cancer Res 9, 316-326.

Anders, S., Pyl, P. T., and Huber, W. (2015). HTSeq—a Python framework to work with high-throughput sequencing data. Bioinformatics 31, 166-169.

Bewry, N. N., Nair, R. R., Emmons, M. F., Boulware, D., Pinilla-Ibarz, J., and Hazlehurst, L. A. (2008). Stat3 contributes to resistance toward BCR-ABL inhibitors in a bone marrow microenvironment model of drug resistance. Mol Cancer Ther 7, 3169-3175.

Bradford, J. R., Farren, M., Powell, S. J., Runswick, S., Weston, S. L., Brown, H., Delpuech, O., Wappett, M., Smith, N. R., Carr, T. H., et al. (2013). RNA-Seq Differentiates Tumour and Host mRNA Expression Changes Induced by Treatment of Human Tumour Xenografts with the VEGFR Tyrosine Kinase Inhibitor Cediranib. PLoS One 8, e66003.

Chen, F., Wang, T., Wu, Y. F., Gu, Y., Xu, X. L., Zheng, S., and Hu, X. (2004). Honokiol: a potent chemotherapy candidate for human colorectal carcinoma. World J Gastroenterol 10, 3459-3463.

Chen, Y. J., Wu, C. L., Liu, J. F., Fong, Y. C., Hsu, S. F., Li, T. M., Su, Y. C., Liu, S. H., and Tang, C. H. (2010). Honokiol induces cell apoptosis in human chondrosarcoma cells through mitochondrial dysfunction and endoplasmic reticulum stress. Cancer Lett 291, 20-30.

Cheng, G., Zielonka, J., Dranka, B. P., McAllister, D., Mackinnon, A. C., Joseph, J., and Kalyanaraman, B. (2012). Mitochondria-targeted drugs synergize with 2-deoxyglucose to trigger breast cancer cell death. Cancer Res 72, 2634-2644.

Cheng, G., Zielonka, J., McAllister, D., Tsai, S., Dwinell, M. B., and Kalyanaraman, B. (2014). Profiling and targeting of cellular bioenergetics: inhibition of pancreatic cancer cell proliferation. Br J Cancer, 1-9.

Cheng, G., Zielonka, J., McAllister, D. M., Mackinnon, a. C., Joseph, J., Dwinell, M. B., and Kalyanaraman, B. (2013). Mitochondria-targeted vitamin E analogs inhibit breast cancer cell energy metabolism and promote cell death. BMC Cancer 13, 285-285.

Crane, C., Panner, A., Pieper, R. O., Arbiser, J., and Parsa, A. T. (2009). Honokiol-mediated inhibition of PI3K/mTOR pathway: a potential strategy to overcome immunoresistance in glioma, breast, and prostate carcinoma without impacting T cell function. J Immunother 32, 585-592.

De Simone, V., Franze, E., Ronchetti, G., Colantoni, A., Fantini, M. C., Di Fusco, D., Sica, G. S., Sileri, P., MacDonald, T. T., Pallone, F., et al. (2015). Th17-type cytokines, IL-6 and TNF-alpha synergistically activate STAT3 and NF-kB to promote colorectal cancer cell growth. Oncogene 34, 3493-3503.

Deng, J., Qian, Y., Geng, L., Chen, J., Wang, X., Xie, H., Yan, S., Jiang, G., Zhou, L., and Zheng, S. (2008). Involvement of p38 mitogen-activated protein kinase pathway in honokiol-induced apoptosis in a human hepatoma cell line (hepG2). Liver Int 28, 1458-1464.

Gane, E. J., Weilert, F., Orr, D. W., Keogh, G. F., Gibson, M., Lockhart, M. M., Frampton, C. M., Taylor, K. M., Smith, R. A., and Murphy, M. P. (2010). The mitochondria-targeted anti-oxidant mitoquinone decreases liver damage in a phase 11 study of hepatitis C patients. Liver Int 30, 1019-1026.

Garcia, A., Zheng, Y., Zhao, C., Toschi, A., Fan, J., Shraibman, N., Brown, H. A., Bar-Sagi, D., Foster, D. A., and Arbiser, J. L. (2008). Honokiol suppresses survival signals mediated by Ras-dependent phospholipase D activity in human cancer cells. Clin Cancer Res 14, 4267-4274.

Goldberg, S. B., Contessa, J. N., Omay, S. B., and Chiang, V. (2015). Lung Cancer Brain Metastases. Cancer J 21, 398-403.

Hahm, E. R., and Singh, S. V. (2007). Honokiol causes G0-G1 phase cell cycle arrest in human prostate cancer cells in association with suppression of retinoblastoma protein level/phosphorylation and inhibition of E2F1 transcriptional activity. Mol Cancer Ther 6, 2686-2695.

Jemal, A., Siegel, R., Xu, J., and Ward, E. (2010). Cancer statistics, 2010. CA: a cancer journal for clinicians 60, 277-300.

Koizumi, F., Shimoyama, T., Taguchi, F., Saijo, N., and Nishio, K. (2005). Establishment of a human non-small cell lung cancer cell line resistant to gefitinib. Int J Cancer 116, 36-44.

Langmead, B., Trapnell, C., Pop, M., and Salzberg, S. L. (2009). Ultrafast and memory-efficient alignment of short DNA sequences to the human genome. Genome Biol 10, R25.

Lee, H. J., Zhuang, G., Cao, Y., Du, P., Kim, H. J., and Settleman, J. (2014). Drug resistance via feedback activation of Stat3 in oncogene-addicted cancer cells. Cancer Cell 26, 207-221.

Lee, Y., Wang, Y., James, M., Jeong, J. H., and You, M. (2016). Inhibition of IGF1R signaling abrogates resistance to afatinib (BIBW2992) in EGFR T790M mutant lung cancer cells. Mol Carcinog 55, 991-1001.

Li, P., Zhang, D., Shen, L., Dong, K., Wu, M., Ou, Z., and Shi, D. (2016). Redox homeostasis protects mitochondria through accelerating ROS conversion to enhance hypoxia resistance in cancer cells. Sci Rep 6, 22831.

Lin, J. W., Chen, J. T., Hong, C. Y., Lin, Y. L., Wang, K. T., Yao, C. J., Lai, G. M., and Chen, R. M. (2012). Honokiol traverses the blood-brain barrier and induces apoptosis of neuroblastoma cells via an intrinsic bax-mitochondrion-cytochrome c-caspase protease pathway. Neuro Oncol 14, 302-314.

Lin, L., Liu, A., Peng, Z., Lin, H. J., Li, P. K., Li, C., and Lin, J. (2011). STAT3 is necessary for proliferation and survival in colon cancer-initiating cells. Cancer Res 71, 7226-7237.

Martin, S., Lamb, H. K., Brady, C., Lefkove, B., Bonner, M. Y., Thompson, P., Lovat, P. E., Arbiser, J. L., Hawkins, A. R., and Redfern, C. P. (2013). Inducing apoptosis of cancer cells using small-molecule plant compounds that bind to GRP78. Br J Cancer 109, 433-443.

McManus, M. J., Murphy, M. P., and Franklin, J. L. (2011). The mitochondria-targeted antioxidant MitoQ prevents loss of spatial memory retention and early neuropathology in a transgenic mouse model of Alzheimer's disease. J Neurosci 31, 15703-15715.

Nair, R. R., Tolentino, J. H., and Hazlehurst, L. A. (2012). Role of STAT3 in Transformation and Drug Resistance in CML. Front Oncol 2, 30.

Nguyen, D. X., Chiang, A. C., Zhang, X. H., Kim, J. Y., Kris, M. G., Ladanyi, M., Gerald, W. L., and Massague, J. (2009). WNT/TCF signaling through LEF1 and HOXB9 mediates lung adenocarcinoma metastasis. Cell 138, 51-62.

Pan, J., Zhang, Q., Liu, Q., Komas, S. M., Kalyanaraman, B., Lubet, R. A., Wang, Y., and You, M. (2014). Honokiol inhibits lung tumorigenesis through inhibition of mitochondrial function. Cancer Prev Res (Phila) 7, 1149-1159.

Park, E. J., Min, H. Y., Chung, H. J., Hong, J. Y., Kang, Y. J., Hung, T. M., Youn, U. J., Kim, Y. S., Bae, K., Kang, S. S., and Lee, S. K. (2009). Down-regulation of c-Src/EGFR-mediated signaling activation is involved in the honokiol-induced cell cycle arrest and apoptosis in MDA-MB-231 human breast cancer cells. Cancer Lett 277, 133-140.

Phelps, R. M., Johnson, B. E., Ihde, D. C., Gazdar, A. F., Carbone, D. P., McClintock, P. R., Linnoila, R. I., Matthews, M. J., Bunn, P. A., Jr., Carney, D., et al. (1996). NCI-Navy Medical Oncology Branch cell line data base. J Cell Biochem Suppl 24, 32-91.

Pillai, V. B., Samant, S., Sundaresan, N. R., Raghuraman, H., Kim, G., Bonner, M. Y., Arbiser, J. L., Walker, D. I., Jones, D. P., Gius, D., and Gupta, M. P. (2015). Honokiol blocks and reverses cardiac hypertrophy in mice by activating mitochondrial Sirt3. Nat Commun 6, 6656.

Robinson, M. D., McCarthy, D. J., and Smyth, G. K. (2010). edgeR: a Bioconductor package for differential expression analysis of digital gene expression data. Bioinformatics 26, 139-140.

Rossello, F. J., Tothill, R. W., Britt, K., Marini, K. D., Falzon, J., Thomas, D. M., Peacock, C. D., Marchionni, L., Li, J., Bennett, S., et al. (2013). Next-generation sequence analysis of cancer xenograft models. PLoS One 8, e74432.

Trapnell, C., Pachter, L., and Salzberg, S. L. (2009). TopHat: discovering splice junctions with RNA-Seq. Bioinformatics 25, 1105-1111.

Tsai, T. H., Chou, C. J., Cheng, F. C., and Chen, C. F. (1994). Pharmacokinetics of honokiol after intravenous administration in rats assessed using high-performance liquid chromatography. J Chromatogr B Biomed Appl 655, 41-45.

Tse, A. K., Wan, C. K., Shen, X. L., Yang, M., and Fong, W. F. (2005). Honokiol inhibits TNF-alpha-stimulated NF-kappaB activation and NF-kappaB-regulated gene expression through suppression of IKK activation. Biochem Pharmacol 70, 1443-1457.

Vazquez-Martin, A., Cufi, S., Oliveras-Ferraros, C., Torres-Garcia, V. Z., Corominas-Faja, B., Cuyas, E., Bonavia, R., Visa, J., Martin-Castillo, B., Barrajon-Catalan, E., et al. (2013). IGF-1R/epithelial-to-mesenchymal transition (EMT) crosstalk suppresses the erlotinib-sensitizing effect of EGFR exon 19 deletion mutations. Sci Rep 3, 2560.

Wang, X., Duan, X., Yang, G., Zhang, X., Deng, L., Zheng, H., Deng, C., Wen, J., Wang, N., Peng, C., et al. (2011). Honokiol crosses BBB and BCSFB, and inhibits brain tumor growth in rat 9L intracerebral gliosarcoma model and human U251 xenograft glioma model. PLoS One 6, e18490.

Wu, J., Patmore, D. M., Jousma, E., Eaves, D. W., Breving, K., Patel, A. V., Schwartz, E. B., Fuchs, J. R., Cripe, T. P., Stemmer-Rachamimov, A. O., and Ratner, N. (2014). EGFR-STAT3 signaling promotes formation of malignant peripheral nerve sheath tumors. Oncogene 33, 173-180.

Yang, H., Yamazaki, T., Pietrocola, F., Zhou, H., Zitvogel, L., Ma, Y., and Kroemer, G. (2015). STAT3 Inhibition Enhances the Therapeutic Efficacy of Immunogenic Chemotherapy by Stimulating Type 1 Interferon Production by Cancer Cells. Cancer Res 75, 3812-3822.

Yau, C. Y., Wheeler, J. J., Sutton, K. L., and Hedley, D. W. (2005). Inhibition of integrin-linked kinase by a selective small molecule inhibitor, QLT0254, inhibits the PI3K/PKB/mTOR, Stat3, and FKHR pathways and tumor growth, and enhances gemcitabine-induced apoptosis in human orthotopic primary pancreatic cancer xenografts. Cancer Res 65, 1497-1504.

Yu, P., Yu, H., Guo, C., Cui, Z., Chen, X., Yin, Q., Zhang, P., Yang, X., Cui, H., and Li, Y. (2015). Reversal of doxorubicin resistance in breast cancer by mitochondria-targeted pH-responsive micelles. Acta Bio mater 14, 115-124.

Zhang, Q., Raje, V., Yakovlev, V. A., Yacoub, A., Szczepanek, K., Meier, J., Derecka, M., Chen, Q., Hu, Y., Sisler, J., et al. (2013). Mitochondrial localized Stat3 promotes breast cancer growth via phosphorylation of serine 727. J Biol Chem 288, 31280-31288.

Zhou, J., Wulfkuhle, J., Zhang, H., Gu, P., Yang, Y., Deng, J., Margolick, J. B., Liotta, L. A., Petricoin, E., 3rd, and Zhang, Y. (2007). Activation of the PTEN/mTOR/STAT3 pathway in breast cancer stem-like cells is required for viability and maintenance. Proc Natl Acad Sci USA 104, 16158-16163.

BIBLIOGRAPHY

Batus M, Waheed S, Ruby C, Petersen L, Bines S D, Kaufman H L. 2013. Optimal management of metastatic melanoma: current strategies and future directions. *Am J Clin Dermato*/14:179-94

Miller K D, Siegel R L, Lin C C, Mariotto A B, Kramer J L, Rowland J H, Stein K D, Alteri R, Jemal A. 2016. Cancer treatment and survivorship statistics, 2016. *CA Cancer J Clin* 66: 271-89

Domingues B, Lopes J M, Soares P, Populo H. 2018. Melanoma treatment in review. *Immunotargets Ther* 7: 35-49

Tsao H, Goel V, Wu H, Yang G, Haluska F G. 2004. Genetic interaction between NRAS and BRAF mutations and PTEN/MMAC1 inactivation in melanoma. *J Invest Dermatol* 122:337-41

Abildgaard C, Dahl C, Basse A L, Ma T, Guldberg P. 2014. Bioenergetic modulation with dichloroacetate reduces the growth of melanoma cells and potentiates their response to BRAFV600E inhibition. *J Transl Med* 12: 247

Cheng G, Zielonka J, Dranka B P, McAllister D, Mackinnon A C, Jr., Joseph J, Kalyanaraman B. 2012. Mitochondria-targeted drugs synergize with 2-deoxyglucose to trigger breast cancer cell death. *Cancer Res* 72: 2634-44

Cheng G, Zielonka J, McAllister D M, Mackinnon A C, Jr., Joseph J, Dwinell M B, Kalyanaraman B. 2013. Mitochondria-targeted vitamin E analogs inhibit breast cancer cell energy metabolism and promote cell death. *BMC. Cancer* 13: 285

Cheng G, Zielonka J, McAllister D, Tsai S, Dwinell M B, Kalyanaraman B. 2014. Profiling and targeting of cellular bioenergetics: inhibition of pancreatic cancer cell proliferation. *Br. J. Cancer* 111: 85-93

Cheng G, Zielonka J, McAllister D, Hardy M, Ouari O, Joseph J, Dwinell M B, Kalyanaraman B. 2015. Antiproliferative effects of mitochondria-targeted cationic antioxidants and analogs: Role of mitochondrial bioenergetics and energy-sensing mechanism. *Cancer Lett* 365:96-106

Cheng G, Zielonka J, Ouari O, Lopez M, McAllister D, Boyle K, Barrios C S, Weber J J, Johnson B D, Hardy M, Dwinell M B, Kalyanaraman B. 2016. Mitochondria-Targeted Analogues of Metformin Exhibit Enhanced Antiproliferative and Radiosensitizing Effects in Pancreatic Cancer Cells. *Cancer Res* 76: 3904-15

Kalyanaraman B, Cheng G, Hardy M, Ouari O, Lopez M, Joseph J, Zielonka J, Dwinell M B. 2018. A review of the basics of mitochondrial bioenergetics, metabolism, and related signaling pathways in cancer cells: Therapeutic targeting of tumor mitochondria with lipophilic cationic compounds. *Redox Biol* 14: 316-27

Boyle K A, Van Wickle J, Hill R B, Marchese A, Kalyanaraman B, Dwinell M B. 2018. Mitochondria-targeted drugs stimulate mitophagy and abrogate colon cancer cell proliferation. *J Biol Chem* 293: 14891-904

Nadakavukaren K K, Nadakavukaren J J, Chen L B. 1985. Increased rhodamine 123 uptake by carcinoma cells. *Cancer Res* 45: 6093-9

Modica-Napolitano J S, Aprille J R. 1987. Basis for the selective cytotoxicity of rhodamine 123. *Cancer Res* 47: 4361-5

Hong S K, Starenki D, Wu P K, Park J I. 2017. Suppression of B-Raf(V600E) melanoma cell survival by targeting mitochondria using triphenyl-phosphonium-conjugated nitroxide or ubiquinone. *Cancer Biol Ther* 18: 106-14

Smith R A, Adlam V J, Blaikie F H, Manas A R, Porteous C M, James A M, Ross M F, Logan A, Cocheme H M, Trnka J, Prime T A, Abakumova I, Jones B A, Filipovska A, Murphy M P. 2008. Mitochondria-targeted antioxidants in the treatment of disease. *Ann. N. Y. Acad. Sci* 1147: 105-11

Cheng G, Lopez M, Zielonka J, Hauser A D, Joseph J, McAllister D, Rowe J J, Sugg S L, Williams C L, Kalyanaraman B. 2011. Mitochondria-targeted nitroxides exacerbate fluvastatin-mediated cytostatic and cytotoxic effects in breast cancer cells. *Cancer Biol. Ther* 12:707-17

Mukhopadhyay P, Horvath B, Zsengeller Z, Batkai S, Cao Z, Kechrid M, Holovac E, Erdelyi K, Tanchian G, Liaudet L, Stillman I E, Joseph J, Kalyanaraman B, Pacher P. 2012. Mitochondrial reactive oxygen species generation triggers inflammatory response and tissue injury associated with hepatic ischemia-reperfusion: Therapeutic potential of mitochondrially targeted antioxidants. *Free Radic. Biol. Med* 53: 1123-38

Chandran K, Aggarwal D, Migrino R Q, Joseph J, McAllister D, Konorev E A, Antholine W E, Zielonka J, Srinivasan S, Avadhani N G, Kalyanaraman B. 2009. Doxorubicin inactivates myocardial cytochrome c oxidase in rats: cardioprotection by Mito-Q. *Biophys. J* 96: 1388-98

Gide T N, Wilmott J S, Scolyer R A, Long G V. 2018. Primary and Acquired Resistance to Immune Checkpoint Inhibitors in Metastatic Melanoma. *Clin Cancer Res* 24: 1260-70

Vazquez F, Lim J H, Chim H, Bhalla K, Girnun G, Pierce K, Clish C B, Granter S R, Widlund H R, Spiegelman B M, Puigserver P. 2013. PGC1α expression defines a subset of human melanoma tumors with increased mitochondrial capacity and resistance to oxidative stress. *Cancer Cell* 23: 287-301

Roesch A, Vultur A, Bogeski I, Wang H, Zimmermann K M, Speicher D, Korbel C, Laschke M W, Gimotty P A, Philipp S E, Krause E, Patzold S, Villanueva J, Krepler C, Fukunaga-Kalabis M, Hoth M, Bastian B C, Vogt T, Herlyn M. 2013. Overcoming intrinsic multidrug resistance in melanoma by blocking the mitochondrial respiratory chain of slow-cycling JARID1B(high) cells. *Cancer Cell* 23:811-25

Hardeman K N, Peng C, Paudel B B, Meyer C T, Luong T, Tyson D R, Young J D, Quaranta V, Fessel J P. 2017. Dependence On Glycolysis Sensitizes BRAF-mutated Melanomas For Increased Response To Targeted BRAF Inhibition. *Sci Rep* 7: 42604

Haq R, Shoag J, Andreu-Perez P, Yokoyama S, Edelman H, Rowe G C, Frederick D T, Hurley A D, Nellore A, Kung A L, Wargo J A, Song J S, Fisher D E, Arany Z, Widlund H R. 2013. Oncogenic BRAF regulates oxidative metabolism via PGC1α and MITF. *Cancer Cell* 23:302-15

Bengsch F, Knoblock D M, Liu A, McAllister F, Beatty G L. 2017. CTLA-4/CD80 pathway regulates T cell infiltration into pancreatic cancer. *Cancer Immunol Immunother* 66:1609-17

Molina J R, Sun Y, Protopopova M, Gera S, Bandi M, Bristow C, McAfoos T, Morlacchi P, Ackroyd J, Agip A A, Al-Atrash G, Asara J, Bardenhagen J, Carrillo C C, Carroll C, Chang E, Ciurea S, Cross J B, Czako B, Deem A, Daver N, de Groot J F, Dong J W, Feng N, Gao G, Gay J, Do M G, Greer J, Giuliani V, Han J, Han L, Henry V K, Hirst J, Huang S, Jiang Y, Kang Z, Khor T, Konoplev S, Lin Y H, Liu G, Lodi A, Lofton T, Ma H, Mahendra M, Matre P, Mullinax R, Peoples M, Petrocchi A, Rodriguez-Canale J, Serreli R, Shi T, Smith M, Tabe Y, Theroff J, Tiziani S, Xu Q, Zhang Q, Muller F, DePinho R A, Toniatti C, Draetta G F, Heffernan T P, Konopleva M, Jones P, Di Francesco M E, Marszalek J R. 2018. An inhibitor of oxidative phosphorylation exploits cancer vulnerability. *Nat Med* 24:1036-46

Weinberg F, Hamanaka R, Wheaton W W, Weinberg S, Joseph J, Lopez M, Kalyanaraman B, Mutlu G M, Budinger G R, Chandel N S. 2010. Mitochondrial metabolism and ROS generation are essential for Kras-mediated tumorigenicity. *Proc. Natl. Acad. Sci. U. S. A* 107:8788-93

Luengo A, Gui D Y, Vander Heiden M G. 2017. Targeting Metabolism for Cancer Therapy. *Cell Chem Biol* 24: 1161-80

Vander Heiden M G, DeBerardinis R J. 2017. Understanding the Intersections between Metabolism and Cancer Biology. *Cell* 168: 657-69

Weinberg S E, Chandel N S. 2015. Targeting mitochondria metabolism for cancer therapy. *Nat Chem Biol* 11: 9-15

Zielonka J, Kalyanaraman B. 2018. Small-molecule luminescent probes for the detection of cellular oxidizing and nitrating species. *Free Radic Biol Med* 128: 3-22

Sarrica A, Kirika N, Romeo M, Salmona M, Diomede L. 2018. Safety and Toxicology of Magnolol and Honokiol. *Planta Med* 84: 1151-64

Zielonka J, Joseph J, Sikora A, Hardy M, Ouari O, Vasquez-Vivar J, Cheng G, Lopez M, Kalyanaraman B. 2017. Mitochondria-Targeted Triphenylphosphonium-Based Compounds: Syntheses, Mechanisms of Action, and Therapeutic and Diagnostic Applications. *Chem Rev* 117: 10043-120

Sena L A, L1 S, Jairaman A, Prakriya M, Ezponda T, Hildeman D A, Wang C R, Schumacker P T, Licht J D, Perlman H, Bryce P J, Chandel N S. 2013. Mitochondria are required for antigen-specific T cell activation through reactive oxygen species signaling. *Immunity* 38: 225-36

Weinberg S E, Sena L A, Chandel N S. 2015. Mitochondria in the regulation of innate and adaptive immunity. *Immunity* 42: 406-17

Schlie K, Westerback A, DeVorkin L, Hughson L R, Brandon J M, MacPherson S, Gadawski I, Townsend K N, Poon V I, Elrick M A, Cote H C, Abraham N, Wherry E J, Mizushima N, Lum I I. 2015. Survival of effector CD8+ T cells during influenza infection is dependent on autophagy. *J Immunol* 194:4277-86

Chamoto K, Chowdhury P S, Kumar A, Sonomura K, Matsuda F, Fagarasan S, Honjo T. 2017. Mitochondrial activation chemicals synergize with surface receptor PD-1 blockade for T cell-dependent antitumor activity. *Proc Natl Acad Sci USA* 114: E761-e70

Hosios A M, Vander Heiden M G. 2018. The redox requirements of proliferating mammalian cells. *J Biol Chem* 293: 7490-8

Beier U H, Angelin A, Akimova T, Wang L, Liu Y, Xiao H, Koike M A, Hancock S A, Bhatti T R, Han R, Jiao J, Veasey S C, Sims C A, Baur J A, Wallace D C, Hancock W W. 2015. Essential role of mitochondrial energy metabolism in Foxp3(+) T-regulatory cell function and allograft survival. *Faseb j* 29: 2315-26

Goffaux G, Hammami I, Jolicoeur M. 2017. A Dynamic Metabolic Flux Analysis of Myeloid-Derived Suppressor Cells Confirms Immunosuppression-Related Metabolic Plasticity. *Sci Rep* 7: 9850

Le Bourgeois T, Strauss L, Aksoylar H I, Daneshmandi S, Seth P, Patsoukis N, Boussiotis V A. 2018. Targeting T Cell Metabolism for Improvement of Cancer Immunotherapy. *Front Oncol* 8: 237

Kaelin W G, Jr. 2005. The concept of synthetic lethality in the context of anticancer therapy. *Nat Rev Cancer* 5: 689-98

Brunen D, Bernards R. 2017. Drug therapy: Exploiting synthetic lethality to improve cancer therapy. *Nat Rev Clin Oncol* 14: 331-2

Gopal Y N, Rizos H, Chen G, Deng W, Frederick D T, Cooper Z A, Scolyer R A, Pupo G, Komurov K, Sehgal V, Zhang J, Patel L, Pereira C G, Broom B M, Mills G B, Ram P, Smith P D, Wargo J A, Long G V, Davies M A. 2014. Inhibition of mTORC1/2 overcomes resistance to MAPK pathway inhibitors mediated by PGC1α and oxidative phosphorylation in melanoma. *Cancer Res* 74: 7037-47

Schockel L, Glasauer A, Basit F, Bitschar K, Truong H, Erdmann G, Algire C, Hagebarth A, Willems P H, Kopitz C, Koopman W J, Heroult M. 2015. Targeting mitochondrial complex I using BAY 87-2243 reduces melanoma tumor growth. *Cancer Metab* 3: 11

Liberman E A, Topaly V P, Tsofina L M, Jasaitis A A, Skulachev V P. 1969. Mechanism of coupling of oxidative phosphorylation and the membrane potential of mitochondria. *Nature* 222: 1076-8

Lichtshtein D, Kaback H R, Blume A J. 1979. Use of a lipophilic cation for determination of membrane potential in neuroblastoma-glioma hybrid cell suspensions. *Proc Natl Acad Sci USA* 76: 650-4

Hanahan D, Weinberg R A. 2011. Hallmarks of cancer: the next generation. *Cell* 144: 646-74

Cheng G, Zielonka M, Dranka B, Kumar S N, Myers C R, Bennett B, Garces A M, Dias Duarte Machado L G, Thiebaut D, Ouari O, Hardy M, Zielonka J, Kalyanaraman B. 2018. Detection of mitochondria-generated reactive oxygen species in cells using multiple probes and methods: Potentials, pitfalls, and the future. *J Biol Chem* 293: 10363-80

Kalyanaraman B, Cheng G, Zielonka J, Bennett B. 2018. Low-Temperature EPR Spectroscopy as a Probe-Free Technique for Monitoring Oxidants Formed in Tumor Cells and Tissues: Implications in Drug Resistance and OXPHOS-Targeted Therapies. *Cell Biochem Biophys* 2018 Sep. 26. doi: 10.1007/s12013-018-0858-1. [Epub ahead of print]

Brahmer J R, Drake C G, Wollner I, Powderly J D, Picus J, Sharfman W H, Stankevich E, Pons A, Salay T M, McMiller T L, Gilson M M, Wang C, Selby M, Taube J M, Anders R, Chen L, Korman A J, Pardoll D M, Lowy I, Topalian S L. 2010. Phase I study of single-agent anti-programmed death-1 (MDX-1106) in refractory solid tumors: safety, clinical activity, pharmacodynamics, and immunologic correlates. *J Clin Oncol* 28: 3167-75

Chen D S, Mailman I. 2013. Oncology meets immunology: the cancer-immunity cycle. *Immunity* 39: 1-10

Hamid O, Robert C, Daud A, Hodi F S, Hwu W J, Kefford R, Wolchok J D, Hersey P, Joseph R W, Weber J S, Dronca R, Gangadhar T C, Patnaik A, Zarour H, Joshua A M, Gergich K, Elassaiss-Schaap J, Algazi A, Mateus C, Boasberg P, Tumeh P C, Chmielowski B, Ebbinghaus S W, L1 X N, Kang S P, Ribas A. 2013. Safety and tumor responses with lam brolizumab (anti-PD-1) in melanoma. *N Engl J Med* 369: 134-44

Bryant K G, Chae Y C, Martinez R L, Gordon J C, Elokely K M, Kossenkov A V, Grant S, Childers W E, Abou-Gharbia M, Altieri D C. 2017. A Mitochondrial-targeted purine-based HSP90 antagonist for leukemia therapy. *Oncotarget* 8: 112184-98

Ozsvari B, Sotgia F, Lisanti M P. 2018. Exploiting mitochondrial targeting signal(s), TPP and bis-TPP, for eradicating cancer stem cells (CSCs). *Aging (Albany NY)* 10: 229-40

Titova E, Shagieva G, Ivanova O, Domnina L, Domninskaya M, Strelkova O, Khromova N, Kopnin P, Chernyak B, Skulachev V, Dugina V. 2018. Mitochondria-targeted antioxidant SkQ1 suppresses fibrosarcoma and rhabdomyosarcoma tumour cell growth. *Cell Cycle* 17: 1797-811

Hardy M, Zielonka J, Karoui H, Sikora A, Michalski R, Podsiadly R, Lopez M, Vasquez-Vivar J, Kalyanaraman B, Ouari O. 2018. Detection and Characterization of Reactive Oxygen and Nitrogen Species in Biological Systems by Monitoring Species-Specific Products. *Antioxid Redox Signal* 28: 1416-32

Nakamura K, Yoshikawa N, Yamaguchi Y, Kagota S, Shinozuka K, Kunitomo M. 2002. Characterization of mouse melanoma cell lines by their mortal malignancy using an experimental metastatic model. *Life Sci* 70: 791-8

Melnikova V O, Bolshakov S V, Walker C, Ananthaswamy H N. 2004. Genomic alterations in spontaneous and carcinogen-induced murine melanoma cell lines. *Oncogene* 23: 2347-56

Roy I, McAllister D, Gorse E, Dixon K, Piper C T, Zimmerman N P, Getschman A E, Tsai S, Engle D D, Evans D B, Volkman B F, Kalyanaraman B, Dwinell M B. 2015. Pancreatic Cancer Cell Migration and Metastasis Is Regulated by Chemokine-Biased Agonism and Bioenergetic Signaling. *Cancer Res* 75: 3529-42

Pan J Y L, Cheng G, Zielonka J, Zhang Q, Bajzikova M, Xiong D, Tsaih S-W, Hardy M, Flister M, Olsen C M, Wang Y, Vang O, Neuzil J, Myers C R, Kalyanaraman B, You M. 2018. Mitochondria-Targeted Honokiol Confers a Striking Inhibitory Effect on Lung Cancer via Inhibiting Complex I Activity. *iScience* 3: 192-207

Wood Z A, Poole L B, Karplus P A. 2003. Peroxiredoxin evolution and the regulation of hydrogen peroxide signaling. *Science* 300: 650-3

Cox A G, Winterbourn C C, Hampton M B. 2009. Mitochondrial peroxiredoxin involvement in antioxidant defence and redox signalling. *Biochem J* 425: 313-25

Myers C R. 2016. Enhanced targeting of mitochondrial peroxide defense by the combined use of thiosemicarbazones and inhibitors of thioredoxin reductase. *Free Radic Biol Med* 91: 81-92

Holmstrom K M, Finkel T. 2014. Cellular mechanisms and physiological consequences of redox-dependent signalling. *Nat Rev Mol Cell Biol* 15:411-21

Andreyev A Y, Kushnareva Y E, Murphy A N, Starkov A A. 2015. Mitochondrial ROS Metabolism: 10 Years Later. *Biochemistry (Mosc)* 80: 517-31

Johnson L V, Walsh M L, Bockus B J, Chen L B. 1981. Monitoring of relative mitochondrial membrane potential in living cells by fluorescence microscopy. *J Cell Biol* 88: 526-35

Hardie D G, Ashford M L. 2014. AMPK: regulating energy balance at the cellular and whole body levels. *Physiology. (Bethesda.)* 29: 99-107

Allavena G, Boyd C, Oo K S, Maellaro E, Zhivotovsky B, Kaminskyy V O. 2016. Suppressed translation and ULK1 degradation as potential mechanisms of autophagy limitation under prolonged starvation. *Autophagy* 12: 2085-97

Katayama H, Kogure T, Mizushima N, Yoshimori T, Miyawaki A. 2011. A sensitive and quantitative technique for detecting autophagic events based on lysosomal delivery. *Chem Biol* 18: 1042-52

Sun N, Malide D, Liu J, Rovira, I I, Combs C A, Finkel T. 2017. A fluorescence-based imaging method to measure in vitro and in vivo mitophagy using mt-Keima. *Nat Protoc* 12:1576-87

Das S, Alhasson F, Dattaroy D, Pourhoseini S, Seth R K, Nagarkatti M, Nagarkatti P S, Michelotti G A, Diehl A M, Kalyanaraman B, Chatterjee S. 2015. NADPH Oxidase-Derived Peroxynitrite Drives Inflammation in Mice and Human Nonalcoholic Steatohepatitis via TLR4-Lipid Raft Recruitment. *Am J Pathol* 185: 1944-57

Chandrashekaran V, Seth R K, Dattaroy D, Alhasson F, Ziolenka J, Carson J, Berger F G, Kalyanaraman B, Diehl A M, Chatterjee S. 2017. HMGB1-RAGE pathway drives peroxynitrite signaling-induced IBD-like inflammation in murine nonalcoholic fatty liver disease. *Redox Biol* 13:8-19

Deng J, Wang K, Wang M, Yu P, Mao L. 2017. Mitochondria Targeted Nanoscale Zeolitic Imidazole Framework-90 for ATP Imaging in Live Cells. *J Am Chem Soc* 139: 5877-82

Van de Bittner G C, Dubikovskaya E A, Bertozzi C R, Chang C I 2010. In vivo imaging of hydrogen peroxide production in a murine tumor model with a chemoselective bioluminescent reporter. *Proc Natl Acad Sci USA* 107: 21316-21

Zielonka J, Podsiadly R, Zielonka M, Hardy M, Kalyanaraman B. 2016. On the use of peroxy-caged luciferin (PCL-1) probe for bioluminescent detection of inflammatory oxidants in vitro and in vivo—Identification of reaction intermediates and oxidant-specific minor products. *Free Radic Biol Med* 99: 32-42

Wendt M K, Cooper A N, Dwinell M B. 2008. Epigenetic silencing of CXCL12 increases the metastatic potential of mammary carcinoma cells. *Oncogene* 27: 1461-71

Drury L J, Ziarek J J, Gravel S, Veldkamp C T, Takekoshi T, Hwang S T, Heveker N, Volkman B F, Dwinell M B. 2011. Monomeric and dimeric CXCL12 inhibit metastasis through distinct CXCR4 interactions and signaling pathways. *Proc. Natl. Acad. Sci. U.S.A.* 108: 17655-60

Roy I, Zimmerman N P, Mackinnon A C, Tsai S, Evans D B, Dwinell M B. 2014. CXCL12 chemokine expression suppresses human pancreatic cancer growth and metastasis. *PLoS. ONE* 9: e90400

Wendt M K, Drury U, Vongsa R A, Dwinell M B. 2008. Constitutive CXCL12 expression induces anoikis in colorectal carcinoma cells. *Gastroenterology* 135: 508-17

Brandt K E, Falls K C, Schoenfeld J D, Rodman S N, Gu Z, Zhan F, Cullen A, Wagner B A, Buettner G R, Allen B G, Berg D J, Spitz D R, Fath M A. 2018. Augmentation of intracellular iron using iron sucrose enhances the toxicity of pharmacological ascorbate in colon cancer cells. *Redox Biol* 14: 82-7

Gajewski T F. 2006. Identifying and overcoming immune resistance mechanisms in the melanoma tumor microenvironment. *Clin Cancer Res* 12: 2326s-30s Hodi F S, O'Day Si, McDermott D F, Weber R W, Sosman J A, Haanen J B, Gonzalez R, Robert C, Schadendorf D, Hassel J C, Akerley W, van den Eertwegh A J, Lutzky J, Lorigan P, Vaubel J M, Linette G P, Hogg D, Ottensmeier C H, Lebbe C, Peschel C, Quirt I, Clark J I, Wolchok J D, Weber J S, Tian J, Yellin M J, Nichol G M, Hoos A, Urba W J. 2010. Improved survival with ipilimumab in patients with metastatic melanoma. *N Engl J Med* 363: 711-23

Mihm M C, Jr., Clemente C G, Cascinelli N. 1996. Tumor infiltrating lymphocytes in lymph node melanoma metastases: a histopathologic prognostic indicator and an expression of local immune response. *Lab Invest* 74: 43-7

Chen D S, Mellman I. 2017. Elements of cancer immunity and the cancer-immune set point. *Nature* 541: 321-30

Gajewski T F, Schreiber H, Fu Y X. 2013. Innate and adaptive immune cells in the tumor microenvironment. *Nat Immunol* 14: 1014-22

Pearce E L, Walsh M C, Cejas R I, Harms G M, Shen H, Wang L S, Jones R G, Choi Y. 2009. Enhancing CD8 T-cell memory by modulating fatty acid metabolism. *Nature* 460: 103-7

Gubser P M, Bantug G R, Razik L, Fischer M, Dimeloe S, Hoenger G, Durovic B, Jauch A, Hess C. 2013. Rapid effector function of memory CD8+ T cells requires an immediate-early glycolytic switch. *Nat Immunol* 14: 1064-72

Eikawa S, Nishida M, Mizukami S, Yamazaki C, Nakayama E, Udono H. 2015. Immune-mediated antitumor effect by type 2 diabetes drug, metformin. *Proc Natl Acad Sci USA* 112:1809-14

Pereira F V, Melo A C L, Low J S, de Castro I A, Braga T T, Almeida D C, Batista de Lima A G U, Hiyane M I, Correa-Costa M, Andrade-Oliveira V, Origassa C S T, Pereira R M, Kaech S M, Rodrigues E G, Camara N O S. 2018. Metformin exerts antitumor activity via induction of multiple death pathways in tumor cells and activation of a protective immune response. *Oncotarget* 9: 25808-25

Li L, Wang L, Li J, Fan Z, Yang L, Zhang Z, Zhang C, Yue D, Qin G, Zhang T, Li F, Chen X, Ping Y, Wang D, Gao Q, He Q, Huang L, Li H, Huang J, Zhao X, Xue W, Sun Z, Lu J, Yu J J, Zhao J, Zhang B, Zhang Y. 2018. Metformin-Induced Reduction of CD39 and CD73 Blocks Myeloid-Derived Suppressor Cell Activity in Patients with Ovarian Cancer. *Cancer Res* 78:1779-91

Cha J H, Yang W H, Xia W, Wei Y, Chan L C, Lim S O, Li C W, Kim T, Chang S S, Lee H H, Hsu J L, Wang H L, Kuo C W, Chang W C, Hadad S, Purdie C A, McCoy A M, Cai S, Tu Y, Litton J K, Mittendorf E A, Moulder S L, Symmans W F, Thompson A M, Piwnica-Worms H, Chen C H, Khoo K H, Hung M C. 2018. Metformin Promotes Antitumor Immunity via Endoplasmic-Reticulum-Associated Degradation of PD-L1. *Mol Cell* 71: 606-20.e7

Ziegler P K, Bollrath J, Pallangyo C K, Matsutani T, Canli O, De Oliveira T, Diamanti M A, Muller N, Gamrekelashvili J, Putoczki T, Horst D, Mankan A K, Oner M G, Muller S, Muller-Hocker J, Kirchner T, Slotta-Huspenina J, Taketo M M, Reinheckel T, Drose S, Larner A C, Wels W S, Ernst M, Greten T F, Arkan M C, Korn T, Wirth D, Greten F R. 2018. Mitophagy in Intestinal Epithelial Cells Triggers Adaptive Immunity during Tumorigenesis. *Cell* 174: 88-101.e16

Ma X H, Piao S F, Dey S, McAfee Q, Karakousis G, Villanueva J, Hart L S, Levi S, Hu J, Zhang G, Lazova R, Klump V, Pawelek J M, Xu X, Xu W, Schuchter L M, Davies M A, Herlyn M, Winkler J, Koumenis C, Amaravadi R K. 2014. Targeting ER stress-induced autophagy overcomes BRAF inhibitor resistance in melanoma. *J Clin Invest* 124: 1406-17

Kaminski M M, Sauer S W, Kaminski M, Opp S, Ruppert T, Grigaravicius P, Grudnik P, Grone H J, Krammer P H, Gulow K. 2012. T cell activation is driven by an ADP-dependent glucokinase linking enhanced glycolysis with mitochondrial reactive oxygen species generation. *Cell Rep* 2:1300-15

Puleston D J, Simon A K. 2014. Autophagy in the immune system. *Immunology* 141: 1-8

Janji B, Viry E, Moussay E, Paggetti J, Arakelian T, Mgrditchian T, Messai Y, Noman M Z, Van Moer K, Hasmim M, Mami-Chouaib F, Berchem G, Chouaib S. 2016. The multifaceted role of autophagy in tumor evasion from immune surveillance. *Oncotarget* 7: 17591-607

Cunha L D, Yang M, Carter R, Guy C, Harris L, Crawford J C, Quarato G, Boada-Romero E, Kalkavan H, Johnson MDL, Natarajan S, Turnis M E, Finkelstein D, Opferman J T, Gawad C, Green D R. 2018. LC3-Associated Phagocytosis in Myeloid Cells Promotes Tumor Immune Tolerance. *Cell* 75: 429-41

Dowling S D, Macian F. 2018. Autophagy and T cell metabolism. *Cancer Lett* 419: 20-6

Mocholi E, Dowling S D, Botbol Y, Gruber R C, Ray A K, Vastert S, Shafit-Zagardo B, Coffer R I, Macian F. 2018. Autophagy Is a Tolerance-Avoidance Mechanism that Modulates TCR-Mediated Signaling and Cell Metabolism to Prevent Induction of T Cell Anergy. *Cell Rep* 24: 1136-50

Wang J M, Deng X, Gong W, Su S. 1998. Chemokines and their role in tumor growth and metastasis. *J. Immunol. Methods* 220: 1-17

Owens K M, Aykin-Burns N, Dayal D, Coleman M C, Domann F E, Spitz D R. 2012. Genomic instability induced by mutant succinate dehydrogenase subunit D (SDHD) is mediated by O2(-*) and H2O2. *Free Radic Biol Med* 52: 160-6

Buck M D, O'Sullivan D, Pearce E L. 2015. T cell metabolism drives immunity. *J Exp Med* 212: 1345-60

Araki K, Turner A P, Shaffer V O, Gangappa S, Keller S A, Bachmann M F, Larsen C P, Ahmed R. 2009. mTOR regulates memory CD8 T-cell differentiation. *Nature* 460: 108-12

Sukumar M, Liu J, Mehta G U, Patel Si, Roychoudhuri R, Crompton J G, Klebanoff C A, Ji Y, L1 P, Yu Z, Whitehill G D, Clever D, Eil R L, Palmer D C, Mitra S, Rao M, Keyvanfar K, Schrump D S, Wang E, Marincola F M, Gattinoni L, Leonard W J, Muranski P, Finkel T, Restifo N P. 2016. Mitochondrial Membrane Potential Identifies Cells with Enhanced Stemness for Cellular Therapy. *Cell Metab* 23: 63-76

Zha Y, Blank C, Gajewski T F. 2004. Negative regulation of T-cell function by PD-1. *Crit Rev Immunol* 24: 229-37

Blank C, Kuball J, Voelkl S, Wiendl H, Becker B, Walter B, Majdic O, Gajewski T F, Theobald M, Andreesen R, Mackensen A. 2006. Blockade of PD-L1 (137-H1) augments human tumor-specific T cell responses in vitro. *Int J Cancer* 119: 317-27

Zimmerman N P, Vongsa R A, Faherty S L, Salzman N H, Dwinell M B. 2011. Targeted intestinal epithelial deletion of the chemokine receptor CXCR4 reveals important roles for extracellular-regulated kinase-1/2 in restitution. *Lab Invest* 91: 1040-55

Hwang S, Zimmerman N P, Agle K A, Turner J R, Kumar S N, Dwinell M B. 2012. E-cadherin is critical for collective sheet migration and is regulated by the chemokine CXCL12 protein during restitution. *J. Biol. Chem* 287: 22227-40

Gropper Y, Feferman T, Shalit T, Salame T M, Porat Z, Shakhar G. 2017. Culturing CTLs under Hypoxic Conditions Enhances Their Cytolysis and Improves Their Anti-tumor Function. *Cell Rep* 20: 2547-55

Bentolila N Y, Barnhill R L, Lugassy C, Bentolila L A. 2018. Intravital Imaging of Human Melanoma Cells in the Mouse Ear Skin by Two-Photon Excitation Microscopy. *Methods Mol Biol* 1755: 223-32

Tsai S, McOlash L, Palen K, Johnson B, Duris C, Yang O Dwinell M B, Hunt B, Evans D B, Gershan J, James M A. 2018. Development of primary human pancreatic cancer organoids, matched stromal and immune cells and 3D tumor microenvironment models. *BMC Cancer* 18: 335

Spoerri L, Beaumont K A, Anfosso A, Haass N K. 2017. Real-Time Cell Cycle Imaging in a 3D Cell Culture Model of Melanoma. *Methods Mol Biol* 1612: 401-16

Muller I, Kulms D. 2018. A 3D Organotypic Melanoma Spheroid Skin Model. *J Vis Exp* 2018 May 18; (135). doi: 10.3791/57500.

We claim:

1. A mito-magnolol compound according to the following structures:

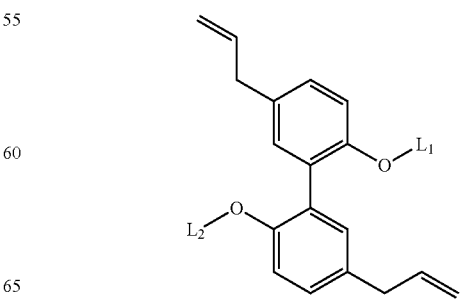

wherein L₁ is

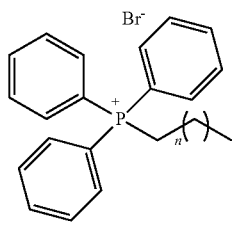

wherein n is an integer from 1-15, and
wherein L₂ is

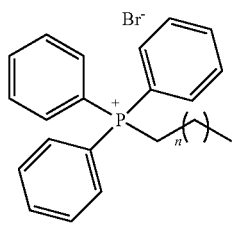

or H, wherein n is an integer from 1-15.

2. The compound of claim 1 wherein n is an integer from 1-12.
3. The compound of claim 1, wherein n is 9 or 10.
4. The compound of claim 1, wherein L₂ is

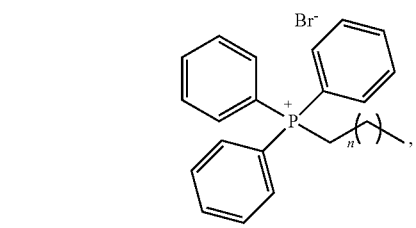

wherein n is an integer from 1-15.

5. The compound of claim 4, wherein n is 9 or 10.
6. The compound of claim 1, wherein L₂ is H.
7. The compound of claim 6, wherein n of L₁ is an integer from 1-12.
8. The compound of claim 7, wherein n is 9 or 10.
9. The compound of claim 1, where the compound is:

10. The compound of claim 1, wherein the compound is

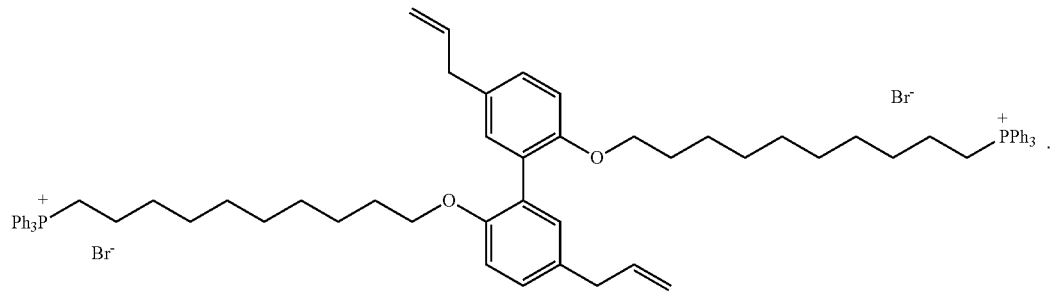

11. A method of reducing or inhibiting tumor growth in a subject comprising administering to the subject a therapeutically effective amount of a pharmaceutical composition comprising at least one mito-magnolol compound of claim 1, wherein the tumor is melanoma, lung cancer, colon cancer or pancreatic cancer.

12. The method of claim 11, wherein the tumor is a lung cancer.

13. The method of claim 11, wherein the tumor is a metastatic tumor.

14. The method of claim 11, wherein the method further comprises treatment of the patient with an antiglycolytic agent and other standard-of-care drug.

15. The method of claim 11, wherein the antiglycolytic agent is selected from the group consisting of 2-deoxyglucose or 3-bromopyruvate.

16. The method of claim 11, wherein the method further comprises treating the patient with surgery, radiation therapy (RT), or chemotherapy (CT) prior to or concurrently with administering the pharmaceutical composition.

17. A method of inhibiting, or reducing metastasis of a cancer comprising administering an effective amount of a pharmaceutical composition comprising at least one mito-magnolol of claim 1 to inhibit or reduce metastasis of cancer in the patient, wherein the cancer is selected from the group consisting of melanoma, colon cancer, lung cancer and pancreatic cancer.

18. The method of claim 17, wherein the metastasis is in a lymph node or distal organ.

19. The compound of claim 1, wherein then of both $L_1$ and $L_2$ is an integer from 1-12.

* * * * *

UNITED STATES PATENT AND TRADEMARK OFFICE
CERTIFICATE OF CORRECTION

PATENT NO. : 11,897,910 B2
APPLICATION NO. : 17/099268
DATED : February 13, 2024
INVENTOR(S) : Balaraman Kalyanaraman et al.

It is certified that error appears in the above-identified patent and that said Letters Patent is hereby corrected as shown below:

In the Specification

Column 2, Line 43, "1a" should be --1α--.

Column 45, Line 27, "40605" should be --4060S--.

Column 45, Line 30, "92725" should be --9272S--.

Column 48, Line 10, "Pan i" should be --Pan J--.

Column 58, Line 15, "SCAR" should be --ECAR--.

Column 58, Line 23, "SCAR" should be --ECAR--.

Column 62, Line 22, "L1 Z" should be --Li Z--.

Column 62, Line 26, "Receptor a Activation" should be --Receptor α Activation--.

Column 63, Line 47, "test (a" should be --test (α--.

Column 67, Line 48, "SCAR" should be --ECAR--.

Column 70, Line 7, "phase 11 study" should be --phase II study--.

Column 72, Line 36, "Dermato/14" should be --Dermatol 14--.

Column 74, Line 63, "L1 S" should be --Li S--.

Column 76, Line 24, "L1 X N" should be --Li XN--.

Signed and Sealed this
Twenty-third Day of April, 2024

Katherine Kelly Vidal
*Director of the United States Patent and Trademark Office*

CERTIFICATE OF CORRECTION (continued)
U.S. Pat. No. 11,897,910 B2

Column 77, Line 52, "C I" should be --CJ--.

Column 78, Line 19, "Si" should be --SJ--.

Column 78, Line 36, "R I" should be --PJ--.

Column 78, Line 56, "L1" should be --Li--.

Column 78, Line 56, "L1" should be --Li--.

Column 78, Line 57, "L1" should be --Li--.

Column 78, Line 58, "L1" should be --Li--.

Column 78, Line 63, "L1" should be --Li--.

Column 79, Line 48, "R I" should be --PJ--.

Column 80, Line 1, "Si" should be --SJ--.

Column 80, Line 2, "L1" should be --Li--.

Column 80, Line 14, "(137-H1)" should be --(B7-H1)--.

In the Claims

Claim 19, Column 83, Line 1, "then" should be --the n--.